United States Patent
Wisniewski et al.

(10) Patent No.: US 8,951,519 B2
(45) Date of Patent: Feb. 10, 2015

(54) IMMUNOTHERAPY TARGETING OF THE SHARED ABNORMAL CONFORMATIONAL STATE OF AMYLOIDOGENIC PEPTIDES/PROTEINS

(71) Applicant: New York University, New York, NY (US)

(72) Inventors: Thomas M. Wisniewski, Staten Island, NY (US); Fernando Goni, New York, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 13/773,264

(22) Filed: Feb. 21, 2013

(65) Prior Publication Data
US 2013/0156783 A1 Jun. 20, 2013

Related U.S. Application Data

(62) Division of application No. 12/774,293, filed on May 5, 2010, now Pat. No. 8,409,584.

(60) Provisional application No. 61/175,645, filed on May 5, 2009.

(51) Int. Cl.
| | | |
|---|---|---|
| *A61K 39/00* | (2006.01) | |
| *C07K 16/00* | (2006.01) | |
| *G01N 33/566* | (2006.01) | |
| *G01N 33/00* | (2006.01) | |
| *A61K 39/395* | (2006.01) | |
| *A61K 9/00* | (2006.01) | |
| *A61K 38/10* | (2006.01) | |
| *C07K 16/18* | (2006.01) | |

(52) U.S. Cl.
CPC ........... *A61K 39/3955* (2013.01); *A61K 9/0019* (2013.01); *A61K 38/10* (2013.01); *A61K 39/0007* (2013.01); *C07K 16/18* (2013.01); *A61K 2039/55505* (2013.01); *C07K 2317/34* (2013.01)
USPC ..................... 424/139.1; 530/387.9; 436/501; 435/7.94

(58) Field of Classification Search
CPC . A61K 39/3955; A61K 9/0019; A61K 38/10; A61K 39/0007; A61K 2039/55505; C07K 16/18; C07K 2317/34
See application file for complete search history.

(56) References Cited

U.S. PATENT DOCUMENTS

| | | |
|---|---|---|
| 5,080,896 A | 1/1992 | Visser et al. |
| 5,695,766 A | 12/1997 | Paul et al. |
| 6,462,171 B1 | 10/2002 | Soto-Jara et al. |
| 6,670,195 B1 | 12/2003 | Ghiso et al. |
| 2003/0166558 A1 | 9/2003 | Frangione et al. |
| 2004/0214774 A1 | 10/2004 | Wisniewski et al. |
| 2006/0199771 A1 | 9/2006 | Chalifour et al. |
| 2009/0081204 A1 | 3/2009 | Frangione et al. |

FOREIGN PATENT DOCUMENTS

WO 2009/009396 A2 1/2009

OTHER PUBLICATIONS

Bendig 1995 "humanization of rodent monoclonal antibodies by CDR grafting" Methods: a companion to methods in enzymology 8:83-93.*
Habicht et al 2007 "directed selection of a conformational antibody domain that prevents mature amyloid fibril formation by stabilizing a(beta) protofibrils" PNAS 104(49):19232-19237.*
Holt et al. 2003 "domain antibodies: proteins for therapy" Trends in biotech 21(11):484-490.*
Kayed et al 2007 "fibril specific, conformation dependent antibodies recognize a generic epitope common to amyloid fibrils and fibrillar oligomers that is absent in prefibrillar oligomers" Molec Neurodegen 2(18):1-11.*
Kayed and Glabe 2007 "Conformation-dependent anti-amyloid oligomer antibodies" Methods in Enzymology 43(17):326-344.*
O'Nuallain and Wetzel 2002 "Conformational abs recognizing a generic amyloid fibril epitope" PNAS 99(3):1485-1490.*
International Search Report for PCT/US2010/033732, dated Jan. 3, 2011.
Bruce Alberts et al., Molecular Biology of the Cell, 3 ed., Garland Publishing, Inc. pp. 129-130 (1994).
Strategene Product Catalog, p. 215 (Appendix), DNA Migration in Agarose and Acrylamide Gels (1991).
Harmsen & De Haard, "Properties, Production, and Applications of Camelid Single-Domain Antibody Fragments," Appl. Microbiol. Biotechnol. 77:13-22 (2007).

* cited by examiner

*Primary Examiner* — Gregory S Emch
*Assistant Examiner* — Adam M Weidner
(74) *Attorney, Agent, or Firm* — LeClairRyan, a Professional Corporation

(57) ABSTRACT

The present invention is directed to pharmaceutical agents and compositions useful for the treatment and prevention of amyloid disease in a subject. The invention further relates to isolated antibodies that recognize a common conformational epitope of amyloidogenic proteins or peptides that are useful for the diagnosis, treatment, and prevention of amyloid disease.

25 Claims, 21 Drawing Sheets

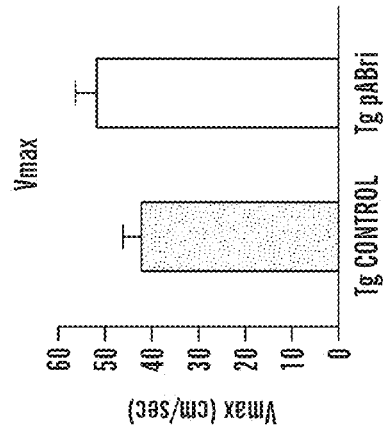
FIG. 12A
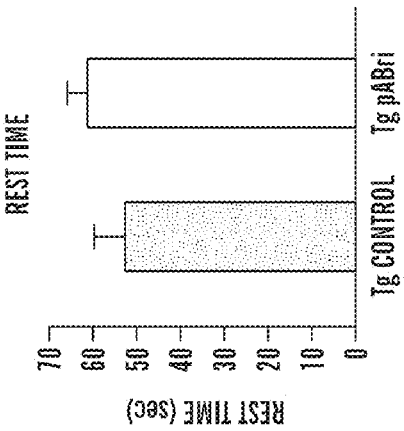
FIG. 12B
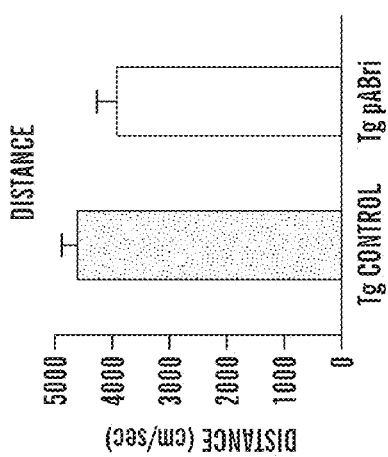
FIG. 12C
FIG. 12D

IMMUNOTHERAPY TARGETING OF THE SHARED ABNORMAL CONFORMATIONAL STATE OF AMYLOIDOGENIC PEPTIDES/PROTEINS

This application is a divisional of U.S. patent application Ser. No. 12/774,293, filed May 5, 2010, which claims the priority benefit of U.S. Provisional Patent Application Ser. No. 61/175,645, filed May 5, 2009, each of which is hereby incorporated by reference in its entirety.

This invention was made with government support under grant numbers AG20245, AG08051, and AG15408 awarded by the National Institutes of Health. The government has certain rights in this invention.

FIELD OF THE INVENTION

The present invention relates to pharmaceutical agents and antibodies suitable for the diagnosis, prevention, and treatment of amyloid disease.

BACKGROUND OF THE INVENTION

Amyloidosis broadly encompasses a variety of diseases that are characterized by the extracellular or intracellular deposition of amyloid proteins in tissues and/or organs. Amyloids are insoluble fibrous protein/peptide aggregates and their deposition may occur in localized sites or systemically. The fibrillar composition of these deposits is an identifying characteristic for the various forms of amyloid disease. In some cases the amyloid protein/peptide accumulates intracellullary, resulting in cell dysfunction and ultimately cell death. Examples of intracellular amyloid proteins include α-synuclein, forming Lewy bodies in Parkinson's disease, and huntington, forming neuronal inclusions in Huntington disease. The pathogenesis of Alzheimer's disease (AD), the most common of the amyloid related neurodegenerative disorders, is linked to the cleavage of the amyloid precursor protein generating the amyloid-β (Aβ) peptide which undergoes a shape change into a pathological conformer having a high β-sheet content. Intracerebral and cerebrovascular deposits composed primarily of fibrils of the pathological Aβ peptide are characteristic of both familial and sporadic forms of AD. In addition to Aβ, abnormally phosphorylated tau protein forms toxic oligomeric structures and neurofibrillary tangles in AD. Similar to AD, prion-associated diseases, such as Creutzfeld-Jacob disease, have also been characterized as amyloid diseases. The pathogenesis of prion disease is linked to a change of the cellular prion protein (PrP$^C$) into the disease associated PrP$^{Sc}$ (Sc for scrapie). Currently, there is no effective therapy for any of these disorders.

An active area of translational research and current clinical trials for amyloid disease has focused on immunotherapy, using both passive and active immunization against amyloid proteins, particularly Aβ in AD (Wisniewski et al., "Amyloid-β Immunization for Alzheimer's Disease," *Lancet Neurol* 7:805-811 (2008)). Although immunomotherapy holds great promise as a means of reducing amyloid deposition, it, unfortunately, has been accompanied by major obstacles. Specific problems associated with immunotherapy that were identified in a clinical trial for AD include the potential of toxicity from encephalitis (related to excessive cell mediated immunity), the immunological targeting of both the normal and abnormal Aβ peptide, the failure to address tau related pathology, and the apparent poor efficacy. Moreover, although autopsy data from this early immunotherapy vaccine trial suggested that many patients had a significant reduction in amyloid burden, these patients exhibited only minor cognitive benefits (Wisniewski et al., "Amyloid-β Immunization for Alzheimer's Disease," *Lancet Neurol* 7:805-811 (2008) and Holmes et al., "Long Term Effects of Aβ42 Immunization in Alzheimer's Disease: Immune Response, Plaque Removal and Clinical Function," *Lancet* 372:216-223 (2008)). Therefore, an immunotherapeutic approach that can effectively reduce amyloid burden and overcome the aforementioned problems is warranted.

The present invention is directed to overcoming these and other deficiencies in the art.

SUMMARY OF THE INVENTION

A first aspect of the present invention is directed to a pharmaceutical agent that is selected from the group consisting of (i) a polymer of a first peptide comprising the amino acid sequence $X_{1a}X_{2a}X_{3a}X_{4a}X_{5a}X_{6a}X_{7a}X_{8a}X_{9a}X_{10a}X_{11a}X_{12a}X_{13a}$ (SEQ ID NO: 19), wherein $X_{1a}$ is C, M, S, or G; $X_{2a}$ is T, S, or C; $X_{3a}$ is K, R, or H; $X_{4a}$ is S, T, or C; $X_{5a}$ is V, I, or L; $X_{6a}$ is R, K, or H; $X_{7a}$ is R, K, or H; $X_{8a}$ is Q or N; $X_{9a}$ is L, I, or V; $X_{10a}$ is L, I, or V; $X_{11a}$ is D or E; $X_{12a}$ is D or E; $X_{13a}$ is Q or N; (ii) a polymer of a second peptide comprising the amino acid sequence $X_{1b}X_{2b}X_{3b}X_{4b}X_{5b}X_{6b}X_{7b}X_{8b}X_{9b}X_{10b}X_{11b}X_{12b}X_{13b}$ (SEQ ID NO: 20) wherein $X_{1b}$ is C, M, S, or G; $X_{2b}$ is F, Y, or W; $X_{3b}$ is Q or N; $X_{4b}$ is I, L, or V; $X_{5b}$ is F, Y, or W; $X_{6b}$ is I, L, or V; $X_{7b}$ is Q or N; $X_{8b}$ is T, S, or C; $X_{9b}$ is N or Q; $X_{10b}$ is D or E; $X_{11b}$ is R, K, or H; $X_{12b}$ is H, R, or K; $X_{13b}$ is Y, W, or F; and (iii) a polymer of a fusion peptide comprising the first and/or second peptides.

A second aspect of the present invention is directed to an isolated antibody or binding portion thereof having antigenic specificity for an epitope of a polymerized peptide. The polymerized peptide is selected from the group consisting of (i) a polymer of a first peptide comprising the amino acid sequence $X_{1a}X_{2a}X_{3a}X_{4a}X_{5a}X_{6a}X_{7a}X_{8a}X_{9a}X_{10a}X_{11a}X_{12a}X_{13a}$ (SEQ ID NO: 19), wherein $X_{1a}$ is C, M, S, or G; $X_{2a}$ is T, S, or C; $X_{3a}$ is K, R, or H; $X_{4a}$ is S, T, or C; $X_{5a}$ is V, I, or L; $X_{6a}$ is R, K, or H; $X_{7a}$ is R, K, or H; $X_{8a}$ is Q or N; $X_{9a}$ is L, I, or V; $X_{10a}$ is L, I, or V; $X_{11a}$ is D or E; $X_{12a}$ is D or E; $X_{13a}$ is Q or N; (ii) a polymer of a second peptide comprising the amino acid sequence $X_{1b}X_{2b}X_{3b}X_{4b}X_{5b}X_{6b}X_{7b}X_{8b}X_{9b}X_{10b}X_{11b}X_{12b}X_{13b}$ (SEQ ID NO: 20), wherein $X_{1b}$ is C, M, S, or G; $X_{2b}$ is F, Y, or W; $X_{3b}$ is Q or N; $X_{4b}$ is I, L, or V; $X_{5b}$ is F, Y, or W; $X_{6b}$ is I, L, or V; $X_{7b}$ is Q or N; $X_{8b}$ is T, S, or C; $X_{9b}$ is N or Q; $X_{10b}$ is D or E; $X_{11b}$ is R, K, or H; $X_{12b}$ is H, R, or K; $X_{13b}$ is Y, W, or F; and (iii) a polymer of a fusion peptide comprising the first and/or second peptides.

Another aspect of the present invention is directed to an isolated first peptide comprising the amino acid sequence of $X_{1a}X_{2a}X_{3a}X_{4a}X_{5a}X_{6a}X_{7a}X_{8a}X_{9a}X_{10a}X_{11a}X_{12a}X_{13a}$ (SEQ ID NO: 19), wherein $X_{1a}$ is C, M, S, or G; $X_{2a}$ is T, S, or C; $X_{3a}$ is K, R, or H; $X_{4a}$ is S, T, or C; $X_{5a}$ is V, I, or L; $X_{6a}$ is R, K, or H; $X_{7a}$ is R, K, or H; $X_{8a}$ is Q or N; $X_{9a}$ is L, I, or V; $X_{10a}$ is L, I, or V; $X_{11a}$ is D or E; $X_{12a}$ is D or E; $X_{13a}$ is Q or N, with the proviso that the isolated first peptide does not have an amino acid sequence of SEQ ID NO:2.

Another aspect of the present invention is directed to an isolated second peptide comprising the amino acid sequence of $X_{1b}X_{2b}X_{3b}X_{4b}X_{5b}X_{6b}X_{7b}X_{8b}X_{9b}X_{10b}X_{11b}X_{12b}X_{13b}$ (SEQ ID NO: 20), wherein $X_{1b}$ is C, M, S, or G; $X_{2b}$ is F, Y, or W; $X_{3b}$ is Q or N; $X_{4b}$ is I, L, or V; $X_{5b}$ is F, Y, or W; $X_{6b}$ is I, L, or V; $X_{7b}$ is Q or N; $X_{8b}$ is T, S, or C; $X_{9b}$ is N or Q; $X_{10b}$ is D or E; $X_{11b}$ is R, K, or H; $X_{12b}$ is H, R, or K; $X_{13b}$ is Y, W, or F, with the proviso that the isolated second peptide does not have an amino acid sequence of SEQ ID NO:8.

Another aspect of the present invention is directed to an isolated fusion peptide of the first and/or second peptides of the invention. The isolated fusion peptide has an amino acid sequence selected from the group consisting of SEQ ID NO:13, SEQ ID NO:15, and SEQ ID NO:17.

The development of an effective immunotherapeutic approach for the prevention and treatment of amyloid related diseases has been hindered by potential cell-mediated toxicity, non-specific immunological targeting of both normal and amyloidogenic proteins, and overall poor efficacy. The immunotherapeutic approach of the present invention employs polymerized peptides and fusion peptides, having no amino acid sequence homology to other human proteins, to generate a specific immunological response to conformational epitopes that are shared by various amyloidogenic proteins, thereby overcoming many of the above noted obstacles.

BRIEF DESCRIPTION OF THE DRAWINGS

FIG. 10A is a western blot using specific polyclonal anti-ABri antisera. The freshly dissolved ABri peptide was run in lane 1. This preparation of ABri is mainly monomeric with some lower order aggregates of dimers and tetramers in contrast to the polymerized ABri (pABri) peptide which has less monomer with a predominance of higher order aggregates in a range of 30 to 100 kDa (lane 2), FIG. 10B shows the circular dichroism of these peptides. The freshly dissolved ABri peptide has a predominant random coil structure with a minimum at 195 nm, in contrast to the polymerized ABri peptide that has a predominant β-sheet structure with a minimum at 220 nm and a maximum at 195 nm. FIG. 10C is an electron micrograph of negatively stained polymerized ABri peptide, which is predominately in the form of spherical particles of ~10 nm (Scale bar, 100 nm).

In FIGS. 11A and 11B, titers of IgM and IgG in controls are shown, respectively. In FIGS. 11C and 11D, titers of IgM and IgG in pABri vaccinated mice are shown, respectively (*$p<0.0001$, #$p<0.01$).

FIGS. 12A-12D show the results of locomotor activity testing comparing APP/PSI transgenic (Tg) control and Tg pABri vaccinated mice. No significant differences were noted in distance traveled (FIG. 12A), maximum velocity (Vmax) (FIG. 12B), mean velocity (Vmean) (FIG. 12C), or in resting time (FIG. 12D).

FIGS. 14A-14B are bar graphs showing cortical (FIG. 14A) and hippocampal (FIG. 14B) amyloid burden in Tg control and pABri vaccinated Tg mice. There were significant reductions in the amyloid burden (% area occupied by 4G8/6E10 immunoreactivity) in both the cortex (85% reduction) and hippocampus (65% reduction); $p=0.0001$ and $p=0.0002$, respectively. FIGS. 14C-14F show representative cortical (FIGS. 14C and 14D) and hippocampal (FIGS. 14E and 14F) sections of control Tg mice (FIGS. 14C and 14E) and pABri vaccinated mice (FIGS. 14D and 14F) immunostained with anti-Aβ antibodies 4G8 and 6E10.

In FIG. 18A, lanes 1 and 3 contain Aβ1-40 monomer/oligomers and lanes 2 and 4 contain Aβ1-42 monomer/oligomers. Monoclonal (mAb) antibody 3D6 (lanes 1-2; 1:1000) detected Aβ oligomers at ~56 kDa and higher molecular weights, but did not recognize Aβ monomers. The monoclonal antibody 6E10 (lanes 3-4; 1:20,000) preferentially detected monomeric Aβ with faint reactivity of Aβ1-42 oligomers (lane 4) as previously reported (Kayed et al., "Fibril Specific, Conformation Dependent Antibodies Recognize a Generic Epitope Common To Amyloid Fibrils and Fibrillar Oligomers That Is Absent in Prefibrillar Oligomers," *Mol Neurodegener* 2:18 (2007), which is hereby incorporated by reference in its entirety). In FIG. 18B protease-K digested normal brain homogenate (lanes 1, 4), ME7 brain homogenate (lanes 2, 5), and 139A brain homogenate (lanes 3, 6) were immunoblotted with 3D6 (lanes 1-3) or mouse mAb 6D11, having antigen specificity for prion protein (PrPc) and its insoluble conformer PrPSc (lanes 4-6). mAb 3D6 immunoreactivity against PrP$^{Sc}$ was detected, demonstrating 3D6 recognition of a conformational epitope shared by both PrP$^{Sc}$ and Aβ oligomers In FIG. 19D, 3D6 antibody was absorbed with aggregated Aβ prior to tissue incubation as a control, and no immunolabeling was detected.

DETAILED DESCRIPTION OF THE INVENTION

Figure 1A:
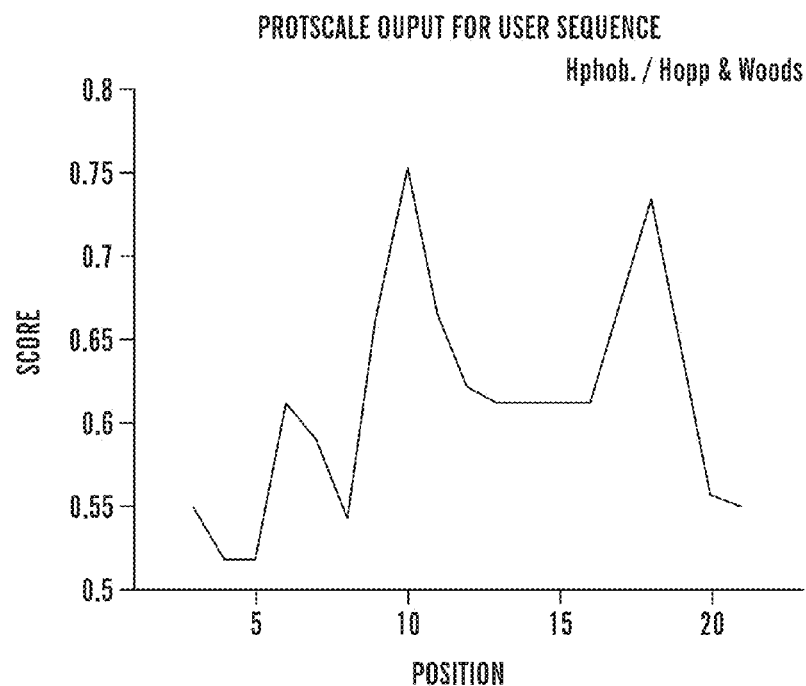
FIGS. 1A-1B are graphs comparing the hydrophobicity of first peptides of the present invention having amino acid sequences of SEQ ID NO:2 and SEQ ID NO:5 by Hopp and Woods analysis. Although the peptides have only 15% amino acid sequence homology (two out of 13 amino acids) to each other, the two peptides have very similar hydrophobic character.

A first aspect of the present invention is directed to a pharmaceutical agent. The pharmaceutical agent of the present invention is selected from the group consisting of (i) a polymer of a first peptide comprising the amino acid sequence $X_{1a}X_{2a}X_{3a}X_{4a}X_{5a}X_{6a}X_{7a}X_{8a}X_{9a}X_{10a}X_{11a}X_{12a}X_{13a}$ (SEQ ID NO: 19), wherein $X_{1a}$ is C, M, S, or G; $X_{2a}$ is T, S, or C; $X_{3a}$ is K, R, or H; $X_{4a}$ is S, T, or C; $X_{5a}$ is V, I, or L; $X_{6a}$ is R, K, or H; $X_{7a}$ is R, K, or H; $X_{8a}$ is Q or N; $X_{9a}$ is L, I, or V; $X_{10a}$ is L, I, or V; $X_{11a}$ is D or E; $X_{12a}$ is D or E; $X_{13a}$ is Q or N; (ii) a polymer of a second peptide comprising the amino acid sequence $X_{1b}X_{2b}X_{3b}X_{4b}X_{5b}X_{6b}X_{7b}X_{8b}X_{9b}X_{10b}X_{11b}X_{12b}X_{13b}$ (SEQ ID NO: 20) wherein $X_{1b}$ is C, M, S, or G; $X_{2b}$ is F, Y, or W; $X_{3b}$ is Q or N; $X_{4b}$ is I, L, or V; $X_{5b}$ is F, Y, or W; $X_{6b}$ is I, L, or V; $X_{7b}$ is Q or N; $X_{8b}$ is T, S, or C; $X_{9b}$ is N or Q; $X_{10b}$ is D or E; $X_{11b}$ is R, K, or H; $X_{12b}$ is H, R, or K; $X_{13b}$ is Y, W, or F; and (iii) a polymer of a fusion peptide comprising the first and/or second peptides.

In one embodiment of the present invention, the pharmaceutical agent is a polymer of a first peptide. The first peptide of the present invention has an amino acid sequence of $X_{1a}X_{2a}X_{3a}X_{4a}X_{5a}X_{6a}X_{7a}X_{8a}X_{9a}X_{10a}X_{11a}X_{12a}X_{13a}$ (SEQ ID NO: 19), consisting of four units. The first unit (i.e., unit 1) of the first peptide, consisting of amino acid residue $X_{1a}$, is a reactive or non-reactive, polar or non-polar cysteine (C) residue or a glycine (G), methionine (M) or serine (S) residue. The second unit (i.e., unit 2) of the first peptide (SEQ ID NO: 19) consists of residues $X_{2a}$ to $X_{4a}$. This unit contains a hydrophilic, basic, positively charged amino acid at position $X_{3a}$ (e.g., lysine (K) or arginine (R)) that is flanked by two small, polar (mildly acidic depending on the surroundings) amino acids in positions $X_{2a}$ and $X_{4a}$ (e.g., threonine (T) or S). The amino acid residue of $X_{3a}$ can also accommodate a partially charged histidine (H) residue when positions $X_{2a}$ and $X_{4a}$ are serine. The third unit (i.e., unit 3) of the first peptide of the present invention consists of residues $X_{5a}$ to $X_{8a}$ of SEQ ID NO:19. This unit contains a charged core with two hydrophilic positively charged basic amino acids in positions $X_{6a}$ and $X_{7a}$ (e.g., R, K, or H) flanked by a long chain aliphatic, non-polar amino acid at the amino-terminal position $X_{5a}$ (e.g., valine (V), isoleucine (I), or leucine (L)), and a polar, uncharged amino acid lacking a reactive oxygen at the carboxyl position $X_{8a}$ (e.g., glutamine (Q) or asparagine (N)). Either position $X_{6a}$ or $X_{7a}$ can accommodate a histidine residue if the other residue is an arginine residue. The fourth unit (i.e., unit 4) of the first peptide of the present invention consists of residues at positions $X_{9a}$ to $X_{13a}$. This unit contains, on the amino-terminal side, two long, aliphatic, non-polar amino acids at positions $X_{9a}$ and $X_{10a}$ (e.g., L or I indistinctly; or V in both positions), and at the carboxyl end, a complementary polar, uncharged amino acid lacking a reactive oxygen position at position $X_{13a}$ (e.g., Q or N). The core residues of $X_{11a}$ and $X_{12a}$ have two hydrophilic, acidic, negatively charged amino acids (e.g., aspartic acid (D) or glutamic acid (E)).

In one embodiment of the present invention the four units (i.e., units 1, 2, 3, and 4) of the first peptide are ordered 1-2-3-4 as described above. Alternatively, the first peptide may assume any permutations of the above ordered second, third, and fourth units. For example, the four units of the first peptide may be ordered 1-2-4-3, 1-3-2-4, 1-3-4-2, 1-4-2-3, or 1-4-3-2.

Following the above criteria for determining amino acid composition of the four units of the first peptide, a defined genus of structurally similar first peptides are generated. As used herein, "structural similarity" refers to similarities in peptide polarity, β-sheet content, total β-sheet content, parallel β-sheet content, flexibility, coil average, and hydrophobicity. As a result of the structural similarities, each of the first peptides generated in accordance with the criteria above are suitable in carrying out the methods of the present invention that are described infra.

Consistent with the above parameters, the first peptide of the present invention has an amino acid sequence of SEQ ID NO:19 where $X_{1a}$ is C, M, S, or G; $X_{2a}$ is T, S, or C; $X_{3a}$ is K, R, or H; $X_{4a}$ is S, T, or C; $X_{5a}$ is V, I, or L; $X_{6a}$ is R, K, or H; $X_{7a}$ is R, K, or H; $X_{8a}$ is Q or N; $X_{9a}$ is L, I, or V; $X_{10a}$ is L, I, or V; $X_{11a}$ is D or E; $X_{12a}$ is D or E; $X_{13a}$ is Q or N. In a preferred embodiment the first peptide has an amino acid sequence of SEQ ID NO:19 where $X_{1a}$ is C; $X_{2a}$ is T or S; $X_{3a}$ is K or R; $X_{4a}$ is S or T; $X_{5a}$ is V or L; $X_{6a}$ is R or K; $X_{7a}$ is R or K; $X_{8a}$ is Q or N; $X_{9a}$ is L or I; $X_{10a}$ is L or I; $X_{11a}$ is D or E; $X_{12a}$ is D or E; $X_{13a}$ is Q or N. More preferably, the first peptide of the present invention has an amino acid sequence of CSRTVKKNIIEEN (SEQ ID NO:2). The amino acid sequence of SEQ ID NO:2 is the amino acid sequence of the last thirteen amino acids of the Familial British Dementia amyloid peptide (ABri peptide; EASNCFAIRHFENK-FAVETLICSRTVKKNIIEEN (SEQ ID NO:1)). Alternatively, the first peptide of the present invention has an amino acid sequence of CSRSVKKQIIEEN (SEQ ID NO:3) or CTKTLRRQLLDDQ (SEQ ID NO:5).

Figure 1B:
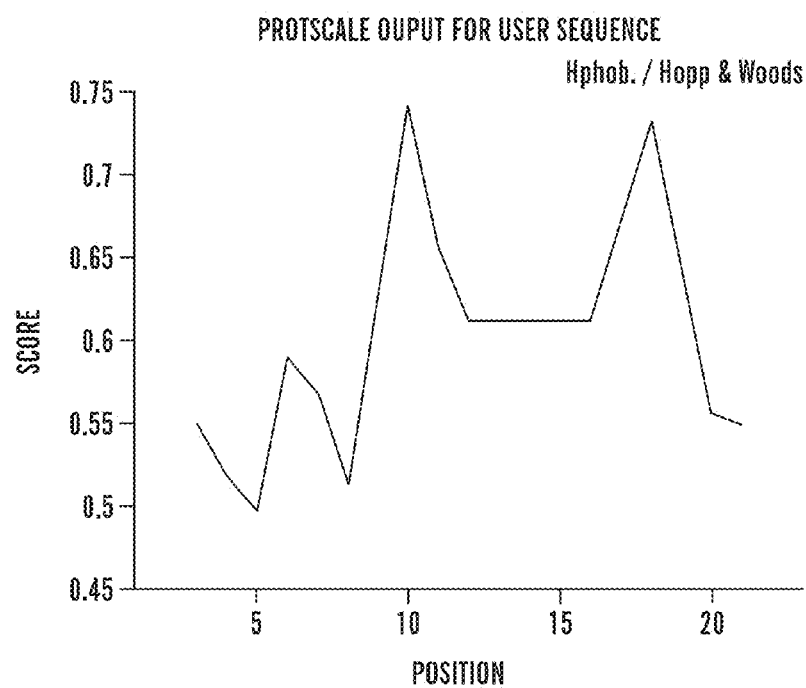
Figure 2A:
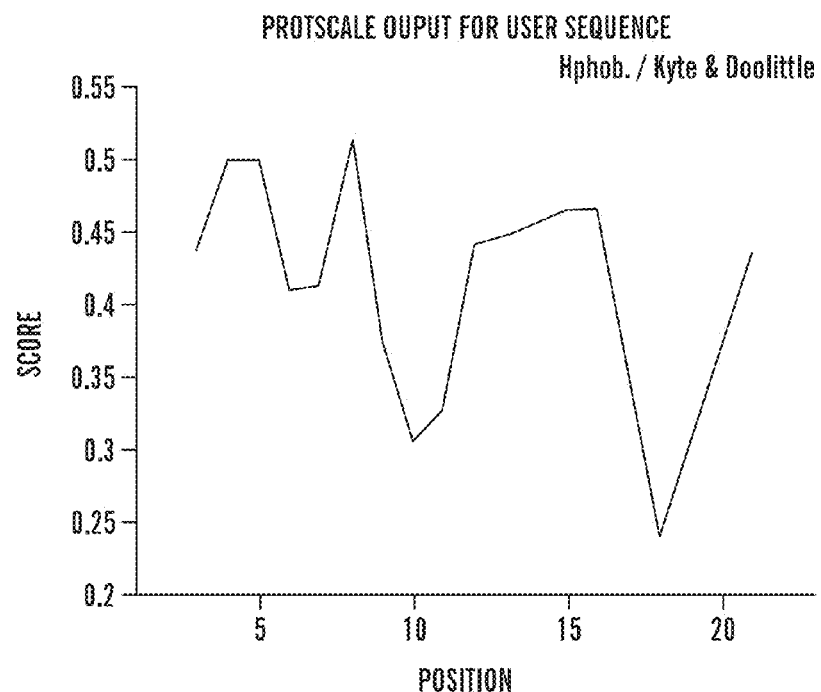
FIGS. 2A-2B are graphs comparing the hydrophobicity of first peptides of the present invention having amino acid sequences of SEQ ID NO:2 and SEQ ID NO:5 by Kyte and Doolittle analysis. Although the peptides have only 15% amino acid sequence homology to each other, the two peptides have very similar hydrophobic character.
Figure 2B:
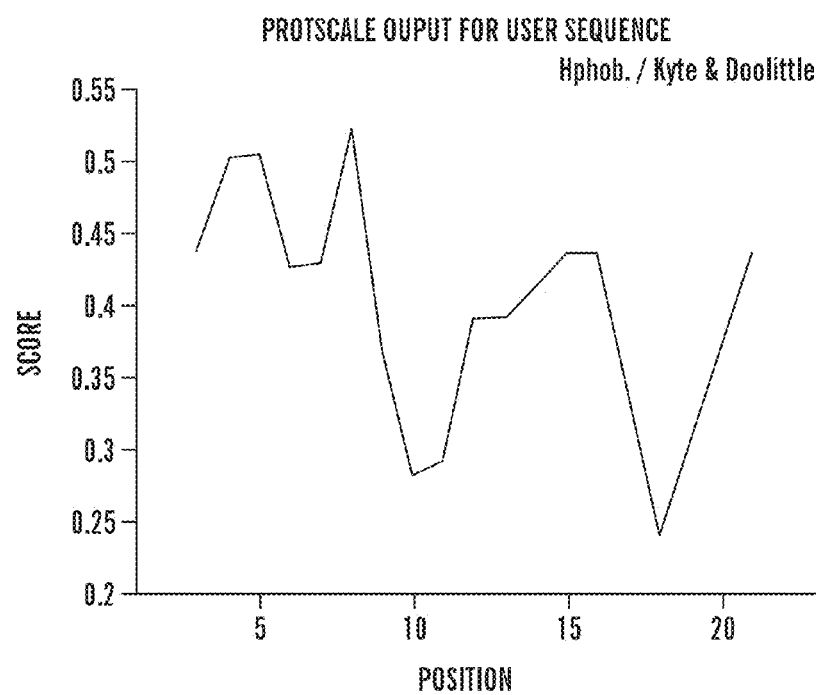
Figure 3A:
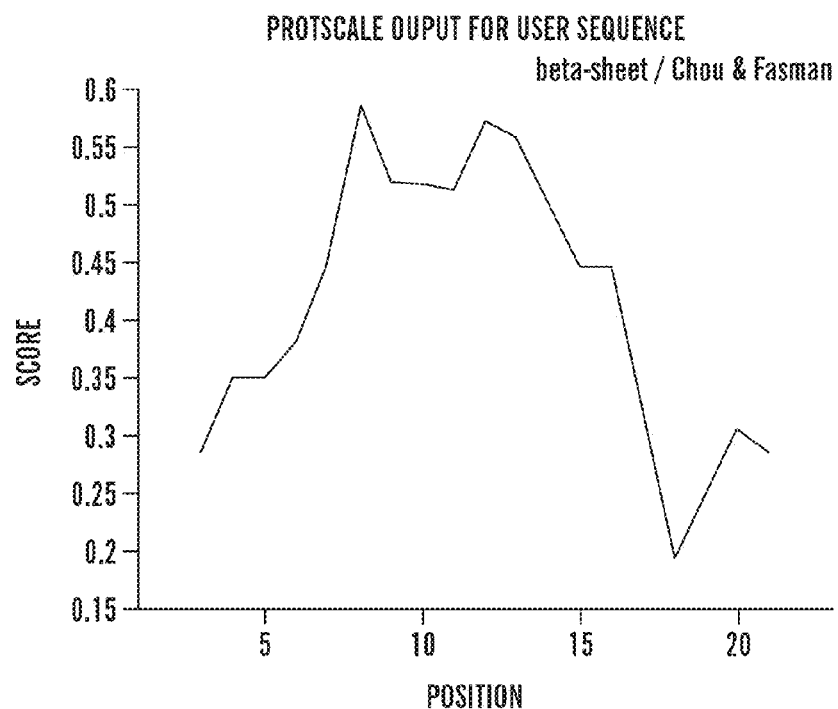
FIGS. 3A-3B are graphs comparing the β-sheet content of first peptides of the present invention having amino acid sequences of SEQ ID NO:2 and SEQ ID NO:5 using Chou-Fasman analysis. Although the peptides have only 15% amino acid sequence homology to each other, the two peptides are structurally similar as demonstrated by their β-sheet content.
Figure 3B:
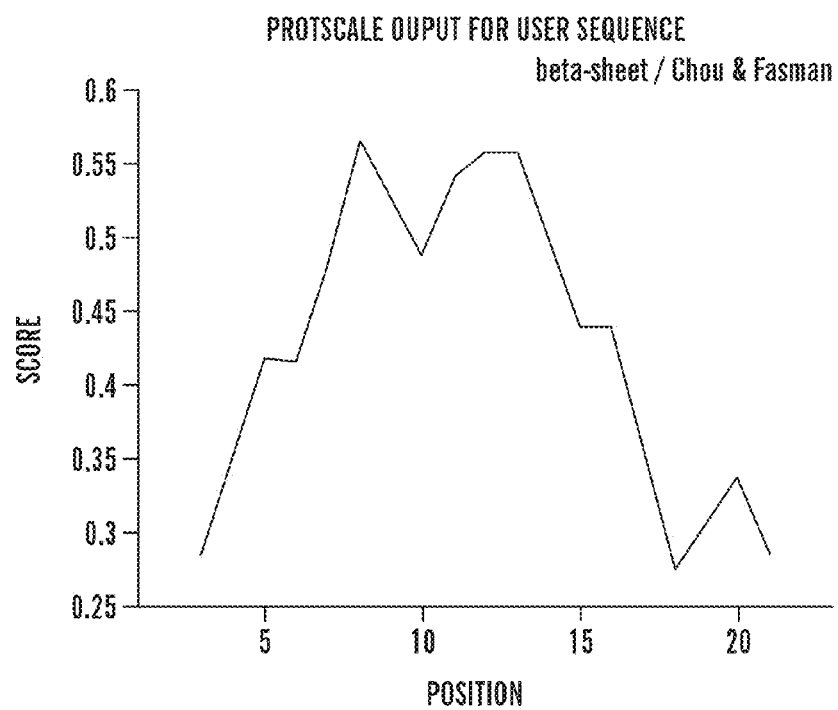

In accordance with this aspect of the invention, the genus of first peptides designed using the criteria described above, may have little amino acid sequence identity to each other. Regardless of the extent of amino acid sequence homology, however, all first peptides of the present invention are structurally similar to each other as demonstrated by their hydrophobicity and β-sheet content. FIGS. 1A-1B are graphs showing the similarity in hydrophobicity between a first peptide of the present invention having an amino acid sequence of SEQ ID NO:2 (FIG. 1A) and a first peptide having an amino acid sequence of SEQ ID NO:5 (FIG. 1B). The first peptide of SEQ ID NO:5 has 15% amino acid sequence homology (two out of thirteen amino acids) to the first peptide of SEQ ID NO:2; however, both peptides have the same hydrophobic character. This similarity in hydrophobicity was confirmed by Kyte and Doolittle analysis as shown in FIG. 2A (SEQ ID NO:2) and FIG. 2B (SEQ ID NO:5). The similarity in β-sheet content is shown in FIGS. 3A-3B with the β-sheet content of SEQ ID NO:2 shown in FIG. 3A and the β-sheet content of SEQ ID NO:5 shown in FIG. 3B. Despite having very little sequence homology to each other, the first peptides of the present invention are designed to ensure similar secondary structural characteristics, and, therefore, similar antigenicity upon polymerization.

In another embodiment, the first peptide of the present invention is a reverse first peptide. A reverse first peptide is one in which the above described four units of SEQ ID NO:19 are in reverse order (i.e., 4-3-2-1). Permutations of the second, third, and fourth units in reverse order are also contemplated (i.e., 4-2-3-1, 3-4-2-1, 2-4-3-1, 3-2-4-1, and 2-3-4-1). This reverse first peptide is also suitable for use in the present invention.

In another embodiment of the present invention, the pharmaceutical agent is a polymer of second peptide of the present invention having an amino acid sequence of $X_{1b}X_{2b}X_{3b}X_{4b}X_{5b}X_{6b}X_{7b}X_{8b}X_{9b}X_{10b}X_{11b}X_{12b}X_{13b}$ (SEQ ID NO: 20) containing three units. The first unit (i.e., unit 1) of the second peptide, consisting of amino acid residue $X_{1b}$, is a reactive or unreactive, polar or non-polar cysteine residue, or a G, M, or S residue. The second unit (i.e., unit 2) of the second peptide consists of amino acid residues $X_{2b}$ to $X_{7b}$ of SEQ ID NO:20. This second unit is further divided into three subunits. The first subunit contains amino acids residues $X_{2b}$ to $X_{5b}$, having a core polar, uncharged amino acid lacking a reactive oxygen at position $X_{3b}$ (e.g., Q or N) and a long aliphatic, non-polar amino acid at position $X_{4b}$ (e.g., I, L, or V). This core is flanked by aromatic, hydrophobic amino acids at positions $X_{2b}$ and $X_{5b}$ (e.g., phenylalanine (F), tyrosine (Y), or tryptophan (W)). The second subunit consists of amino acid residues $X_{4b}$ to $X_{6b}$, which contain an aromatic, hydrophobic core at position $X_{5b}$ (e.g., F, Y, or W), flanked by two long aliphatic, non-polar amino acids at positions $X_{4b}$ and $X_{6b}$ (e.g., I or L indistinctly; or V in both positions). This subunit can shift the hydrophobicity momentum of the peptide. The third subunit extends from residues $X_{3b}$ to $X_{7b}$. The aromatic hydrophobic amino acid at the core position $X_{5b}$ is flanked by two long aliphatic, non polar amino acids at positions $X_{4b}$ and $X_{6b}$, and framed and stabilized by two polar, uncharged amino acids lacking a reactive oxygen at positions $X_{3b}$ and $X_{7b}$ (e.g., Q or N). Residue $X_{8b}$ of SEQ ID NO:20 is a linker residue, consisting of a small polar (mildly acidic depending on the surroundings) amino acid (e.g., T, S, or C). The third unit (i.e., unit 3) of the second peptide of the present invention includes residues $X_{9b}$ to $X_{13b}$. The core of this unit (i.e., $X_{9b}$ and $X_{10b}$) is a match of a stabilizer polar, uncharged amino acid (e.g., N or Q), and a hydrophilic, acidic, negatively charged amino acid (e.g., D or E). This core is surrounded by two hydrophilic, basic, positively charged and half positively charged amino acids at positions $X_{11b}$ and $X_{12b}$ (e.g., H is always in one of the two positions and the other position is occupied by either K or R) irrespectively. This third unit is flanked at the carboxyl end by an aromatic amino acid at position $X_{13b}$ (e.g., Y, W, or F). Following these parameters, a defined genus of structurally similar second peptides are generated (i.e., peptide fragments having similar polarity, β-sheet content, total β-sheet content, parallel β-sheet content, flexibility, coil average, and hydrophobicity). As a result of the structural similarities, each of the second peptides designed using the above described criteria are suitable in carrying out the methods of the present invention that are described infra.

Consistent with the above description, the second peptide of the present invention has an amino acid sequence of SEQ ID NO:20 where $X_{1b}$ is C, M, S, or G; $X_{2b}$ is F, Y, or W; $X_{3b}$ is Q or N; $X_{4b}$ is I, L, or V; $X_{5b}$ is F, Y, or W; $X_{6b}$ is I, L, or V; $X_{7b}$ is Q or N; $X_{8b}$ is T, S, or C; $X_{9b}$ is N or Q; $X_{10b}$ is D or E; $X_{11b}$ is R, K, or H; $X_{12b}$ is H, R, or K; $X_{13b}$ is Y, W, or F. In a preferred embodiment the second peptide of the present invention has an amino acid sequence of SEQ ID NO:20 where $X_{1b}$ is C; $X_{2b}$ is F or W; $X_{3b}$ is Q or N; $X_{4b}$ is I or L; $X_{5b}$ is F or W; $X_{6b}$ is I or L; $X_{7b}$ is Q or N; $X_{8b}$ is T or S; $X_{9b}$ is N or Q; $X_{10b}$ is D or E; $X_{11b}$ is R, K, or H; $X_{12b}$ is R, K, or H; $X_{13b}$ is Y or F. More preferably, the second peptide of the present invention has an amino acid sequence of CFNLFLNSQEKHY (SEQ ID NO:8). The amino acid sequence of SEQ ID NO:8 is the same amino acid sequence of the last thirteen amino acids of the Familial Danish Dementia amyloid peptide (ADan; EASNCFAIRHFENKFAVETLICFNLFLN-SQEKHY (SEQ ID NO:7)). The second peptide of the present invention can also have the amino acid sequence of CFQLFLNTQEKHY (SEQ ID NO:9) or CWQL-WIQSNDHKF (SEQ ID NO:11).

In one embodiment of the present invention the three units (i.e., units 1, 2, and 3) of the second peptide are ordered 1-2-3 as described above. Alternatively, the second peptide may assume permutations of the second and third units. For example, the three units of the second peptide may be ordered 1-3-2.

Figure 4A:
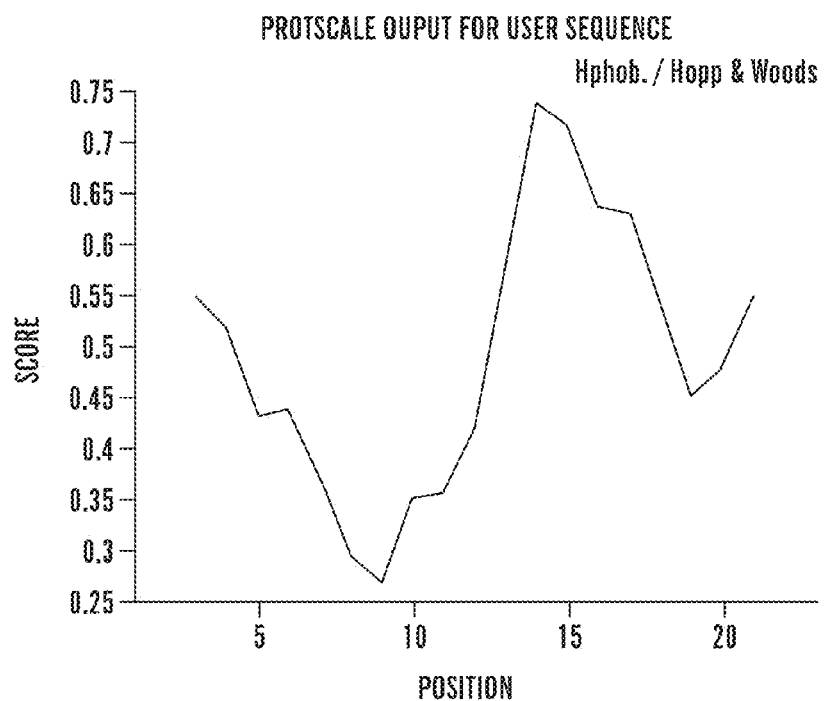
FIGS. 4A-4B are graphs comparing the hydrophobicity of second peptides of the present invention having amino acid sequences of SEQ ID NO:8 and SEQ ID NO:11 by Hopp and Woods analysis. Although the peptides have only 23% amino acid sequence homology to each other (three out of 13 amino acids), the two peptides have very similar hydrophobic character.
Figure 4B:
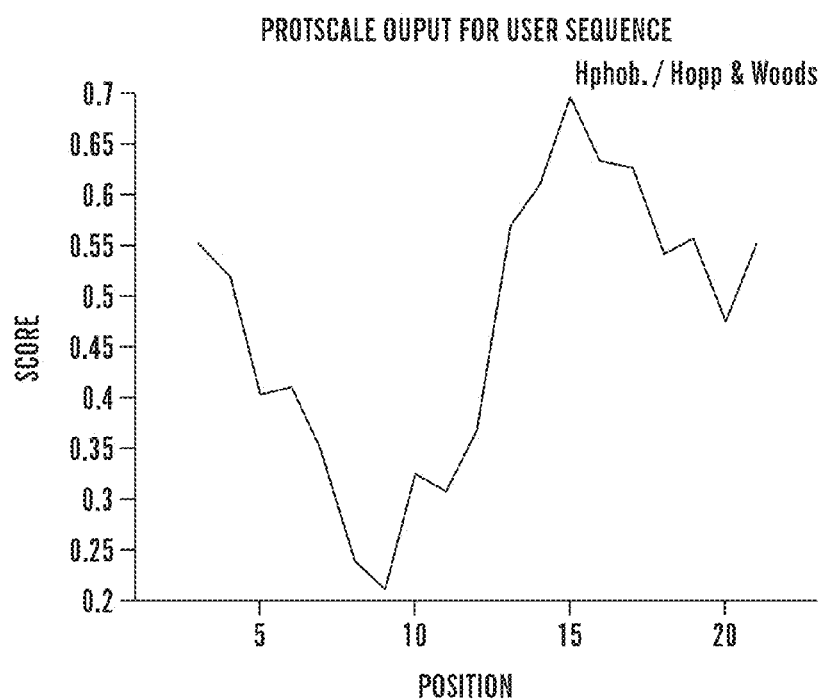
Figure 5A:
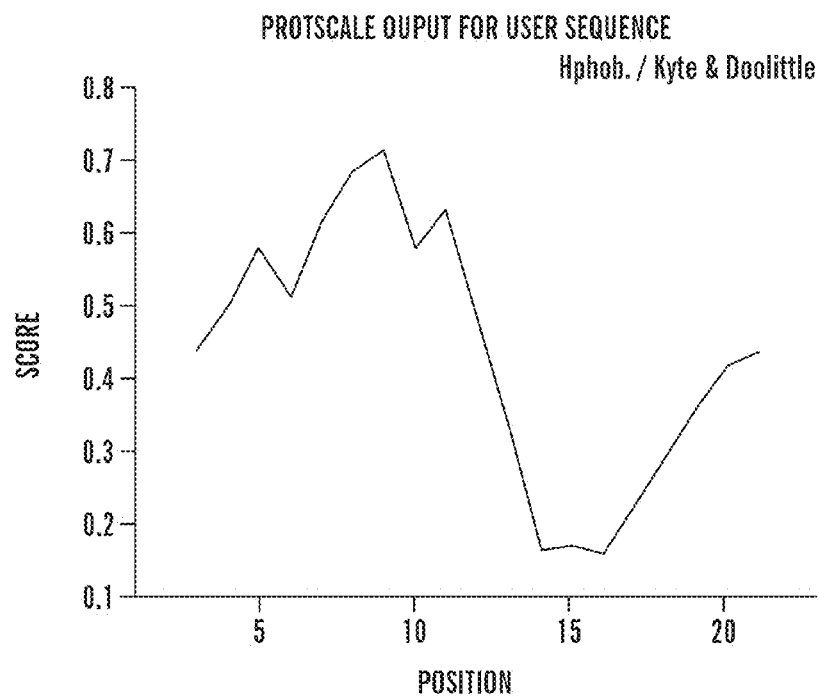
FIGS. 5A-5B are graphs comparing the hydrophobicity of second peptides of the present invention having amino acid sequences of SEQ ID NO:8 and SEQ ID NO:11 by Kyte and Doolittle analysis. Although the peptides have only 23% amino acid homology to each other, the two peptides have very similar hydrophobic character.
Figure 5B:
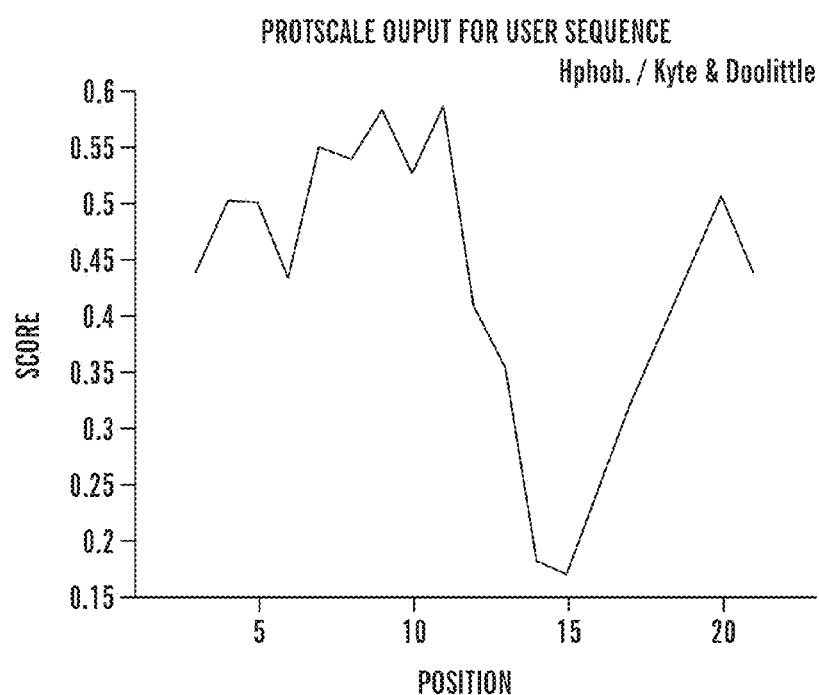
Figure 6A:
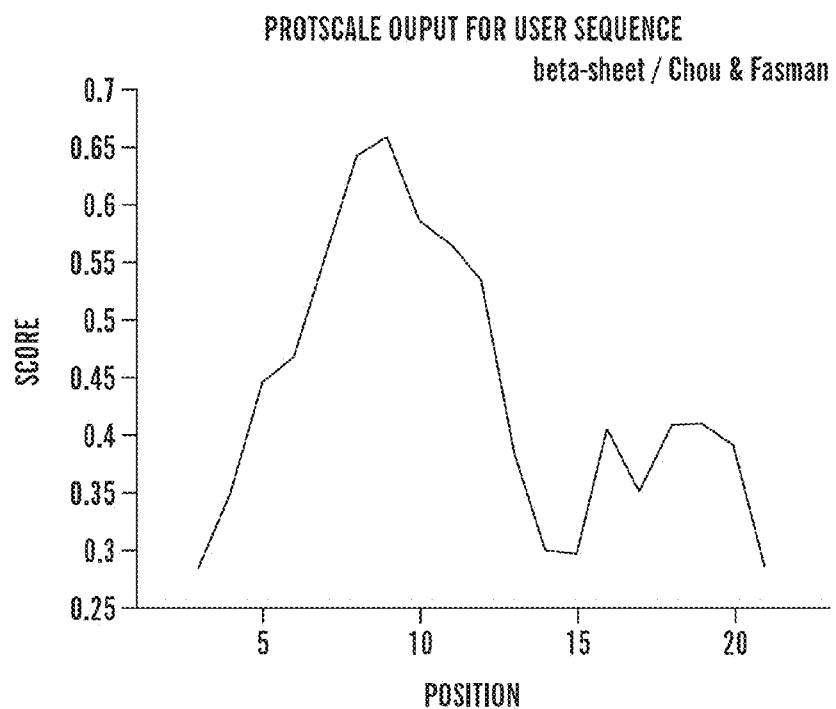
FIGS. 6A-6B are graphs comparing the β-sheet content of second peptides of the present invention having amino acid sequences of SEQ ID NO:8 and SEQ ID NO:11 using Chou-Fasman analysis. Although the peptides have only 23% amino acid sequence homology to each other, the two peptides are structurally similar as demonstrated by their β-sheet content.
Figure 6B:
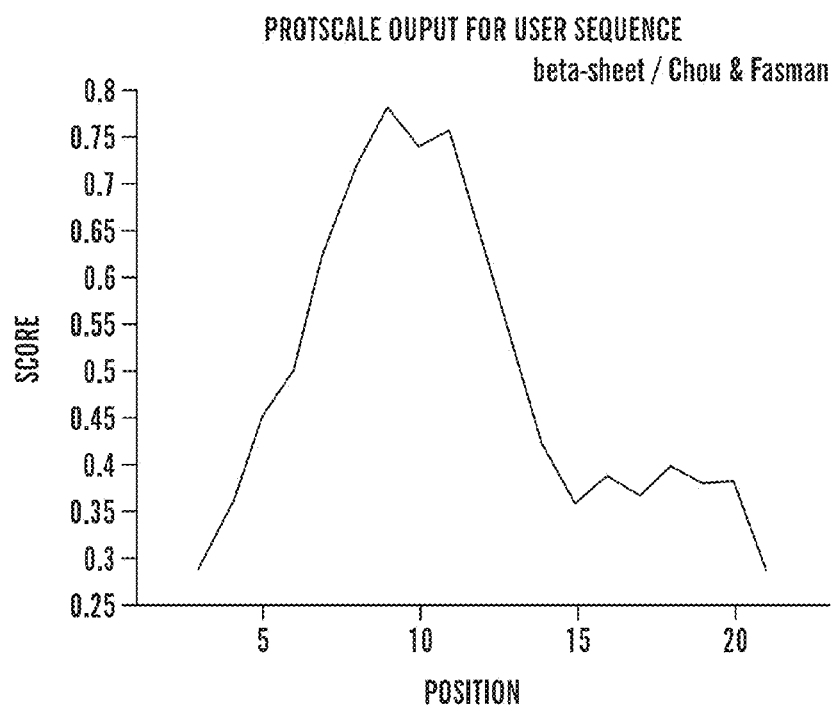

The second peptides of the present invention are designed using the parameters described above to generate peptides that are structurally similar to each other as demonstrated by their hydrophobicity and β-sheet content. FIGS. 4A-4B are graphs showing the similarity in hydrophobicity between the second peptide of SEQ ID NO:8 (FIG. 4A) and the second peptide of SEQ ID NO:11 (FIG. 4B). The second peptide of SEQ ID NO:11 has 23% amino acid sequence homology (three out of thirteen amino acids) to the second peptide of SEQ ID NO:8; however, both peptide fragments have very similar hydrophobic character. This similarity in hydrophobicity was confirmed by Kyte and Doolittle analysis as shown in FIGS. 5A (SEQ ID NO:8) and 5B (SEQ ID NO:11). The similarity in β-sheet content is shown in FIGS. 6A-6B with the β-sheet content of SEQ ID NO:8 shown in FIG. 6A and the β-sheet content of SEQ ID NO:11 shown in FIG. 6B. Despite these two second peptides having very little sequence homology to each other, they are designed using the above parameters to have similar secondary structural characteristics.

In another embodiment, the second peptide is a reverse second peptide. A reverse second peptide is one in which the above described three units of SEQ ID NO:20 are in reverse order (i.e., 3-2-1). Permutations of the second and third units in reverse order are also contemplated (i.e., 2-3-1). This reverse second peptide is also suitable for use in the present invention.

In another embodiment of the present invention, the pharmaceutical agent is a polymer of a fusion peptide. This fusion peptide contains any first peptide or reverse first peptide of the present invention fused to any first peptide, reverse first peptide, second peptide, or reverse second peptide of the present invention as described supra. Similarly, the fusion protein may contain any second peptide or reverse second peptide fused to any second peptide, reverse second peptide, first peptide, or reverse first peptide.

Consistent with the first and second peptide sequence compositions described supra, the first peptide portion of a fusion protein of the present invention incorporates sequentially enhanced units of charged amino acids flanked by non-polar amino acids to generate a very stable and organized beta structure upon polymerization. The second peptide portion of a fusion protein of the present invention contains hydrophobic and complementary hydrophilic segments. The linker residue of the second peptide (i.e., residue $X_8$ of SEQ ID NO:20) facilitates aggregation/polymerization of the second peptide portion.

The fusion peptide of the present invention preferably contains a short linker sequence coupling first peptides to each other or to a second peptide, or coupling second peptides to each other or to a first peptide. Preferred linker sequences include glycine-rich (e.g. $G_{3-5}$) or serine-rich (e.g. GSG, GSGS, GSGSG, $GS_NG$) linker sequences.

In accordance with this aspect of the present invention, an exemplary fusion peptide consisting of the first and second peptides has an amino acid sequence of CSRTVKKNI-IEENGSGSGCFNLFLNSQEKHY (SEQ ID NO:13). Alternatively, the fusion peptide of the present invention has an amino acid sequence of CSRSVKKQIIEENGSGS-GCFQLFLNTQEKHY (SEQ ID NO:15) or CTKTLR-RQLLDDQGSGSGCWQLWIQSNDHKF (SEQ ID NO:17).

Figure 7A:
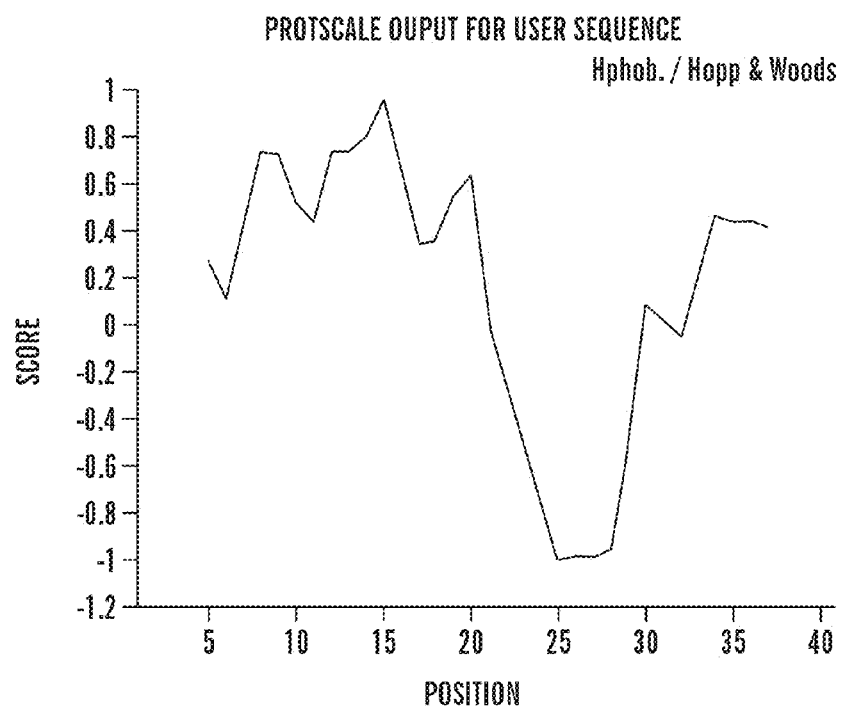
FIGS. 7A-7B are graphs comparing the hydrophobicity of fusion peptides of the present invention having amino acid sequences of SEQ ID NO:13 and SEQ ID NO:17 by Hopp and Woods analysis. These fusion peptides bear little amino acid sequence homology to each other, yet have very similar hydrophobic character.
Figure 7B:
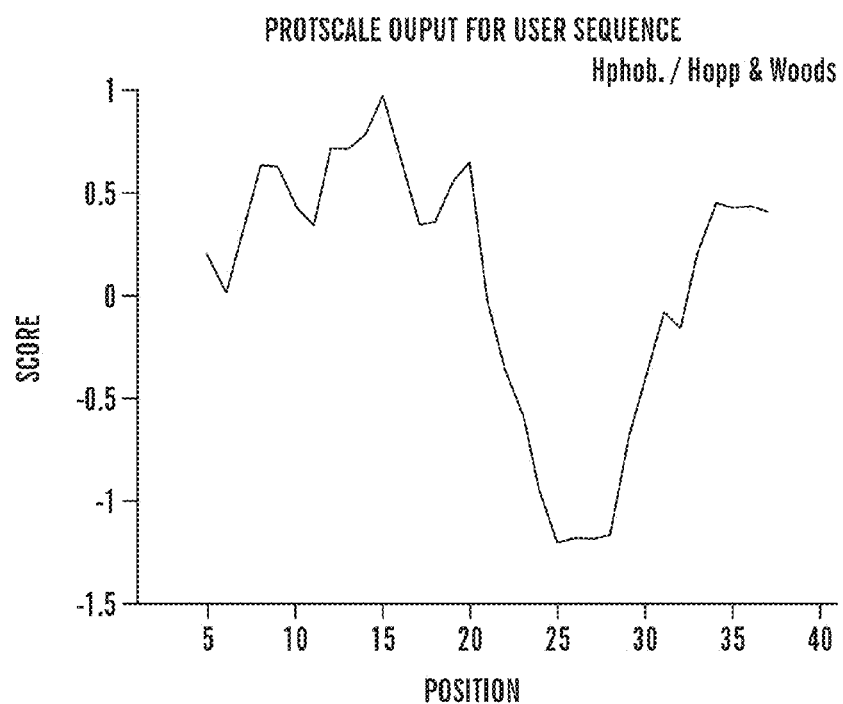
Figure 8A:
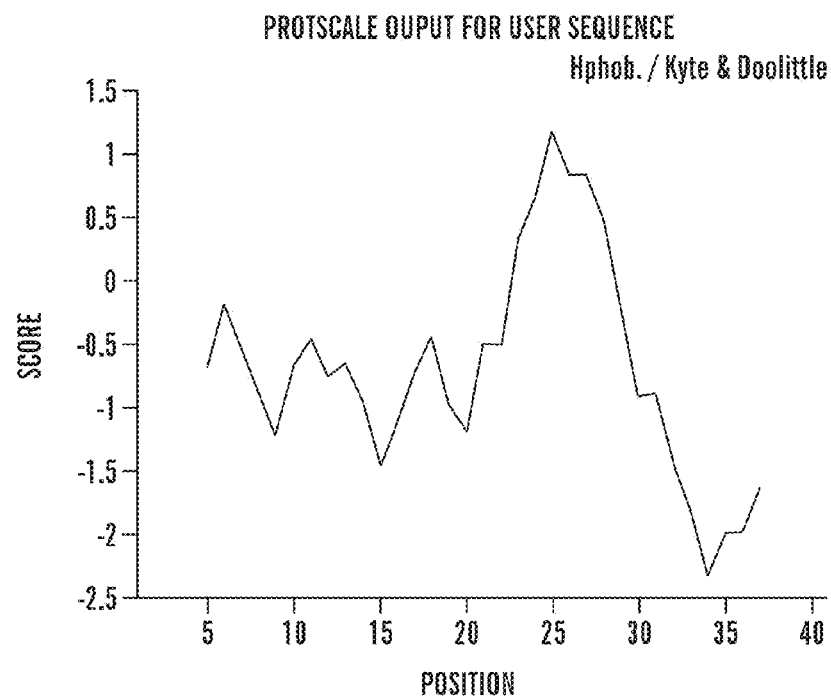
FIGS. 8A-8B are graphs comparing the hydrophobicity of fusion peptides of the present invention having amino acid sequences of SEQ ID NO:13 and SEQ ID NO:17 by Kyte and Doolittle analysis. These fusion peptides bear little amino acid sequence homology to each other, yet have very similar hydrophobic character.
Figure 8B:
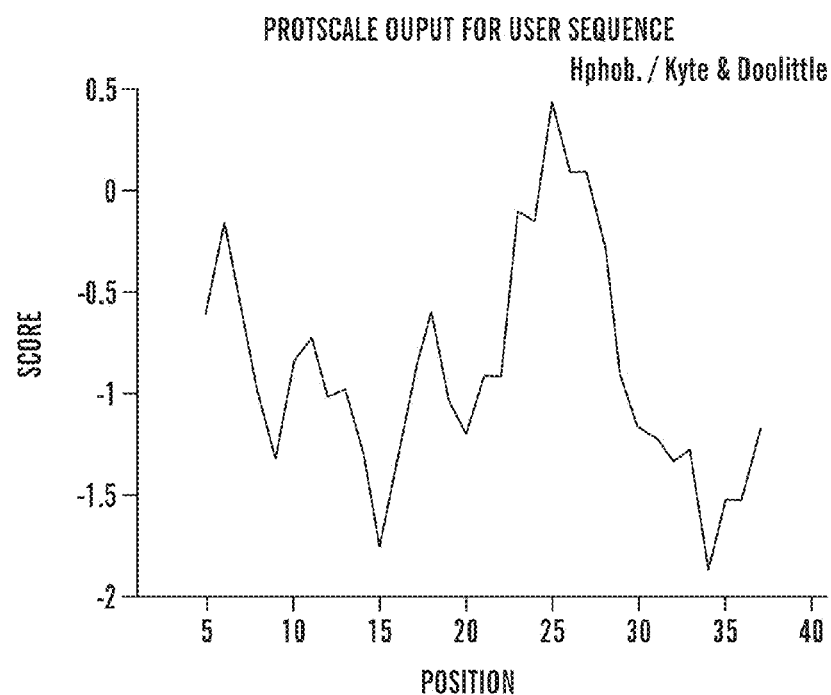
Figure 9A:
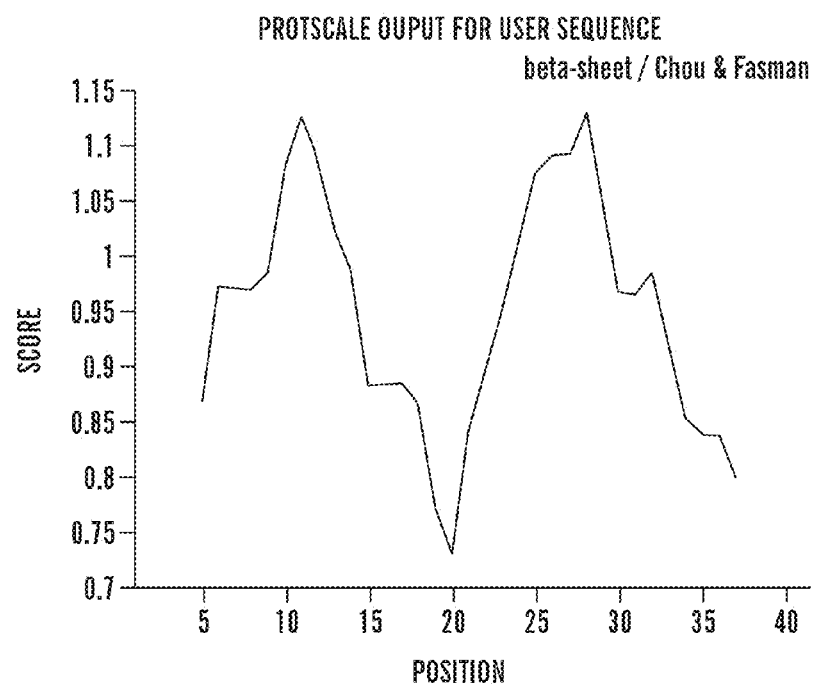
FIGS. 9A-9B are graphs comparing the β-sheet content of fusion peptides of the present invention having amino acid sequences of SEQ ID NO:13 and SEQ ID NO:17 using Chou-Fasman analysis. These fusion peptides bear little amino acid sequence homology to each other, yet have very similar β-sheet content.
Figure 9B:
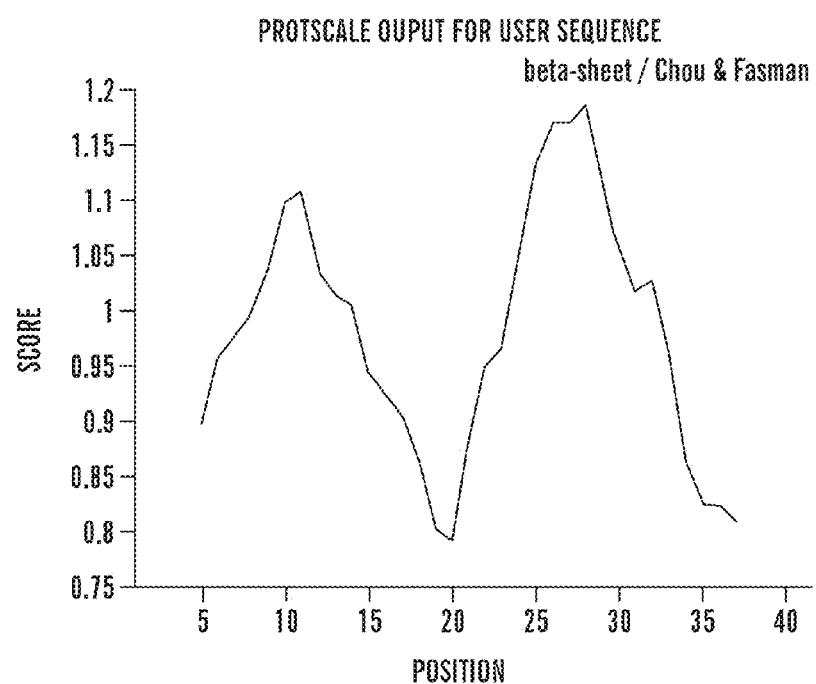

The fusion peptides of the present invention comprise the first and second peptides designed using the parameters described supra. The fusion peptides, like the individual peptides, are structurally very similar to each other as demonstrated by their hydrophobicity and β-sheet content. FIGS. 7A-7B are graphs showing the similarity in hydrophobicity between the fusion peptide of SEQ ID NO:13 (FIG. 7A) and the fusion peptide of SEQ ID NO:17 (FIG. 7B). The fusion peptide of SEQ ID NO:13 comprises of the first peptide of SEQ ID NO:2 fused to the second peptide of SEQ ID NO:8. The fusion peptide of SEQ ID NO:17 comprises of the first peptide of SEQ ID NO:5 fused to the second peptide of SEQ ID NO:11. Accordingly, there is very little amino acid sequence homology between these two fusion peptides, yet their structural similarity is demonstrated by their common hydrophobic character. This similarity in hydrophobicity was confirmed by Kyte and Doolittle analysis as shown in FIGS. 8A (SEQ ID NO:13) and 8B (SEQ ID NO:17). The similarity in β-sheet is shown in FIGS. 9A-9B with the β-sheet content of SEQ ID NO:13 shown in FIG. 9A and the β-sheet content of SEQ ID NO:17 shown in FIG. 9B. Despite the lack of amino acid sequence homology between these two fusion peptides, because the individual peptides are designed following the parameters described above, the fusion peptides share secondary structural characteristics.

In accordance with this aspect of the present invention the pharmaceutical agent may contain a polymer of any one of the first or second peptides or the fusion peptides described supra further linked in-frame to an adjuvant polypeptide. The adjuvant polypeptide can be any adjuvant polypeptide known in the art, including, but not limited to, cholera toxin B, flagellin, human papillomavirus L1 or L2 protein, herpes simplex glycoprotein D (gD), complement C4 binding protein, TL4 ligand, and IL-1β. The first or second peptide or fusion peptide may be linked directly to the adjuvant polypeptide or coupled to the adjuvant by way of a short linker sequence. Suitable linker sequences include glycine or serine-rich linkers described supra or other flexible immunoglobulin linkers as disclosed in U.S. Pat. No. 5,516,637 to Huang et al, which is hereby incorporated by reference in its entirety.

In another embodiment, the pharmaceutical agent may contain a polymer of any one of the first or second peptides or the fusion peptides described supra conjugated to an immunogenic carrier molecule. The immunogenic carrier molecule can be covalently or non-covalently bonded to the peptides or fusion peptides. Suitable immunogenic carrier molecules include, but are not limited to, serum albumins, chicken egg ovalbumin, keyhole limpet hemocyanin, tetanus toxoid, thyroglobulin, pneumococcal capsular polysaccharides, CRM 197, immunoglobulin molecules, alum, and meningococcal outer membrane proteins. Other suitable immunogenic carrier molecules include T-cell epitopes, such as tetanus toxoid (e.g., the P2 and P30 epitopes), Hepatitis B surface antigen, pertussis, toxoid, diphtheria toxoid, measles virus F protein, *Chlamydia trachomatis* major outer membrane protein, *Plasmodium falciparum* circumsporozite T, *P. falciparum* CS antigen, *Schistosoma mansoni* triose phosphate isomersae, *Escherichia coli* TraT, and Influenza virus hemagluttinin (HA). Other suitable immunogenic carrier molecules include promiscuous T helper cell epitopes which are derived from hepatitis B virus, *Bordetella pertussis, Clostridium tetani, Pertusaria trachythallina, E. coli, Chlamydia trachomatis,* Diphtheria, *P. falciparum,* and *Schistosoma mansoni* (see U.S. Pat. No. 6,906,169 to Wang; U.S. Patent Application Publication No. 20030068325 to Wang, and WO/2002/096350 to Wang, which are hereby incorporated by reference in their entirety). Yet other suitable carriers include T-helper cell epitopes derived from tetanus toxin, cholera toxin B, pertussis toxin, diphtheria toxin, measles virus F protein, hepatitis B virus surface antigen, *C. trachomitis* major outer membrane protein, *P. falciparum* circumsporozoite, *S. mansoni* triose phosphate isomerase, or *E. coli* TraT (see WO01/42306 to Chain, which is hereby incorporated by reference in its entirety).

The first and second peptides and the fusion peptides of the present invention can be linked to immunogenic carrier molecules by chemical crosslinking. Techniques for linking a peptide immunogen to an immunogenic carrier molecule include the formation of disulfide linkages using N-succinimidyl-3-(2-pyridyl-thio) propionate (SPDP) and succinimidyl 4-(N-maleimidomethyl)cyclohexane-1-carboxylate (SMCC) (if the peptide lacks a sulfhydryl group, this can be provided by addition of a cysteine residue). These reagents create a disulfide linkage between themselves and peptide cysteine residues on one protein, and an amide linkage through the epsilon-amino on a lysine, or other free amino group in other amino acids. A variety of such disulfide/amide-forming agents are described by Jansen et al., "Immunotoxins: Hybrid Molecules Combining High Specificity and Potent Cytotoxicity," *Immun Rev* 62:185-216 (1982), which is hereby incorporated by reference in its entirety. Other bifunctional coupling agents form a thioether rather than a disulfide linkage. Many of these thio-ether-forming agents are commercially available and include reactive esters of 6-maleimidocaproic acid, 2-bromoacetic acid, 2-iodoacetic acid, and 4-(N-maleimido-methyl)cyclohexane-1-carboxylic acid. The carboxyl groups can be activated by combining them with succinimide or 1-hydroxyl-2-nitro-4-sulfonic acid, sodium salt.

The first and second peptides and the fusion peptides comprising the polymers of the pharmaceutical agent can be made using standard techniques of chemical synthesis which are well known in the art (see e.g., SYNTHETIC PEPTIDES: A USERS GUIDE 93-210 (Gregory A. Grant ed., 1992), which is hereby incorporated by reference in its entirety).

Polymerization of the first or second peptides or the fusion peptides alone or conjugated to an adjuvant polypeptide or immunogenic carrier molecule can be achieved using standard techniques known in the art. As described herein, the first and second peptides or fusion peptides can be polymerized by a reaction with a cross linking reagent. Suitable cross-linking reagents include, but are not limited to glutaraldehyde and 1-Ethyl-3-[3-dimethylaminopropyl]carbodiimide hydrochloride (EDC). Alternatively, the peptides or fusion peptides can be polymerized by cysteine oxidation induced disulfide cross linking.

Another aspect of the present invention is directed to a pharmaceutical composition containing the pharmaceutical agent described supra and a pharmaceutically acceptable carrier.

The pharmaceutical composition of the present invention may contain a single pharmaceutical agent, i.e. a homopolymer of first or second peptides or the fusion peptides. Alternatively, the pharmaceutical composition may contain a mixture of one or more pharmaceutical agents, i.e. heteropolymer of the first and second peptides and/or the fusion peptides.

The pharmaceutical composition of the present invention can further contain, in addition to peptide polymers, other pharmaceutically acceptable components (see REMINGTON'S PHARMACEUTICAL SCIENCE (19th ed., 1995), which is hereby incorporated by reference in its entirety). The incorporation of such pharmaceutically acceptable components depends on the intended mode of administration and therapeutic application of the pharmaceutical composition. Typically, however, the pharmaceutical composition will include a pharmaceutically-acceptable, non-toxic carrier or diluent, which are defined as vehicles commonly used to formulate pharmaceutical compositions for animal or human administration. The diluent is selected so as not to affect the biological activity of the composition. Exemplary carriers or diluents include distilled water, physiological phosphate-buffered saline, Ringer's solutions, dextrose solution, and Hank's solution.

Pharmaceutical compositions can also include large, slowly metabolized macromolecules such as proteins, polysaccharides such as chitosan, polylactic acids, polyglycolic acids and copolymers (such as latex functionalized sepharose, agarose, cellulose), polymeric amino acids, amino acid copolymers, and lipid aggregates (such as oil droplets or liposomes).

The pharmaceutical composition of the present invention can further contain an adjuvant. One class of preferred adjuvants is aluminum salts, such as aluminum hydroxide, aluminum phosphate, or aluminum sulfate. Such adjuvants can be used with or without other specific immunostimulating agents such as MPL or 3-DMP, QS-21, flagellin, polymeric or monomeric amino acids such as polyglutamic acid or polylysine, or pluronic polyols. Oil-in-water emulsion formulations are also suitable adjuvants that can be used with or without other specific immunostimulating agents such as muramyl peptides (e.g., N-acetylmuramyl-L-threonyl-D-isoglutamine (thr-MDP), N-acetyl-normuramyl-L-alanyl-D-isoglutamine (nor-MDP), N-acetylmuramyl-L-alanyl-D-isoglutaminyl-L-alanine-2-(1'-2'dipalmitoyl-sn-1-glycero-3-hydroxyphosphoryloxy)-ethylamine (MTP-PE), N-acetylglucsaminyl-N-acetylmuramyl-L-Al-D-isoglu-L-Ala-dipalmitoxy propylamide (DTP-DPP) Theramide™, or other bacterial cell wall components). A suitable oil-in-water emulsion is MF59 (containing 5% Squalene, 0.5% Tween 80, and 0.5% Span 85 (optionally containing various amounts of MTP-PE) formulated into submicron particles using a microfluidizer such as Model 110Y microfluidizer (Microfluidics, Newton Mass.) as described in WO90/14837 to Van Nest et al., which is hereby incorporated by reference in its entirety. Other suitable oil-in-water emulsions include SAF (containing 10% Squalene, 0.4% Tween 80, 5% pluronic-blocked polymer L121, and thr-MDP, either microfluidized into a submicron emulsion or vortexed to generate a larger particle size emulsion) and Ribi™ adjuvant system (RAS; containing 2% squalene, 0.2% Tween 80, and one or more bacterial cell wall components). Another class of preferred adjuvants is saponin adjuvants, such as Stimulon™ (QS-21) or particles generated therefrom such as ISCOMs (immunostimulating complexes) and ISCOMATRIX. Other suitable adjuvants include incomplete or complete Freund's Adjuvant (IFA), cytokines, such as interleukins (IL-1, IL-2, and IL-12), macrophage colony stimulating factor (M-CSF), lysolecithin, tumor necrosis factor (TNF), and liposome polycation DNA particles. Such adjuvants are generally available from commercial sources.

In another embodiment of the present invention, the pharmaceutical composition further includes a delivery vehicle. Suitable delivery vehicles include, but are not limited to biodegradable microspheres, microparticles, nanoparticles, liposomes, collagen minipellets, and cochleates.

In a preferred embodiment of this aspect of the invention, the pharmaceutical agent includes a mucosal delivery system. A preferred mucosal delivery system consists of attenuated *Salmonella* (e.g., *Salmonella typhimurium*) with a non-toxic fragment C of tetanus toxin (TetC) or glutathione S-transferase (GST). Methods of mucosal vaccination via oral administration of *S. typhimurium* are described in Goni et al., "Mucosal Vaccination Delays or Prevents Prion Infection via an Oral Route," *Neuroscience* 133:413-21 (2005), and Goni et al., "High Titers of Mucosal and Systemic Anti-PrP Antibodies Abrogate Oral Prion Infection in Mucosal-Vaccinated Mice," *Neuroscience* 153:679-686 (2008), which are hereby incorporated by reference in their entirety.

Another aspect of the present invention relates to a method of inducing an immune response against an amyloidogenic protein or peptide in a subject. This method involves administering to the subject a pharmaceutical agent of the present invention or a pharmaceutical composition containing a polymerized first or second peptide or fusion peptide as described supra under conditions effective to induce an immune response against the amyloidogenic protein or peptide in the subject. In a preferred embodiment of this aspect of the present invention, a subject in need of an immune response against an amyloidogenic protein or peptide is selected prior to administering the pharmaceutical agent.

As used herein, an "amyloid protein" or "amyloidogenic protein" are used interchangeably to encompasses any insoluble fibrous protein/peptide aggregate that is deposited intra- or extracellularly within the body. Amyloidogenic protein/peptide deposition may be organ-specific (e.g., central nervous system, pancreas, etc.) or systemic. In accordance with this aspect of the invention, amyloidogenic proteins/peptides subject to deposition include beta protein precursor, prion and prion proteins, α-synuclein, tau, ABri precursor protein, ADan precursor protein, amylin, apolipoprotein AI, apolipoprotein AII, lyzozyme, cystatin C, gelsolin, protein, atrial natriuretic factor, calcitonin, keratoepithelin, lactoferrin, immunoglobulin light chains, transthyretin, A amyloidosis, β2-microglobulin, immunoglobulin heavy chains, fibrinogen alpha chains, prolactin, keratin, and medin. Amyloid deposition may occur as its own entity or as a result of another illness (e.g., multiple myeloma, chronic infection, or chronic inflammatory disease).

In accordance with this aspect of the present invention, an immune response is the development of a beneficial humoral (antibody mediated) and/or a cellular (mediated by antigen-specific T cells or their secretion products) response directed against the polymerized peptide or fusion peptide of the pharmaceutical composition. Such a response is an active response induced by administration of the immunogenic polymerized peptide agent and represents a therapeutic means for clearing or removing amyloid protein deposits from the body of the subject.

The presence of a humoral immunological response can be determined and monitored by testing a biological sample (e.g., blood, plasma, serum, urine, saliva feces, CSF or lymph fluid) from the subject for the presence of antibodies directed to the immunogenic component of the administered pharmaceutical composition. Methods for detecting antibodies in a biological sample are well known in the art, e.g., ELISA, Dot blots, SDS-PAGE gels or ELISPOT. The presence of a cell-mediated immunological response can be determined by proliferation assays (CD4+ T cells) or CTL (cytotoxic T lymphocyte) assays which are readily known in the art.

The present invention is further directed to a method of preventing and/or treating a condition mediated by an amyloidogenic protein or peptide in a subject. This method involves administering to the subject, a pharmaceutical agent of the present invention or a pharmaceutical composition containing a polymerized first or second peptide or fusion peptide as described supra. The pharmaceutical agent or composition is administered under conditions effective to treat the condition mediated by the amyloidogenic protein or peptide in the subject. In a preferred embodiment of this aspect of the present invention, a subject at risk of having or having a condition mediated by an amyloidogenic protein or peptide is selected prior to administering the pharmaceutical agent.

Conditions or diseases associated with, or resulting from, the deposition of amyloidogenic proteins or peptides include, but are not limited to, Alzheimer's disease, diffuse Lewy body disease, Down syndrome, fronto-temporal dementia, Parkinson's disease, hereditary cerebral hemorrhage with amyloidosis, kuru, Creutzfeldt-Jakob disease, Gerstmann-Straussler-Scheinker disease, fatal familial insomnia, British familial dementia, Danish familial dementia, familial corneal amyloidosis, Familial corneal dystrophies, medullary thyroid carcinoma, insulinoma, type 2 diabetes, isolated atrial amyloidosis, pituitary amyloidosis, aortic amyloidosis, plasma cell disorders, familial amyloidosis, senile cardiac amyloidosis, inflammation-associated amyloidosis, familial Mediterranean fever, dialysis-associated amyloidosis, systemic amyloidosis, and familial systemic amyloidosis. In accordance with this aspect of the present invention, administration of the pharmaceutical agent or composition is effective to stimulate an immune response in the subject, resulting in the reduction or clearance of the amyloidogenic protein that is causing or exacerbating the aforementioned disease conditions.

Preliminary vaccination studies using the polymerized first peptide of SEQ ID NO:2 are described infra in the Examples. Vaccination with any of the other polymerized first peptides (e.g., SEQ ID NOs: 3 and 5), second peptides (e.g., SEQ ID NOs: 6, 7, and 9), or the fusion peptides (e.g., SEQ ID NOs: 11, 13, and 15) described supra is expected to induce a conformational immune response to both aggregated/oligomeric Aβ, neurofibrillary tangles (NFTs), and prion proteins (PrP$^{Sc}$), similar to that observed with the polymerized first peptide of SEQ ID NO:2. Vaccinations studies using polymerized first or second peptides or fusion peptides of the present invention are described in more detail below.

The first and second peptides and fusion peptides will be custom synthesized. Cross-linking and polymerization of the amyloid peptides will be achieved by an optimized reaction with glutaraldehyde or other standard cross-linking reagents, such as 1-Ethyl-3-[3-dimethylaminopropyl]carbodiimide Hydrochloride (EDC). The aggregated amyloid peptides will be characterized by SDS-PAGE, electron microscopy and circular dichroism using previously published methods (Sadowski et al., "Blocking the ApolipoproteinE/Amyloid β Interaction Reduces the Parenchymal and Vascular Amyloid-β Deposition and Prevents Memory Deficit in AD Transgenic Mice," *Proc Natl Acad Sci (USA)* 103:18787-18792 (2006), which is hereby incorporated by reference in its entirety).

Immunizations with the polymerized peptide immunogens will be performed in suitable animal models, e.g., wild-type laboratory mice, with 10 animals per protocol. Various adjuvant protocols will be tested in addition to the alum adjuvant described infra. Specifically, Freund's adjuvant will be administered following published protocols (Sigurdsson et al., "An Attenuated Immune Response Is Sufficient To Enhance Cognition in an Alzheimer's Disease Mouse Model Immunized With Amyloid-β Derivatives," *J Neurosci* 24:6277-6282 (2004) and Sigurdsson et al., "Immunization With a Nontoxic/Nonfibrillar Amyloid-β Homologous Peptide Reduces Alzheimer's Disease Associated Pathology in Transgenic Mice," *Amer J Pathol* 159:439-447 (2001), which are hereby incorporated by reference in their entirety) and the use of cholera toxin B (CTB) subunit as an adjuvant using an oral route for immunization will also be tested. Cholera toxin is a well known and powerful adjuvant that augments the local (gastrointestinal) and systemic serum antibody response via a Th2 cell dependent pathway to co-administered antigens (Gelinas et al., "Immunotherapy for Alzheimer's Disease," *Proc Natl Acad Sci (USA)* 101:14657-14662 (2004), which is hereby incorporated by reference in its entirety).

Mucosal immunization is a highly effective way to treat both AD and prion related pathology (Goni et al., "Mucosal Vaccination Delays Or Prevents Prion Infection Via an Oral Route," *Neurosci* 133:413-421 (2005), and Goni et al., "High Titers of Mucosal and Systemic Anti-PrP Antibodies Abrogates Oral Prion Infection in Mucosal Vaccinated Mice," *Neurosci* 153:679-686 (2008), which are hereby incorporated by reference in their entirety). Accordingly, immunogens will be diluted in 0.2M NaHCO$_3$, pH 8.3, and 0.5 ml of the solutions will be introduced by intragastric intubation. Immunogenic solutions will contain 50 µg of immunogen alone or immunogen-CTB conjugate with or without free CTB as adjuvant; 50 µg of immunogen or immunogen-CTB conjugate with 30 µg of free CTB; and 150 µg of immunogen (unconjugated) with or without 5 µg of CT. Bleeds from immunized mice will be used to establish antibody titers to aggregated first peptide, aggregated second peptide, PrP$^{Sc}$, PHF, aggregated Aβ1-42 and Aβ1-40. Titers will be determined by serial dilutions of plasma applied to microtiter plates coated overnight with recombinant prion protein (PrP) at 5-10 ng/well, as previously published (Goni et al., "Mucosal Vaccination Delays Or Prevents Prion Infection Via an Oral Route," *Neurosci* 133: 413-421 (2005); Goni et al., "High Titers of Mucosal and Systemic Anti-PrP Antibodies Abrogates Oral Prion Infection in Mucosal Vaccinated Mice," *Neurosci* 153:679-686 (2008); and Sigurdsson et al., "Vaccination Delays the Onset of Prion Disease in Mice," *American J Pathol* 161:13-17 (2002), which are hereby incorporated by reference in their entirety). The titer, defined as the dilution yielding 50% of the maximum signal, will be detected by a goat anti-mouse IgG linked to horseradish peroxidase with TMB as substrate. Oligomers/aggregates will be prepared as previously reported (Golabek et al., "The Interaction Between Apolipoprotein E and Alzheimer's Amyloid β-Peptide Is Dependent On β-Peptide Conformation," *J Biol Chem* 271:10602-10606 (1996) and Barghorn et al., "Globular Amyloid Beta-Peptide Oligomer—a Homogenous and Stable Neuropathological Protein in Alzheimer's Disease," *J Neurochem* 95:834-847 (2005), which are hereby incorporated by reference in their entirety). The secondary structure of the polymerized immunogens will be evaluated using circular dichroism (CD) and electron microscopy as described previously (Sadowski et al., "Blocking the ApolipoproteinE/Amyloid β Interaction Reduces the Parenchymal and Vascular Amyloid-β Deposition and Prevents Memory Deficit in AD Transgenic Mice," *Proc Natl Acad Sci* (*USA*) 103:18787-18792 (2006), which is hereby incorporated by reference in its entirety). The aggregated Aβ1-42 preparations typically have an ~80% β-sheet structure as measured by CD.

Following optimization of peptide polymerization and immunization, vaccination protocols will be repeated in one or more animal models of Alzheimer's disease or other amyloid disease. Homozygous 3×Tg mice, a suitable animal model of Alzheimer's disease, will be vaccinated with polymerized first or second peptide or fusion peptide immunogens, Tau370-408[P-Ser$_{396,404}$], Aβ1-42, or vehicle, from the age of 10 months to 17 months. The Aβ1-42 and Tau370-408 [P-Ser$_{396,404}$] vaccinated animals will serve as controls where only Aβ or tau alone is targeted for immunotherapy versus the first and second polymerized peptide groups where both Aβ and tau pathology will be targeted.

Behavioral studies of vaccinated and control mice will be performed during the final month of treatment. In addition to the radial arm maze analysis, locomotor activity and spatial learning and memory using the Barnes maze will be assessed (Sigurdsson et al., "An Attenuated Immune Response Is Sufficient To Enhance Cognition in an Alzheimer's Disease Mouse Model Immunized With Amyloid-β Derivatives," *J Neurosci* 24:6277-6282 (2004) and Sadowski et al., "Amyloid-β Deposition Is Associated With Decreased Hippocampal Glucose Metabolism and Spatial Memory Impairment in APP/PS1 Mice," *J Neuropath Exp Neurol* 63:418-428 (2004), which are hereby incorporated by reference in their entirety). Amyloid and tau burden in brain parenchyma and cerebral blood vessels (in the case of Aβ) of vaccinated and control mice will also be determined. Amyloid burden quantitation, including biochemical levels for both soluble and insoluble Aβ, as well as, Aβ oligomer levels will be performed following previously published protocols (Sadowski et al., "Blocking the ApolipoproteinE/Amyloid β Interaction Reduces the Parenchymal and Vascular Amyloid-β Deposition and Prevents Memory Deficit in AD Transgenic Mice," *Proc Natl Acad Sci* (*USA*) 103:18787-18792 (2006) and Scholtzova et al., "An NMDA Receptor Antagonist Leads To Behavioral Improvement and Amyloid Reduction in Alzheimer's Disease Model Transgenic Mice Shown by Micro-Magnetic Resonance Imaging," *J Neurosci Res* 86:2784-2791 (2008), which are hereby incorporated by reference in their entirety). The presence of intracerebral microhemorrhages will be assessed using Prussian Blue stain, which labels hemosiderin that deposits around blood vessels from extravenous hemoglobin, providing an indication of hemorrhage (Sadowski et al., "Blocking the ApolipoproteinE/Amyloid β Interaction Reduces the Parenchymal and Vascular Amyloid-β Deposition and Prevents Memory Deficit in AD Transgenic Mice," *Proc Natl Acad Sci* (*USA*) 103:18787-18792 (2006), which is hereby incorporated by reference in its entirety).

Histological measurements will be correlated with Aβ peptide, total tau, and phosphorylated tau brain levels both in the soluble and insoluble fractions. Signs of toxicity will be monitored daily with evaluation of five aspects of the animals' condition as described previously (Sigurdsson et al., "An Attenuated Immune Response Is Sufficient To Enhance Cognition in an Alzheimer's Disease Mouse Model Immunized With Amyloid-β Derivatives," *J Neurosci* 24:6277-6282 (2004), which is hereby incorporated by reference in its entirety).

In the treated and control mice, the Th-1/Th-2/Th-17 profile will be monitored by assessing the profile and magnitude of cytokine production, as well as specific antibody titers. Antibody titers to the polymerized first or second peptide, aggregated PrP$^{sc}$, aggregated Aβ42, aggregated Aβ40, and PHF will be determined by ELISA. In addition plasma will be tested for its immunoreactivity to amyloid plaques and NFT in human AD brain sections.

The production of type 1/type 2/type 17 cytokines will also be investigated on cells stimulated in vitro with aggregated first and second peptides, PrP$^{Sc}$, or Aβ42 oligomer immunogens. The immunogens will be added in triplicate in volumes ranging between 5 and 20 µl, and at different time points after stimulations, cell supernatants will be collected and analyzed using either the Cytometric Bead Array Th1/Th2 cytokine kit (CBA, BD Biosciences) or an ELISA with a specific pair of antibodies for determination of IL-17 (Rial et al., "Intranasal Immunization With a Colloid-Formulated Bacterial Extract Induces an Acute Inflammatory Response in the Lungs and Elicits Specific Immune Responses," *Infection and Immunity* 72:2679-2688 (2004), which is hereby incorporated by reference in its entirety). The CBA system allows the quantification of an array of Th1/Th2 cytokines in a small volume (25-50 µl) sample.

The local antibody response will be assessed by enumerating antibody secreting cells (ASC) on Peyer's Patches (PP) and mesenteric lymph nodes (MLN) by ELISPOT as previously described (Rial et al., "Intranasal Immunization With a Colloid-Formulated Bacterial Extract Induces an Acute Inflammatory Response in the Lungs and Elicits Specific Immune Responses," *Infection and Immunity* 72:2679-2688 (2004), which is hereby incorporated by reference in its entirety). ELISPOT analysis will be used to enumerate the frequency of cells reactive to $PrP^C$, $PrP^{Sc}$ or oligomeric Aβ42, producing selected cytokines. Cytokine concentrations will be evaluated in PP, MLN, and spleen cell cultures upon in vitro antigen stimulation. Functional assays will include $CD4^+$ T cell responses monitored by proliferation assay.

For monoclonal antibody production, cells from the spleens, MLN or Peyer's patches of mice immunized with a first or second peptide or fusion peptide will be fused with a SP2/0 myeloma cells or any other suitable partner to create hybridomas. ELISA will be used to screen for potential anti-β-sheet conformational monoclonal antibodies as described above. Positive clones will be isotyped using an immunopure monoclonal antibody isotyping kit (Pierce, Rockford, Ill.).

A second aspect of the present invention is directed to an isolated antibody or binding portion thereof having antigenic specificity for an epitope of a polymerized peptide. The polymerized peptide is selected from the group consisting of (i) a polymer of a first peptide comprising the amino acid sequence $X_{1a}X_{2a}X_{3a}X_{4a}X_{5a}X_{6a}X_{7a}X_{8a}X_{9a}X_{10a}X_{11a}X_{12a}X_{13a}$ (SEQ ID NO: 19), wherein $X_{1a}$ is C, M, S, or G; $X_{2a}$ is T, S, or C; $X_{3a}$ is K, R, or H; $X_{4a}$ is S, T, or C; $X_{5a}$ is V, I, or L; $X_{6a}$ is R, K, or H; $X_{7a}$ is R, K, or H; $X_{8a}$ is Q or N; $X_{9a}$ is L, I, or V; $X_{10a}$ is L, I, or V; $X_{11a}$ is D or E; $X_{12a}$ is D or E; $X_{13a}$ is Q or N; (ii) a polymer of a second peptide comprising the amino acid sequence $X_{1b}X_{2b}X_{3b}X_{4b}X_{5b}X_{6b}X_{7b}X_{8b}X_{9b}X_{10b}X_{11b}X_{12b}X_{13b}$ (SEQ ID NO: 20), wherein $X_{1b}$ is C, M, S, or G; $X_{2b}$ is F, Y, or W; $X_{3b}$ is Q or N; $X_{4b}$ is I, L, or V; $X_{5b}$ is F, Y, or W; $X_{6b}$ is I, L, or V; $X_{7b}$ is Q or N; $X_{8b}$ is T, S, or C; $X_{9b}$ is N or Q; $X_{10b}$ is D or E; $X_{11b}$ is R, K, or H; $X_{12b}$ is H, R, or K; $X_{13b}$ is Y, W, or F; and (iii) a polymer of a fusion peptide comprising the first and/or second peptides.

As used herein, "epitope" refers to the antigenic determinant of the polymerized first or second peptide or fusion peptide of the present invention that is recognized by the isolated antibody. The epitope recognized by the antibody of the present invention may be a linear epitope, i.e. the primary structure of the amino acid sequence of the first or second peptides or fusion peptides. Preferably, the linear epitope recognized by the isolated antibody of the present invention does not have amino acid sequence homology to a non-amyloid protein. Alternatively, the epitope recognized by the isolated antibody of the present invention is a non-linear or conformational epitope, i.e. the tertiary or quaternary structure of a polymerized first or second peptide or fusion peptide. More preferably, the non-linear or conformational epitope recognized by the isolated antibody of the present invention is a conformational epitope that is common or shared with one or more, or all, amyloidogenic proteins. Accordingly, the isolated antibody of the present invention has antigenic specificity for a shared conformational epitope common to all amyloidogenic proteins known in the art.

An isolated antibody of the present invention encompasses any immunoglobulin molecule that specifically binds to a conformational epitope shared by a polymerized first or second peptide or fusion peptide and one or more other amyloidogenic proteins. As used herein, the term "antibody" is meant to include intact immunoglobulins derived from natural sources or from recombinant sources, as well as immunoreactive portions (i.e., antigen binding portions) of intact immunoglobulins. The antibodies of the present invention may exist in a variety of forms including, for example, polyclonal antibodies, monoclonal antibodies, intracellular antibodies ("intrabodies"), antibody fragments (e.g. Fv, Fab and F(ab)2), as well as single chain antibodies (scFv), chimeric antibodies and humanized antibodies (Ed Harlow and David Lane, USING ANTIBODIES: A LABORATORY MANUAL (Cold Spring Harbor Laboratory Press, 1999); Houston et al., "Protein Engineering of Antibody Binding Sites: Recovery of Specific Activity in an Anti-Digoxin Single-Chain Fv Analogue Produced in *Escherichia coli*," *Proc Natl Acad Sci USA* 85:5879-5883 (1988); Bird et al, "Single-Chain Antigen-Binding Proteins," *Science* 242:423-426 (1988)). In a preferred embodiment, the antibody of the present invention is the monoclonal 3D6 antibody described infra, or comprises an active antigen binding portion of the 3D6 antibody.

Antibodies of the present invention may also be synthetic antibodies. A synthetic antibody is an antibody which is generated using recombinant DNA technology, such as, for example, an antibody expressed by a bacteriophage. Alternatively, the synthetic antibody is generated by the synthesis of a DNA molecule encoding and expressing the antibody of the invention or the synthesis of an amino acid specifying the antibody, where the DNA or amino acid sequence has been obtained using synthetic DNA or amino acid sequence technology which is available and well known in the art.

Methods for monoclonal antibody production may be carried out using the techniques described herein or other well-known in the art (MONOCLONAL ANTIBODIES—PRODUCTION, ENGINEERING AND CLINICAL APPLICATIONS (Mary A. Ritter and Heather M. Ladyman eds., 1995), which is hereby incorporated by reference in its entirety). Generally, the process involves obtaining immune cells (lymphocytes) from the spleen of a mammal which has been previously immunized with the antigen of interest (i.e., a polymerized first or second peptide or fusion peptide) either in vivo or in vitro. Exemplary first and second peptides and fusion peptides are described supra.

The antibody-secreting lymphocytes are then fused with myeloma cells or transformed cells, which are capable of replicating indefinitely in cell culture, thereby producing an immortal, immunoglobulin-secreting cell line. Fusion with mammalian myeloma cells or other fusion partners capable of replicating indefinitely in cell culture is achieved by standard and well-known techniques, for example, by using polyethylene glycol (PEG) or other fusing agents (Milstein and Kohler, "Derivation of Specific Antibody-Producing Tissue Culture and Tumor Lines by Cell Fusion," *Eur J Immunol* 6:511 (1976), which is hereby incorporated by reference in its entirety). The immortal cell line, which is preferably murine, but may also be derived from cells of other mammalian species, is selected to be deficient in enzymes necessary for the utilization of certain nutrients, to be capable of rapid growth, and have good fusion capability. The resulting fused cells, or hybridomas, are cultured, and the resulting colonies screened for the production of the desired monoclonal antibodies. Colonies producing such antibodies are cloned, and grown either in vivo or in vitro to produce large quantities of antibody.

Alternatively monoclonal antibodies can be made using recombinant DNA methods as described in U.S. Pat. No. 4,816,567 to Cabilly et al, which is hereby incorporated by reference in its entirety. The polynucleotides encoding a monoclonal antibody are isolated from mature B-cells or hybridoma cells, for example, by RT-PCR using oligonucleotide primers that specifically amplify the genes encoding the heavy and light chains of the antibody. The isolated polynucleotides encoding the heavy and light chains are then cloned into suitable expression vectors, which when transfected into host cells such as *E. coli* cells, simian COS cells, Chinese hamster ovary (CHO) cells, or myeloma cells that do not otherwise produce immunoglobulin protein, monoclonal antibodies are generated by the host cells. Also, recombinant monoclonal antibodies or fragments thereof of the desired species can be isolated from phage display libraries (McCafferty et al., "Phage Antibodies: Filamentous Phage Displaying Antibody Variable Domains," *Nature* 348:552-554 (1990); Clackson et al., "Making Antibody Fragments using Phage Display Libraries," *Nature* 352:624-628 (1991); and Marks et al., "By-Passing Immunization. Human Antibodies from V-Gene Libraries Displayed on Phage," *J. Mol. Biol.* 222:581-597 (1991), which are hereby incorporated by reference in their entirety).

The polynucleotide(s) encoding a monoclonal antibody can further be modified using recombinant DNA technology to generate alternative antibodies. For example, the constant domains of the light and heavy chains of a mouse monoclonal antibody can be substituted for those regions of a human antibody to generate a chimeric antibody. Alternatively, the constant domains of the light and heavy chains of a mouse monoclonal antibody can be substituted for a non-immunoglobulin polypeptide to generate a fusion antibody. In other embodiments, the constant regions are truncated or removed to generate the desired antibody fragment of a monoclonal antibody. Furthermore, site-directed or high-density mutagenesis of the variable region can be used to optimize specificity and affinity of a monoclonal antibody.

The monoclonal antibody of the present invention can be a humanized antibody. Humanized antibodies are antibodies that contain minimal sequences from non-human (e.g., murine) antibodies within the variable regions. Such antibodies are used therapeutically to reduce antigenicity and human anti-mouse antibody responses when administered to a human subject. In practice, humanized antibodies are typically human antibodies with minimal to no non-human sequences. A human antibody is an antibody produced by a human or an antibody having an amino acid sequence corresponding to an antibody produced by a human.

An antibody can be humanized by substituting the complementarity determining region (CDR) of a human antibody with that of a non-human antibody (e.g., mouse, rat, rabbit, hamster, etc.) having the desired specificity, affinity, and capability (Jones et al., "Replacing the Complementarity-Determining Regions in a Human Antibody With Those From a Mouse," *Nature* 321:522-525 (1986); Riechmann et al., "Reshaping Human Antibodies for Therapy," *Nature* 332: 323-327 (1988); Verhoeyen et al., "Reshaping Human Antibodies: Grafting an Antilysozyme Activity," *Science* 239: 1534-1536 (1988), which are hereby incorporated by reference in their entirety). The humanized antibody can be further modified by the substitution of additional residues either in the Fv framework region and/or within the replaced non-human residues to refine and optimize antibody specificity, affinity, and/or capability.

Human antibodies can be produced using various techniques known in the art. Immortalized human B lymphocytes immunized in vitro or isolated from an immunized individual that produce an antibody directed against a target antigen can be generated (See e.g., Reisfeld et al., MONOCLONAL ANTIBODIES AND CANCER THERAPY 77 (Alan R. Liss ed., 1985) and U.S. Pat. No. 5,750,373 to Garrard, which are hereby incorporated by reference in their entirety). Also, the human antibody can be selected from a phage library, where that phage library expresses human antibodies (Vaughan et al., "Human Antibodies with Sub-Nanomolar Affinities Isolated from a Large Non-immunized Phage Display Library," *Nature Biotechnology*, 14:309-314 (1996); Sheets et al., "Efficient Construction of a Large Nonimmune Phage Antibody Library: The Production of High-Affinity Human Single-Chain Antibodies to Protein Antigens," *Proc. Natl. Acad. Sci. U.S.A.* 95:6157-6162 (1998); Hoogenboom et al., "By-passing Immunisation. Human Antibodies From Synthetic Repertoires of Germline VH Gene Segments Rearranged In Vitro," *J Mol Biol* 227: 381-8 (1992); Marks et al., "By-passing Immunization. Human Antibodies from V-gene Libraries Displayed on Phage," *J Mol Biol* 222:581-97 (1991), which are hereby incorporated by reference in their entirety). Human antibodies can also be made in transgenic mice containing human immunoglobulin loci that are capable upon immunization of producing the full repertoire of human antibodies in the absence of endogenous immunoglobulin production. This approach is described in U.S. Pat. No. 5,545,807 to Surani et al.; U.S. Pat. No. 5,545,806 to Lonberg et al.; U.S. Pat. No. 5,569,825 to Lonberg et al.; U.S. Pat. No. 5,625,126 to Lonberg et al.; U.S. Pat. No. 5,633,425 to Lonberg et al.; and U.S. Pat. No. 5,661,016 to Lonberg et al., which are hereby incorporated by reference in their entirety Procedures for raising polyclonal antibodies are also well known. Typically, such antibodies can be raised by administering the peptide or polypeptide containing the epitope of interest (i.e. polymerized first or second peptides or fusion peptides) subcutaneously to rabbits (e.g., New Zealand white rabbits), goats, sheep, swine, or donkeys which have been bled to obtain pre-immune serum. The antigens can be injected in combination with an adjuvant. The rabbits are bled approximately every two weeks after the first injection and periodically boosted with the same antigen three times every six weeks. Polyclonal antibodies are recovered from the serum by affinity chromatography using the corresponding antigen to capture the antibody. This and other procedures for raising polyclonal antibodies are disclosed in Ed Harlow and David Lane, USING ANTIBODIES: A LABORATORY MANUAL (Cold Spring Harbor Laboratory Press, 1988), which is hereby incorporated by reference in its entirety.

In addition to whole antibodies, the present invention encompasses binding portions of such antibodies. Such binding portions include the monovalent Fab fragments, Fv fragments (e.g., single-chain antibody, scFv), and single variable $V_H$ and $V_L$ domains, and the bivalent $F(ab')_2$ fragments, BisscFv, diabodies, triabodies, minibodies, etc. These antibody fragments can be made by conventional procedures, such as proteolytic fragmentation procedures, as described in James Goding, MONOCLONAL ANTIBODIES: PRINCIPLES AND PRACTICE 98-118 (Academic Press, 1983) and Ed Harlow and David Lane, ANTIBODIES: A LABORATORY MANUAL (Cold Spring Harbor Laboratory, 1988), which are hereby incorporated by reference in their entirety, or other methods known in the art.

Also suitable for use in the present invention are antibody fragments engineered to bind to intracellular proteins, i.e. intrabodies. Although amyloid protein deposits are generally extracellular, intracellular accumulation of certain amyloid proteins (e.g., Aβ1-42) has been observed (D'Andrea et al., "Targeting Amyloid Beta: Targeting Intracellular Aβ42 for Alzheimer's Disease Drug Discover," *Drug Development Research* 56:194-200 (2002); Knobloch et al., "Intracellular Abeta and Cognitive Deficits Precede beta-Amyloid Deposition in arcAbeta Mice," *Neurobiol Aging* 28(9):1297-306 (2007), which are hereby incorporated by reference in their entirety). Accordingly, an intrabody can be used to bind selectively to an epitope of an amyloid protein within a cell. In a preferred embodiment, the intrabody recognizes an epitope of the Aβ1-42 oligomer accumulating within the perikaryon of affected neurons (e.g., pyramidal neurons) in AD.

Intrabodies are generally obtained by selecting a single variable domain from variable regions of an antibody having two variable domains (i.e., a heterodimer of a heavy chain variable domain and a light chain variable domain). Single chain Fv fragments, Fab fragments, ScFv-Ck fusion proteins, single chain diabodies, $V_H$-$C_H$1 fragments, and even whole IgG molecules are suitable formats for intrabody development (Kontermann R. E., "Intrabodies as Therapeutic Agents," *Methods* 34:163-70 (2004), which is here by incorporated by reference in its entirety).

Intrabodies having antigen specificity for a conformational epitope of an amyloidogenic protein can be obtained from phage display, yeast surface display, or ribosome surface display. Methods for producing libraries of intrabodies and isolating intrabodies of interest are further described in U.S. Published Patent Application No. 20030104402 to Zauderer and U.S. Published Patent Application No. 20050276800 to Rabbitts, which are hereby incorporated by reference in their entirety. Methods for improving the stability and affinity binding characteristics of intrabodies are described in WO2008070363 to Zhenping; Contreras-Martinez et al., "Intracellular Ribosome Display via SecM Translation Arrest as a Selection for Antibodies with Enhanced Cytosolic Stability," *J Mol Biol* 372(2):513-24 (2007), which are hereby incorporated by reference in their entirety.

It may further be desirable, especially in the case of antibody fragments, to modify the antibody in order to increase its serum half-life. This can be achieved, for example, by incorporation of a salvage receptor binding epitope into the antibody fragment by mutation of the appropriate region in the antibody fragment or by incorporating the epitope into a peptide tag that is then fused to the antibody fragment at either end or in the middle (e.g., by DNA or peptide synthesis).

Antibody mimics are also suitable for use in accordance with the present invention. A number of antibody mimics are known in the art including, without limitation, those known as monobodies, which are derived from the tenth human fibronectin type III domain ($^{10}$Fn3) (Koide et al., "The Fibronectin Type III Domain as a Scaffold for Novel Binding Proteins," *J Mol Biol* 284:1141-1151 (1998); Koide et al., "Probing Protein Conformational Changes in Living Cells by Using Designer Binding Proteins: Application to the Estrogen Receptor," *Proc Natl Acad Sci USA* 99:1253-1258 (2002), each of which is hereby incorporated by reference in its entirety); and those known as affibodies, which are derived from the stable alpha-helical bacterial receptor domain Z of staphylococcal protein A (Nord et al., "Binding Proteins Selected from Combinatorial Libraries of an alpha-helical Bacterial Receptor Domain," *Nature Biotechnol* 15(8):772-777 (1997), which is hereby incorporated by reference in its entirety).

The present invention is further directed to a pharmaceutical composition containing the isolated antibody of the present invention as described supra. In a preferred embodiment, the isolated antibody recognizes and binds to a shared conformational epitope common to one or more amyloid proteins. This pharmaceutical composition may contain an antibody mixture where all antibodies recognize the same conformational epitope. Alternatively, the pharmaceutical composition may contain an antibody mixture where one or more antibodies recognize one or more different conformational epitopes of amyloid proteins. The pharmaceutical composition of the present invention further contains a pharmaceutically acceptable carrier or other pharmaceutically acceptable components as described supra.

Another aspect of the present invention relates to a method of treating a condition mediated by an amyloidogenic protein in a subject. This method involves administering to the subject an antibody of the present invention, where the antibody has antigen specificity for a shared conformational epitope that is common to one or more amyloidogenic proteins. The antibody or a pharmaceutical composition containing the antibody is administered in an amount effective to treat the condition involving the amyloidogenic protein in the subject. In accordance with this aspect of the invention, the antibody or pharmaceutical composition containing the antibody is administered in an amount effective to generate passive immunity in the subject against one or more amyloidogenic proteins, thereby facilitating the clearance of amyloid deposits from the subject.

Conditions mediated by an amyloidogenic protein amenable to treatment in accordance with this aspect of the present invention are described supra.

In a preferred embodiment of this aspect of the present invention, a subject having a condition mediated by an amyloidogenic protein is selected prior to administration of the antibody of the present invention. Subjects amenable to treatment in accordance with the methods of the present invention include individuals at risk of developing an amyloid related disease but not showing symptoms, as well as subjects presently showing symptoms. Diseases subject to treatment include any disease associated with or caused by an amyloidogenic protein as described supra. The pharmaceutical compositions of the present invention contain polymers of peptides or fusion peptides that are not endogenous to the body, or antibodies specific for only pathological protein conformations. Therefore, the risk of inducing an autoimmune response is avoided and prophylactic treatment using these pharmaceutical compositions of the present invention is particularly suitable.

In the case of Alzheimer's disease, for example, virtually anyone is at risk of suffering from Alzheimer's disease if he or she lives long enough. Therefore, the compositions of the present invention can be administered prophylactically to the general population without the need for any assessment of the risk of the subject patient. The present methods and compositions are especially suitable for prophylactic treatment of individuals who have a known genetic risk of Alzheimer's disease or other condition related to an amyloidogenic protein. Genetic markers associated with a risk of Alzheimer's disease include mutations in the APP gene, particularly mutations at position 717 and positions 670 and 671 referred to as the Hardy and Swedish mutations respectively. Other markers of risk are mutations in the presenilin genes, PS1 and PS2, and ApoE4, family history of AD, hypercholesterolemia or atherosclerosis.

In asymptomatic patients, treatment can begin at any age (e.g., 10, 20, 30). Usually, however, it is not necessary to begin treatment until a patient reaches 40, 50, 60 or 70 years of age. Treatment typically entails multiple dosages over a period of time. Treatment can be monitored by assaying antibody, or activated T-cell or B-cell responses to the therapeutic agent (e.g., polymerized peptide) over time. If the response falls, a booster dosage is indicated. In the case of potential Down's syndrome patients, treatment can begin antenatally by administering the therapeutic agent to the mother or shortly after birth.

In prophylactic applications, the pharmaceutical compositions of the present invention are administered to a patient susceptible to, or otherwise at risk of, a particular disease in an amount sufficient to eliminate or reduce the risk or delay the onset of the disease. In therapeutic applications, pharmaceutical compositions are administered to a patient suspected of, or already suffering from an amyloidogenic disease in an amount sufficient to cure, or at least partially arrest, the symptoms of the disease and its complications. An amount adequate to accomplish this is defined as a therapeutically- or pharmaceutically-effective dose. In both prophylactic and therapeutic regimes, agents are usually administered in several dosages until a sufficient immune response has been achieved. Typically, the immune response is monitored and repeated dosages are given if the immune response starts to fade.

Effective doses of the compositions of the present invention, for the treatment of the above described conditions vary depending upon many different factors, including means of administration, target site, physiological state of the patient, whether the patient is human or an animal, other medications administered, and whether treatment is prophylactic or therapeutic. Usually, the subject is a human, but in some diseases, such prion protein related diseases, the subject can be a non-human mammal, such as a bovine. Other non-human mammals amenable to treatment in accordance with the methods of the present invention include primates, dogs, cats, rodents (e.g., mouse, rat, guinea pig), horses, deer, cervids, cattle and cows, sheep, and pigs. Treatment dosages need to be titrated to optimize safety and efficacy, and could involve oral treatment.

When treatment of a subject involves the administration of a pharmaceutical composition of the present invention containing the polymerized first or second peptide or fusion peptide immunogens, the appropriate dosage will depend on whether adjuvant is co-administered, with higher dosages being required in the absence of adjuvant. The amount of an immunogen for administration sometimes varies from 1 µg-500 µg per patient and more usually from 5-500 µg per injection for human administration. Occasionally, a higher dose of 1-2 mg per injection is used. Typically about 10, 20, 50 or 100 µg is used for each human injection. The timing of injections can vary significantly from once a day, to once a year, to once a decade. Generally an effective dosage can be monitored by obtaining a fluid sample from the patient, generally a blood serum sample, and determining the titer of antibody developed against the immunogen, using methods well known in the art and readily adaptable to the specific antigen to be measured. Ideally, a sample is taken prior to initial dosing and subsequent samples are taken and titered after each immunization. Generally, a dose or dosing schedule which provides a detectable titer at least four times greater than control or "background" levels at a serum dilution of 1:100 is desirable, where background is defined relative to a control serum or relative to a plate background in ELISA assays.

On any given day that a dosage of immunogen is given, the dosage is greater than 1 µg/patient and usually greater than 10 µg/patient if adjuvant is also administered, and greater than 10 µg/patient and usually greater than 100 µg/patient in the absence of adjuvant. A typical regimen consists of an immunization followed by booster injections at 6 weekly intervals. Another regimen consists of an immunization followed by booster injections 1, 2 and 12 months later. Another regimen entails an injection every two months for life. Alternatively, booster injections can be on an irregular basis as indicated by monitoring of immune response.

For passive immunization with a composition comprising an antibody of the present invention, the dosage ranges from about 0.0001 to 100 mg/kg, and more usually 0.01 to 5 mg/kg of the host body weight. An exemplary treatment regime entails administration once per every two weeks or once a month or once every 3 to 6 months. In some methods, two or more monoclonal antibodies with different binding specificities are administered simultaneously, in which case the dosage of each antibody administered falls within the ranges indicated. Antibody is usually administered on multiple occasions. Intervals between single dosages can be weekly, monthly or yearly. Intervals can also be irregular as indicated by measuring blood levels of antibody to polymerized first or second peptides or fusion peptides in the patient. Alternatively, antibody can be administered as a sustained release formulation, in which case less frequent administration is required. Dosage and frequency vary depending on the half-life of the antibody in the patient. In general, human antibodies show the longest half life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Agents for inducing an immune response can be administered by parenteral, topical, intravenous, oral, subcutaneous, intraperitoneal, intranasal or intramuscular means for prophylactic and/or therapeutic treatment. The most typical route of administration is subcutaneous although others can be equally effective. The next most common is intramuscular injection. This type of injection is most typically performed in the arm or leg muscles. Intravenous injections as well as intraperitoneal injections, intra-arterial, intracranial, or intradermal injections are also effective in generating an immune response. In some methods, agents are injected directly into a particular tissue where deposits have accumulated, for example intracranial injection. Intramuscular injection or intravenous infusion are preferred for administration of antibody. In some methods, particular therapeutic antibodies are injected directly into the cranium. In some methods, antibodies are administered as a sustained release composition or device, such as a Medipad™ device.

The pharmaceutical agents of the present invention may be formulated for parenteral administration. Solutions or suspensions of the agent can be prepared in water suitably mixed with a surfactant such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions. Under ordinary conditions of storage and use, these preparations contain a preservative to prevent the growth of microorganisms.

Pharmaceutical formulations suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

When it is desirable to deliver the pharmaceutical agents of the present invention systemically, they may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Intraperitoneal or intrathecal administration of the agents of the present invention can also be achieved using infusion pump devices such as those described by Medtronic, Northridge, Calif. Such devices allow continuous infusion of desired compounds avoiding multiple injections and multiple manipulations.

In addition to the formulations described previously, the agents may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

Another aspect of the present invention relates to a method of diagnosing an amyloid disease in a subject. This method involves detecting, in the subject, the presence of an amyloidogenic proteins or peptides using a diagnostic reagent, where the diagnostic reagent is an antibody, or active binding fragment thereof, of the present invention. As described supra, the antibody has antigenic specificity for a conformational epitope of a polymerized first or second peptide or fusion peptide that is shared with one or more other amyloidogenic protein or peptides. The diagnosis of the amyloid disease is based on the detection of an amyloidogenic protein or peptide in the subject.

Detecting the presence of amyloid deposits in a subject using the diagnostic reagent can be achieved by obtaining a biological sample from the subject (e.g., blood, urine, cerebral spinal fluid), contacting the biological sample with the diagnostic antibody reagent, and detecting binding of the diagnostic antibody reagent to an amyloid protein in the sample from the subject. Assays for carrying out the detection of an amyloid protein in a biological sample using a diagnostic antibody are well known in the art and include, without limitation, ELISA, immunohistochemistry, western blot.

Alternatively, detecting the presence of amyloid deposits in a subject using the diagnostic antibody reagent of the present invention can be achieved using in vivo imaging techniques. In vivo imaging involves administering to the subject the diagnostic antibody having antigenic specificity for a conformational epitope of a polymerized first or second peptide or fusion peptide, and detecting the binding of the diagnostic agent to the amyloidogenic protein in vivo. As described supra, preferred antibodies bind to a conformational epitope of an amyloid protein or peptide without binding to non-amyloid proteins and without binding to the non-pathological forms of the amyloid proteins.

Diagnostic antibodies or similar reagents can be administered by intravenous injection into the body of the patient, or directly into the brain by intracranial injection or by drilling a hole through the skull. The dosage of antibody should be within the same ranges as for treatment methods. Typically, the antibody is labeled, although in some methods, the primary antibody with affinity for the conformational epitope of an amyloid protein is unlabelled and a secondary labeling agent is used to bind to the primary antibody. The choice of label depends on the means of detection. For example, a fluorescent label is suitable for optical detection. Use of paramagnetic labels is suitable for tomographic detection without surgical intervention. Radioactive labels can also be detected using PET or SPECT.

Diagnosis is performed by comparing the number, size, and/or intensity of labeled amyloid protein deposits in a sample from the subject or in the subject, to corresponding baseline values. An appropriate baseline value can be the average level of amyloid protein deposition in a population of undiseased individuals. Alternatively, an appropriate baseline value may be the level of amyloid protein deposition in the same subject determined at an earlier time.

The diagnostic methods described above can also be used to monitor a subject's response to therapy. In this embodiment, detection of amyloid deposits in the subject is determined prior to the commencement of treatment. The level of amyloid deposition in the subject at this timepoint is used as a baseline value. At various times during the course of treatment the detection of amyloid deposits can be repeated, and the measured values thereafter compared with the baseline values. A decrease in values relative to baseline signals a positive response to treatment.

The present invention is further directed to a kit for performing the above described diagnostic and monitoring methods. Typically, such kits contain a diagnostic reagent, preferably the antibody of the present invention that has antigenic specificity for a polymerized first or second peptide or polymerized fusion peptide. The kit can also include a detectable label. The diagnostic antibody itself may contain the detectable label (e.g., fluorescent molecule, biotin, etc.) which is directly detectable or detectable via a secondary reaction (e.g., reaction with strepavidin). Alternatively, a second reagent containing the detectable label may be utilized, where the second reagent has binding specificity for the primary antibody. In a diagnostic kit suitable for measuring amyloid in a biological sample, the antibodies of the kit may be supplied prebound to a solid phase, such as to the wells of a microtiter dish.

Diagnostic kits of the present invention also include kits that are useful for detecting antibody production in a subject following administration of a polymerized first or second peptide or fusion peptide of the present invention. Typically, such kits include a reagent that contains the antigenic epitope of the antibodies generated by the subject. The kit also includes a detectable label. In a preferred embodiment, the label is typically in the form of labeled anti-idiotypic antibodies. The antigenic epitope reagents of the kit can be supplied prebound to a solid phase, such as to the wells of a microtiter dish.

Another aspect of the present invention relates to an isolated first peptide and the polynucleotide encoding the same. The isolated first peptide of the present invention has an amino acid sequence of $X_{1a}X_{2a}X_{3a}X_{4a}X_{5a}X_{6a}X_{7a}X_{8a}X_{9a}X_{10a}X_{11a}X_{12a}X_{13a}$ (SEQ ID NO: 19), wherein $X_{1a}$ is C, M, S, or G; $X_{2a}$ is T, S, or C; $X_{3a}$ is K, R, or H; $X_{4a}$ is S, T, or C; $X_{5a}$ is V, I, or L; $X_{6a}$ is R, K, or H; $X_{7a}$ is R, K, or H; $X_{8a}$ is Q or N; $X_{9a}$ is L, I, or V; $X_{10a}$ is L, I, or V; $X_{11a}$ is D or E; $X_{12a}$ is D or E; $X_{13a}$ is Q or N, with the proviso that the isolated first peptide does not have the amino acid sequence of SEQ ID NO:2. Particularly preferred isolated first peptides of the present invention include SEQ ID NO: 3 or SEQ ID NO:5. These isolated peptides are encoded by nucleic acid molecules having the nucleotide sequence of SEQ ID NO:4 (tgt tct aga tca gtc aag aaa caa att att gag gaa aat) and SEQ ID NO:6 (tgt act aaa aca ctc agg aga caa ctt ctt gat gac caa), respectively.

Another aspect of the present invention relates to an isolated second peptide and the polynucleotide encoding the same. The isolated second peptide of the present invention has an amino acid sequence of $X_{1b}X_{2b}X_{3b}X_{4b}X_{5b}X_{6b}X_{7b}X_{8b}X_{9b}X_{10b}X_{11b}X_{12b}X_{13b}$ (SEQ ID NO: 20), wherein $X_{1b}$ is C, M, S, or G; $X_{2b}$ is F, Y, or W; $X_{3b}$ is Q or N; $X_{4b}$ is I, L, or V; $X_{5b}$ is F, Y, or W; $X_{6b}$ is I, L, or V; $X_{7b}$ is Q or N; $X_{8b}$ is T, S, or C; $X_{9b}$ is N or Q; $X_{10b}$ is D or E; $X_{11b}$ is R, K, or H; $X_{12b}$ is H, R, or K; $X_{13b}$ is Y, W, or F, with the proviso that the isolated second peptide does not have the amino acid sequence of SEQ ID NO:8. Particularly preferred isolated second peptides of the present invention include SEQ ID NO: 9 or SEQ ID NO:11. These isolated peptides are encoded by nucleic acid molecules having the nucleotide sequence of SEQ ID NO:10 (tgt ttt caa ttg ttc ttg aac act caa gaa aaa cat tat) and SEQ ID NO:12 (tgt tgg caa ttg tgg att cag agt aac gat cat aaa ttt), respectively.

Another aspect of the present invention is directed to an isolated fusion peptide. This fusion peptide of the present invention contains a first peptide of the invention (SEQ ID NO:19) coupled to itself, any other first peptide or reverse first peptide of the invention, or any second peptide (SEQ ID NO:20) or reverse second peptide of the invention. Alternatively, the fusion peptide contains any second peptide of the invention (SEQ ID NO:20) coupled to itself, any other second peptide or reverse second peptide of the invention, or a first (SEQ ID NO:19) or reverse first peptide of the invention.

The portions of the fusion peptide are preferably linked by a glycine or serine-rich linker described supra. Exemplary fusion peptides of the present invention have an amino acid sequence of SEQ ID NO:13, SEQ ID NO:15, or SEQ ID NO:17. These isolated peptides are encoded by nucleic acid molecules having the nucleotide sequence of SEQ ID NO:14 (tgt tct aga aca gtc aag aaa aac att att gag gaa aat ggg tct ggg tct ggg tgt ttt aat ttg ttc ttg aac agt caa gaa aaa cat tat), SEQ ID NO:16 (tgt tct aga tca gtc aag aaa caa att att gag gaa aat ggg tct ggg tct ggg tgt ttt caa ttg ttc ttg aac act caa gaa aaa cat tat), and SEQ ID NO:18 (tgt act aaa aca ctc agg aga caa ctt ctt gat gac caa ggg tct ggg tct ggg tgt tgg caa ttg tgg att cag agt aac gat cat aaa ttt), respectively.

The isolated peptides of the present invention may be prepared for use in the above described methods of the present invention using standard methods of synthesis known in the art, including solid phase peptide synthesis (Fmoc or Boc strategies) or solution phase peptide synthesis. Alternatively, peptides of the present invention may be prepared using recombinant expression systems.

Generally, the use of recombinant expression systems involves inserting the nucleic acid molecule encoding the amino acid sequence of the desired peptide into an expression system to which the molecule is heterologous (i.e., not normally present). One or more desired nucleic acid molecules encoding a peptide of the invention may be inserted into the vector. When multiple nucleic acid molecules are inserted, the multiple nucleic acid molecules may encode the same or different peptides. The heterologous nucleic acid molecule is inserted into the expression system or vector in proper sense (5'→3') orientation relative to the promoter and any other 5' regulatory molecules, and correct reading frame.

The preparation of the nucleic acid constructs can be carried out using standard cloning procedures well known in the art as described by Joseph Sambrook et al., MOLECULAR CLONING: A LABORATORY MANUAL (Cold Springs Harbor 1989). U.S. Pat. No. 4,237,224 to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and replicated in a suitable host cell.

A variety of genetic signals and processing events that control many levels of gene expression (e.g., DNA transcription and messenger RNA ("mRNA") translation) can be incorporated into the nucleic acid construct to maximize peptide production. For the purposes of expressing a cloned nucleic acid sequence encoding a desired peptide, it is advantageous to use strong promoters to obtain a high level of transcription. Depending upon the host system utilized, any one of a number of suitable promoters may be used. For instance, when cloning in *E. coli*, its bacteriophages, or plasmids, promoters such as the T7 phage promoter, lac promoter, trp promoter, recA promoter, ribosomal RNA promoter, the $P_R$ and $P_L$ promoters of coliphage lambda and others, including but not limited, to lacUV5, ompF, bla, lpp, and the like, may be used to direct high levels of transcription of adjacent DNA segments. Additionally, a hybrid trp-lacUV5 (tac) promoter or other *E. coli* promoters produced by recombinant DNA or other synthetic DNA techniques may be used to provide for transcription of the inserted gene. Common promoters suitable for directing expression in mammalian cells include, without limitation, SV40, MMTV, metallothionein-1, adenovirus Ela, CMV, immediate early, immunoglobulin heavy chain promoter and enhancer, and RSV-LTR.

There are other specific initiation signals required for efficient gene transcription and translation in prokaryotic cells that can be included in the nucleic acid construct to maximize peptide production. Depending on the vector system and host utilized, any number of suitable transcription and/or translation elements, including constitutive, inducible, and repressible promoters, as well as minimal 5' promoter elements, enhancers or leader sequences may be used. For a review on maximizing gene expression see Roberts and Lauer, "Maximizing Gene Expression On a Plasmid Using Recombination In Vitro," *Methods in Enzymology* 68:473-82 (1979), which is hereby incorporated by reference in its entirety.

A nucleic acid molecule encoding an isolated peptide of the present invention, a promoter molecule of choice, including, without limitation, enhancers, and leader sequences; a suitable 3' regulatory region to allow transcription in the host, and any additional desired components, such as reporter or marker genes, are cloned into the vector of choice using standard cloning procedures in the art, such as described in Joseph Sambrook et al., MOLECULAR CLONING: A LABORATORY MANUAL (Cold Springs Harbor 1989); Frederick M. Ausubel, SHORT PROTOCOLS IN MOLECULAR BIOLOGY (Wiley 1999), and U.S. Pat. No. 4,237,224 to Cohen and Boyer, which are hereby incorporated by reference in their entirety.

Once the nucleic acid molecule encoding the peptide has been cloned into an expression vector, it is ready to be incorporated into a host. Recombinant molecules can be introduced into cells, without limitation, via transfection (if the host is a eukaryote), transduction, conjugation, mobilization, or electroporation, lipofection, protoplast fusion, mobilization, or particle bombardment, using standard cloning procedures known in the art, as described by JOSEPH SAMBROOK et al., MOLECULAR CLONING: A LABORATORY MANUAL (Cold Springs Harbor 1989), which is hereby incorporated by reference in its entirety.

A variety of suitable host-vector systems may be utilized to express the recombinant protein or polypeptide. Primarily, the vector system must be compatible with the host used. Host-vector systems include, without limitation, the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus); and plant cells infected by bacteria.

Purified peptides may be obtained by several methods readily known in the art, including ion exchange chromatography, hydrophobic interaction chromatography, affinity chromatography, gel filtration, and reverse phase chromatography. The peptide is preferably produced in purified form (preferably at least about 80% or 85% pure, more preferably at least about 90% or 95% pure) by conventional techniques. Depending on whether the recombinant host cell is made to secrete the peptide into growth medium (see U.S. Pat. No. 6,596,509 to Bauer et al., which is hereby incorporated by reference in its entirety), the peptide can be isolated and purified by centrifugation (to separate cellular components from supernatant containing the secreted peptide) followed by sequential ammonium sulfate precipitation of the supernatant. The fraction containing the peptide is subjected to gel filtration in an appropriately sized dextran or polyacrylamide column to separate the peptides from other proteins. If necessary, the peptide fraction may be further purified by HPLC.

EXAMPLES

The following examples are provided to illustrate embodiments of the present invention but they are by no means intended to limit its scope.

Example 1

Synthesis of Peptide

The 13 amino acid residue peptide corresponding to the carboxyl terminus of ABri (Cys-Ser-Arg-Thr-Val-Lys-Lys-Asn-Ile-Ile-Glu-Glu-Asn) (SEQ ID NO:2) was synthesized on an ABI 430A peptide synthesizer (AME Bioscience, Chicago, Ill.) at the Keck peptide synthesis facility at Yale University, CT, using a Vydac C18 preparative column, 2.5×30 cm (Vydac Separations, Hesperia, Calif.). Standard protocols for tBOC (tert-butyloxycarbonyl) chemistry were used. The peptide was subsequently cleaved from the resins using hydrofluoric acid and purified by high-pressure liquid chromatography (HPLC) on a Vydac C18 preparative column using linear gradients from 0-70% of acetonitrile in 0.1% trifluoroacetic acid. Mass spectroscopy of the lyophilized end-product was used to verify the expected molecular weight.

Example 2

Polymerization of the ABri Peptide and Assessment of Conformation

In order to make the 13 amino acid residue ABri peptide immunogenic and to potentially ensure a conformation specific immune response, the peptide was first subjected to controlled polymerization using the following protocol. The peptide was dissolved at 3 mg/ml, in 100 mM borate buffer saline (BBS), pH 7.4. Fresh 1% glutaraldehyde in BBS was prepared and added to the peptide to a final 5 mM glutaraldehyde concentration and incubated in an Eppendorf block at 800 rpm at 56° C. for 16 hrs. The solution was then quenched with 0.5 M glycine to make the solution 100 mM in glycine. After five minutes the solution was diluted 1:3 with BBS, dialyzed against 2 mM BBS overnight at 4° C., aliquoted, and lyophilized. To determine the degree of aggregation, the original monomeric ABri peptide and polymerized ABri peptide (pABri) were electrophoresed on 12.5% SDS-polyacrylamide Tris-tricine gels under reducing conditions. Western blots were performed with a mouse anti-ABri polyclonal Ab (Vidal et al., "Cerebral Amyloid Angiopathy and Parenchymal Amyloid Deposition in Transgenic Mice Expressing the Danish Mutant Form of Human BRI(2)," *Brain Pathol.* 19:58-68 (2009), which is hereby incorporated by reference in its entirety) (1:1,000 dilution). The secondary antibody (1:2,000 dilution) was peroxidase-linked anti-rabbit IgG (Amersham Biosciences, Piscataway, N.J.), and the immunoreactive material was visualized as chemoluminescence on X-ray film with an ECL detection kit (Pierce). For electron microscopic studies, the original and polymerized ABri peptides were incubated at 1 mg/ml in phosphate buffered saline, pH 7.4. The sample (3 µl) was put onto a carbon coated 400 mesh Cu/Rh grid (Ted Pella Inc., Redding, Calif.) and stained with 1% uranyl acetate in distilled water (Polysciences, Inc, Warrington, Pa.). Stained grids were examined under a Philips CM-12 electron microscope (FEI; Eindhoven, The Netherlands) and photographed with a (1 k×1 k) digital camera (Gatan, Inc., Pleasanton, Calif.). For secondary structure analysis, aliquots of the original ABri peptide and pABri were reconstituted in 5 mM Tris buffer (pH 7.0) to obtain a peptide concentration of 100 µM. Circular dichroism (CD) was measured on a Jasco J-720 spectropolarimeter (Easton, Md.) equipped with a model CTC-344 circular temperature control system (Neslab Inc., Newington, N.H.) according to a previously described protocol (Sadowski et al., "Blocking the Apolipoprotein E/β-Amyloid Interaction Reduces β-Amyloid Toxicity and Decreases β-Amyloid Load in Transgenic Mice," *Am. J. Pathol.* 165:937-948 (2004), which is hereby incorporated by reference in its entirety). The neural network algorithm (Softsec software; Softwood Inc., PA) was used to obtain percentages of different types of secondary structures of the analyzed peptides (Toumadje et al., "Extending CD Spectra of Proteins to 168 nm Improves the Analysis for Secondary Structures," *Anal. Biochem.* 200:321-331 (1992); Sreerma et al., "A Self-Consistent Method for the Analysis of Protein Secondary Structure From Circular Dichroism," *Anal. Biochem.* 209:32-44 (1993), which are hereby incorporated by reference in their entirety).

Example 3

Purification of Paired Helical Filaments (PHF)

PHFs were purified from the brain of a subject from the New York University Alzheimer's Disease Center brain bank, who fulfilled the National Institute on Aging-Reagan criteria for AD at autopsy (Kascsak et al., "The Role of Antibodies To PrP in the Diagnosis of Transmissible Spongiform Encephalopathies," *Dev. Biol. Stand.* 80:141-151 (1993), which is hereby incorporated by reference in its entirety). Briefly, 30 gm of frontal cortex was homogenized in 75 ml of 50 mM Tris-buffered saline (TBS), pH 7.4, using an Ultra Turrox T25 tissue homogenize (IKA Works, Inc; Staufen, Germany). To the homogenized tissue sample, 75 ml of 20% sarcosyl in water was added and it was homogenized again. The homogenized material was centrifuged at 3,500 rpm in a Beckman GPR centrifuge, and 6 ml aliquots of the supernatant were each layered over 1 ml TBS/0.1% SB3-14 and centrifuged in an Optima Max ultracentrifuge at 75,000 rpm for 2 hours at 20° C. Each pellet was resuspended by sonication in 1 ml of 10% NaCl in TBS/0.1% SB3-14, followed by the addition of 6 ml of 10% NaCl in TBS/0.1% SB3-14 and centrifuged at 75,000 rpm for 1.5 hours at 20° C. The pellets were sonicated in 1 ml of 10% NaCl in TBS/0.1% SB3-14 followed by the addition of 6 ml of 10% NaCl in TBS/0.1% SB3-14, layered over 1 ml of 20% sucrose in 10% NaCl TBS/0.1% SB3-14 and centrifuged at 75,000 rpm for 1.5 hours at 20° C. The final pellets were resuspended in TBS/0.1% SB3-14 by sonication prior to use.

Example 4

Immunization of Mice

Animal studies were approved by the NYU School of Medicine Institutional Animal Care and Use Committee and were consistent with the recommendations of the American Veterinary Association. The pABri peptide was dissolved in sterile saline at 1 mg/ml and mixed 1:1 with Aluminum Hydroxide (Alum) adjuvant (Brenntag Biosector, Denmark). Each mouse received a weekly subcutaneous injection of 100 µl of the preparation for 4 weeks followed by an inoculation one month later and two subsequent bimonthly injections. The last three inoculations used 25 µg of pABri per animal and the ratio of saline to alum ratio was changed to 9:1. Two groups of APP K670N/M671L/PS1 M146L (APP/PS1) Tg mice (Holcomb et al., "Accelerated Alzheimer-Type Phenotype in Transgenic Mice Carrying Both Mutant Amyloid Precursor Protein and Presenilin 1 Transgenes," *Nature Med.* 4:97-100 (1998), which is hereby incorporated by reference in its entirety) were immunized with either pABri in saline with alum or saline with alum alone starting at the age of 2 months, with the mouse breeding and genotyping as previously described (Sadowski et al., "Blocking the Apolipoprotein/Amyloid β Interaction Reduces the Parenchymal and Vascular Amyloid-β Deposition and Prevents Memory Deficit in AD Transgenic Mice," *Proc. Natl. Acad. Sci.* (USA) 103:18787-18792 (2006), which is hereby incorporated by reference in its entirety). Animals were bled from the caudal vein one week after the 4th and 6th inoculations (T4 and T6, respectively) and at the time of sacrifice (TF). The blood was collected in heparinized tubes and plasma separated and stored at −80° C. Amyloid deposition in this mouse AD Tg model starts at about the age of 3 months (McGowan et al., "Amyloid Phenotype Characterization of Transgenic Mice Overexpressing Both Mutant Amyloid Precursor Protein and Mutant Presenilin 1 Transgenes," *Neurobiol. Dis.* 6:231-244 (1999), which is hereby incorporated by reference in its entirety). At the age of 14 months the two groups of Tg mice were subject to behavioral testing using the radial arm maze with comparison to a third group of 15 mice which were age and sex matched, non-Tg littermate controls which had been given subcutaneous injections of saline/alum alone.

Example 5

Sensorimotor and Cognitive Testing

Sensorimotor and cognitive testing were done as previously described (Scholtzova et al., "A NMDA Receptor Antagonist Leads to Behavioral Improvement and Amyloid Reduction in Alzheimer's Disease Model Transgenic Mice Shown by Micro-Magnetic Resonance Imaging," *J. Neurosci. Res.* 86:2784-2791 (2008); Asuni et al., "Aβ Derivative Vaccination in Alum Adjuvant Prevents Amyloid Deposition and Does Not Cause Brain Microhemorrhages in Alzheimer's Model Mice," *Eur. J. Neurosci.* 24:2530-2542 (2006); Sadowski et al., "Blocking the Apolipoproteine/Amyloid β Interaction Reduces the Parenchymal and Vascular Amyloid-β Deposition and Prevents Memory Deficit in AD Transgenic Mice," *Proc. Natl. Acad. Sci.* (USA) 103:18787-18792 (2006), which are hereby incorporated by reference in their entirety). Prior to testing, the mice were adapted to the room with lights on for 15 minutes. The main objective of performing these sensorimotor tasks was to verify that any treatment related effects observed in the cognitive tasks could not be explained by differences in sensorimotor abilities.

Locomotor Activity:

A Hamilton-Kinder Smart-frame Photobeam System was used to make a computerized recording of animal activity over a designated period of time. Exploratory locomotor activity is recorded in a circular open field activity chamber measuring (70×70 cm). A video camera mounted above the chamber automatically recorded horizontal movements in the open field in each dimension (i.e., x, y, and two z planes). Total distance was measured in centimeters (cm) traveled and is defined as sequential movement interruptions of the animal measured relative to the background. The duration of the behavior was timed for 15 min. Results were reported based on distance traveled (cm), mean resting time, and maximum velocity of the animal.

Traverse Beam:

This task tests balance and general motor coordination and function integration. Mice were assessed by measuring their ability to traverse a graded narrow wooden beam to reach a goal box specifically examining hind limb function. The mice were placed on a beam, 1 cm wide and 50.8 cm long, suspended 30 cm above a padded surface by two identical columns. Attached at each end of the beam was a shaded goal box. Mice were placed on the beam in a perpendicular orientation to habituate, and were then monitored for a maximum of 60 seconds. The number of foot slips each mouse has before falling or reaching the goal box was recorded for each of three successive trials. The average foot slips for all four trials was calculated and recorded. Errors are defined as foot slips and recorded both numerically and using Feeney scores. To prevent injury from falling, a soft foam cushion was always kept underneath the beam. Animals that fell off were placed back in their position prior to the fall.

Rotarod:

The animal was placed onto the rod (diameter 3.6 cm) apparatus to assess differences in motor coordination and balance by measuring fore- and hind limb motor coordination and balance (Rotarod 7650 accelerating model; Ugo Basile, Biological Research Apparatus, Varese, Italy). This procedure was designed to assess motor behavior without a practice confound. The animals were habituated to the apparatus by receiving training sessions of two trials, sufficient to reach a baseline level of performance. Then the mice were tested a further 3 times, with increasing speed. During habituation, the rotor rod was set at 1.0 rpm, which was gradually raised every 30 seconds, and was also wiped clean with 30% ethanol solution after each session. A soft foam cushion was placed beneath the apparatus to prevent potential injury from falling. Each animal was tested for three sessions, with each session separated by 15 minutes, and measures were taken for latency to fall or invert (by clinging) from the top of the rotating barrel.

Radial Arm Maze:

Prior to testing, the mice were adapted to the room with lights on for 15 min Spatial learning was evaluated using an eight-arm radial maze with a water well at the end of each arm. Clear Plexiglas guillotine doors, operated by a remote pulley system, controlled access to the arms from a central area from which the animals entered and exited the apparatus. After 3-4 days of adaptation, water-restricted mice (2 hours daily access to water) were given one training session per day for ten consecutive days. For each session, all arms were baited with saccharine flavored water, and animals were permitted to enter all arms until the eight rewards had been consumed. The number of errors (entries to previously visited arms) and time to complete each session were recorded.

Example 6

Antibody Levels

Antibody levels were determined in duplicate on 1:100 dilutions of plasma using ELISA as described previously (Goni et al., "Mucosal Vaccination Delays or Prevents Prion Infection Via an Oral Route," Neurosci. 133:413-421 (2005); Asuni et al., "Aβ Derivative Vaccination in Alum Adjuvant Prevents Amyloid Deposition and Does Not Cause Brain Microhemorrhages in Alzheimer's Model Mice," Eur. J. Neurosci. 24:2530-2542 (2006), which are hereby incorporated by reference in their entirety), in which 5 µg/plate Aβ1-42, pABri or purified PHF was coated onto Immulon 2HB 96 well microtiter wells (Thermo, Waltham, Mass.). The bound antibodies were detected by a horseradish peroxidase labeled goat anti-mouse IgG (Amersham Biosciences, Piscataway, N.J.) or a peroxidase conjugated goat anti-mouse IgM (Sigma; A8786). Tetramethyl benzidine (TMB; Pierce, Rockford, Ill.) was the color developing substrate and the readings were done at 450 nm.

Blood samples from immunized mice were also tested by ELISA and western blot for reactivity against aggregated Aβ42, aggregated Aβ40, and PRP$^{sc}$.

Example 7

Histology

Mice were anesthetized with sodium pentobarbital (150 mg/kg, i.p.), perfused transaortically with phosphate buffer, and the brains processed as described previously (Asuni et al., "Aβ Derivative Vaccination in Alum Adjuvant Prevents Amyloid Deposition and Does Not Cause Brain Microhemorrhages in Alzheimer's Model Mice," Eur. J. Neurosci. 24:2530-2542 (2006); Sigurdsson et al., "An Attenuated Immune Response is Sufficient to Enhance Cognition in an Alzheimer's Disease Mouse Model Immunized With Amyloid-β Derivatives," J. Neurosci. 24:6277-6282 (2004), which are hereby incorporated by reference in their entirety). The right hemisphere was immersion-fixed in periodate-lysine-paraformaldehyde, whereas the left hemisphere was snap-frozen for measurements of Aβ levels. Serial coronal sections (40 µm) were cut, and every fifth section (30-40 sections in total) was stained with a mixture of 4G8/6E10, monoclonal antibodies that recognizes Aβ and stains both pre-amyloid and Aβ plaques (Sadowski et al., "Blocking the Apolipoproteine/Amyloid β Interaction Reduces the Parenchymal and Vascular Amyloid-β Deposition and Prevents Memory Deficit in AD Transgenic Mice," Proc. Natl. Acad. Sci. (USA) 103:18787-18792 (2006); Scholtzova et al., "Induction of Toll-Like Receptor 9 Signaling as a Method for Ameliorating Alzheimer's Disease Related Pathology," J. Neurosci. 29:1846-1854 (2009), which are hereby incorporated by reference in their entirety). Immunostaining was performed as described previously (Sadowski et al., "Blocking the Apolipoproteine/Amyloid β Interaction Reduces the Parenchymal and Vascular Amyloid-β Deposition and Prevents Memory Deficit in AD Transgenic Mice," Proc. Natl. Acad. Sci. (USA) 103:18787-18792 (2006); Scholtzova et al., "Induction of Toll-Like Receptor 9 Signaling as a Method for Ameliorating Alzheimer's Disease Related Pathology," J. Neurosci. 29:1846-1854 (2009), which are hereby incorporated by reference in their entirety). Briefly, sections were incubated in 6E10/4G8 each at a 1:1000 dilution in PBS-T for 3 hours. A mouse-on-mouse immunodetection kit (Vector Laboratories, Burlingame, Calif.) was used. The sections were incubated first with biotinylated anti-mouse IgG secondary antibody for 1 hour at a 1:2000 dilution and later with the avidin-peroxidase complex for 30 min at the same dilution. The sections were then reacted in 3,3-diaminobenzidine tetrahydrochloride with nickel ammonium sulfate (Ni; Mallinckrodt, Paris, Ky.) color intensification solution. Immunohistochemistry of tissue sections was quantified with a Bioquant image analysis system (BIOQUANT Image Analysis Corporation, Nashville, Tenn.), and unbiased sampling was used (Scholtzova et al., "Induction of Toll-Like Receptor 9 Signaling as a Method for Ameliorating Alzheimer's Disease Related Pathology," J. Neurosci. 29:1846-1854 (2009), which is hereby incorporated by reference in its entirety). All procedures were performed by an individual blinded to the experimental conditions of the study. The cortical area analyzed was dorsomedial from the cingulate cortex and extended ventrolaterally to the rhinal fissure within the right hemisphere. The area of the grid was 800 µm$^2$×800 µm$^2$, and deposit load was measured in 20 cortical frames per mouse (640×480 µm$^2$ each) chosen randomly. The Aβ burden is defined as the percentage of area in the measurement field occupied by reaction product.

Mouse plasma was used for immunostaining of human tissue. Staining was performed on 8 µm deparaffinized sections of temporal cortex. Tissue samples were obtained from New York University Alzheimer's Disease Center Brain Bank. The tissue was from a subject that had fulfilled the National Institute on Aging-Reagan criteria for AD or an age matched control with no AD related pathology at autopsy. Selected series were double immunostained with pooled plasma from pABri immunized Tg mice and PHF-1 mAb (to abnormally phosphorylated tau protein (Otvos et al., "Monoclonal Antibody PHF-1 Recognizes Tau Protein Phosphorylated At Serine Residues 396 and 404," J. Neurosci. Res. 39:669-673 (1994), which is hereby incorporated by reference in its entirety). Briefly, sections were incubated overnight at 4° C. with pooled plasma from the T6 bleedings of pABri immunized Tg diluted 1:100 in PBS, 0.1% Triton X-100, 0.01% sodium azide, and 1% BSA. Bound antibody staining was performed with a secondary biotinylated goat anti-mouse IgM (mu chain specific, Vector Laboratories) incubated for 1 h at a 1:500 dilution. First, primary antibody staining was revealed with 3,3'-diamonobenzidine (DAB Sigma-Aldrich) and nickel ammonium sulfate intensification. After several washes, the tissue was blocked again in PBS, 10% FBS, 0.2% Triton X-100 and the second primary antibody PHF-1 (monoclonal, 1:200; 1 h) was added, followed by incubation with alkaline phosphatase labeled horse anti-mouse IgG (1:500, 1 hour; Vector Laboratories). Next an alkaline phosphatase substrate kit (Vector) was applied to produce a red reaction product.

Example 8

Tissue Homogenization and Sandwich ELISA Assay for Soluble Levels

Extraction of Aβ from brain tissue was performed as previously described (Scholtzova et al., "Induction of Toll-Like Receptor 9 Signaling as a Method for Ameliorating Alzheimer's Disease Related Pathology," J. Neurosci. 29:1846-1854 (2009), which is hereby incorporated by reference in its entirety). Brains were weighed and homogenized (10% w/v) in homogenization buffer, 20 mM Tris, 250 mM sucrose, 1 mM EDTA, 1 mM EGTA with freshly prepared 100 mM phenylmethylsulfonyl fluoride, 5 µg/ml pepstatin A and a protease inhibitor cocktail (Complete, Roche Diagnostics, Indianapolis, Ind.). For extraction of soluble A13, brain homogenates were thoroughly mixed with an equal volume of 0.4% diethylamine (DEA)/100 mM NaCl, then spun at 135,000×g for 1 hour at 4° C., and subsequently neutralized with $\frac{1}{10}$ volume of 0.5 M Tris, pH 6.8. The samples were then aliquoted, flash-frozen on dry ice, and stored at −80° C. until loaded onto ELISA plates. Similarly for extraction of the total Aβ, 200 µl of each homogenate was added to 440 µl of cold formic acid (FA) and sonicated for one minute over ice. Subsequently, 400 µl of the solutions were spun at 100,000 g for 1 hour at 4° C. The resulting supernatants (210 µl) were diluted with 4 ml of FA neutralization solution (1 M Tris, 0.5 M Na2HPO4, 0.05% NaN3), aliquoted, flash-frozen on dry ice and stored at −80° C. until used for Aβ measurements.

The total and soluble Aβ levels were measured using a combination of mouse monoclonal antibody 6E10 (specific to an epitope present on amino acid residues 1 to 16 of Aβ) and two different rabbit polyclonal antibodies specific for Aβ40 (R162) and Aβ42 (R165), in a double-antibody sandwich ELISA as described previously (Sadowski et al., "Blocking the Apolipoproteine/Amyloid β Interaction Reduces the Parenchymal and Vascular Amyloid-β Deposition and Prevents Memory Deficit in AD Transgenic Mice," *Proc. Natl. Acad. Sci.* (USA) 103:18787-18792 (2006); Scholtzova et al., "Induction of Toll-Like Receptor 9 Signaling as a Method for Ameliorating Alzheimer's Disease Related Pathology," *J. Neurosci.* 29:1846-1854 (2009), which are hereby incorporated by reference in their entirety). The optical density (OD) was measured at 450 nm. The relationship between OD and Aβ peptide concentration was determined by a four-parameter logistic log function. Non-linear curve fitting was performed with the KinetiCalc program (Biotek Instruments, Inc., Winooski, Vt.) to convert OD of plasma to estimated concentrations. The assay was performed by an investigator blinded to group assignment. The levels of Aβ species are presented as µg of Aβ per gram of wet brain, taking into account dilution factors introduced by multiple steps throughout the assay (brain homogenization and extraction procedures).

Example 9

Western Blot Analysis of Aβ Oligomers

For western immunoblot analysis, 10% w/v brain homogenates were centrifuged at 25,000 g for 10 min at 4° C., and the supernatants were transferred to clean tubes and stored as previously described (Sadowski et al., "Blocking the Apolipoproteine/Amyloid β Interaction Reduces the Parenchymal and Vascular Amyloid-β Deposition and Prevents Memory Deficit in AD Transgenic Mice," *Proc. Natl. Acad. Sci.* (USA) 103:18787-18792 (2006); Scholtzova et al., "Induction of Toll-Like Receptor 9 Signaling as a Method for Ameliorating Alzheimer's Disease Related Pathology," *J. Neurosci.* 29:1846-1854 (2009), which are hereby incorporated by reference in their entirety). The total protein concentration in the supernatant was determined using the Bicinchoninic acid assay (BCA; Pierce, Rockford, Ill.). Samples (40 µg of total protein), were mixed with an equal volume of Tricine sample buffer (BioRad, Hercules, Calif.), electrophoresed on 12.5% Tris-tricine polyacrylamide gels under nonreducing conditions, and transferred to nitrocellulose membranes. The blots were blocked with 5% nonfat dry milk in TBS-T, pH 8.3, for 2 hours at room temperature, then incubated with oligomer-specific rabbit A11 polyclonal antiserum (Biosource, Camarillo, Calif.), diluted 1:1000 in TBS-T, 0.1% BSA for 2 hrs at room temperature. Bound antibody was detected after 1 hour incubation with horseradish peroxidase-conjugated goat anti-rabbit IgG 1:8000 (Pierce, Rockford, Ill.) and the ECL detection system (Pierce, Rockford, Ill.). The specificity of A11 staining was confirmed by probing the membrane with anti-Aβ monoclonal antibodies 6E10 or 4G8 (Sadowski et al., "Blocking the Apolipoproteine/Amyloid β Interaction Reduces the Parenchymal and Vascular Amyloid-β Deposition and Prevents Memory Deficit in AD Transgenic Mice," *Proc. Natl. Acad. Sci.* (USA) 103:18787-18792 (2006), which is hereby incorporated by reference in its entirety). Densitometric analysis of A11 immunoreactive oligomer specific bands was performed with NIH Image J version 1.34 software.

Example 10

Statistical Analysis

Data from the radial arm maze were analyzed by two-way repeated measures ANOVA followed by a Neuman-Keuls posthoc test. Differences between groups in the amyloid burden, Aβ levels within the brain, and levels of oligomers, were analyzed using a Student's unpaired two-tailed t-test. Statistical analysis was done using GraphPad Prism version 5.0 (GraphPad Software Inc., La Jolla, Calif.).

Example 11

Characterization of the Aggregation State of pABri and its Conformation

Figure 10B:
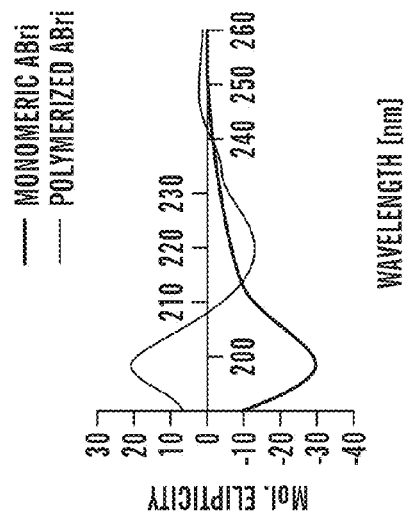
FIGS. 10A-10C show the aggregation state of the pABri and its conformation.
Figure 10C:
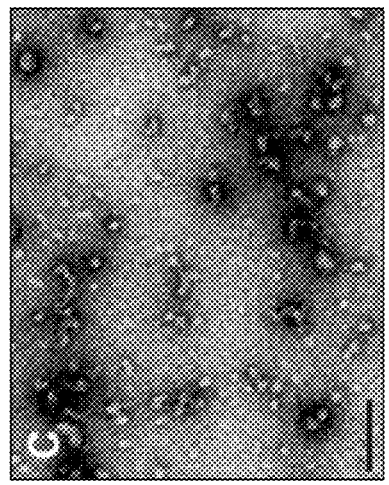
Figure 10A:
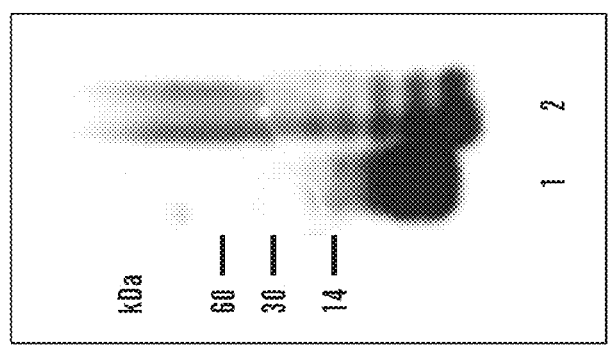

As determined by SDS-PAGE and western blotting the freshly dissolved ABri peptide is mainly monomeric with some lower order aggregates of dimers and tetramers (FIG. 10A, lane 1). The pABri had a lower percentage of monomeric form, an increase of multimers and a predominance of higher order aggregates in a range of 30 to 100 kDa (FIG. 10A, lane 2). Circular dichroism of these peptides indicated that the freshly dissolved ABri peptide has a predominant random coil structure with a minimum at 195 nm, in contrast to the pABri that had a predominantly β-sheet structure with a minimum at 220 nm and a maximum at 195 nm (FIG. 10B). The electron microscopic appearance of the pABri is predominately spherical particles of ~10 nm, similar to what has been reported for other amyloid oligomers (FIG. 10C) (Kayed et al., "Common Structure of Soluble Amyloid Oligomers Implies Common Mechanism of Pathogenesis," *Science* 300:486-489 (2003), and Glabe et al., "Structural Classification of Toxic Amyloid Oligomers," *J. Biol. Chem.* 283:29639-29643 (2008), which are hereby incorporated by reference in their entirety). In contrast the mainly monomeric, freshly dissolved ABri peptide did not form any structures such as spherical particles or fibrils by electron microscopy.

Example 12

Antibody Titers

Figure 11A:
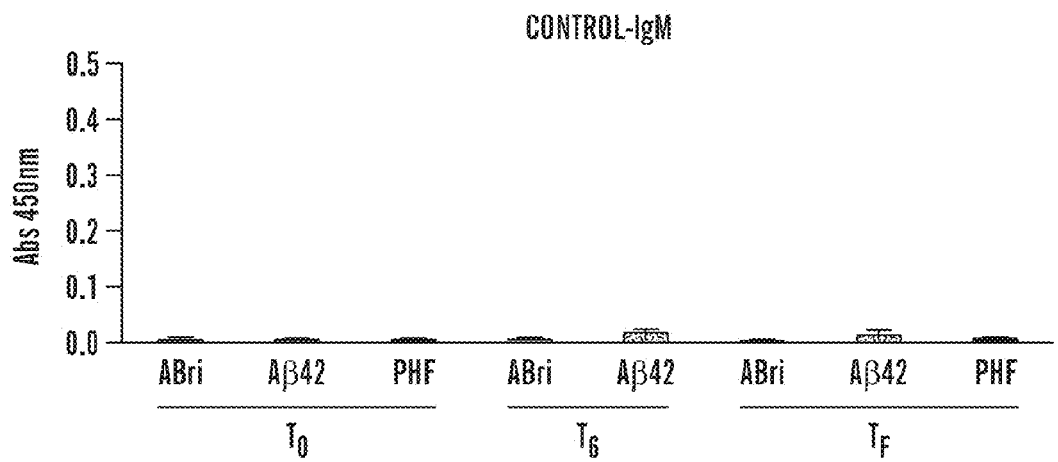
FIGS. 11A-11D are bar graphs of the IgM and IgG antibody levels raised against polymerized ABri, Aβ42, and PHF prior to the first inoculation (T0), after the 6th inoculation (T6) and at the time of sacrifice (TF).
Figure 11B:
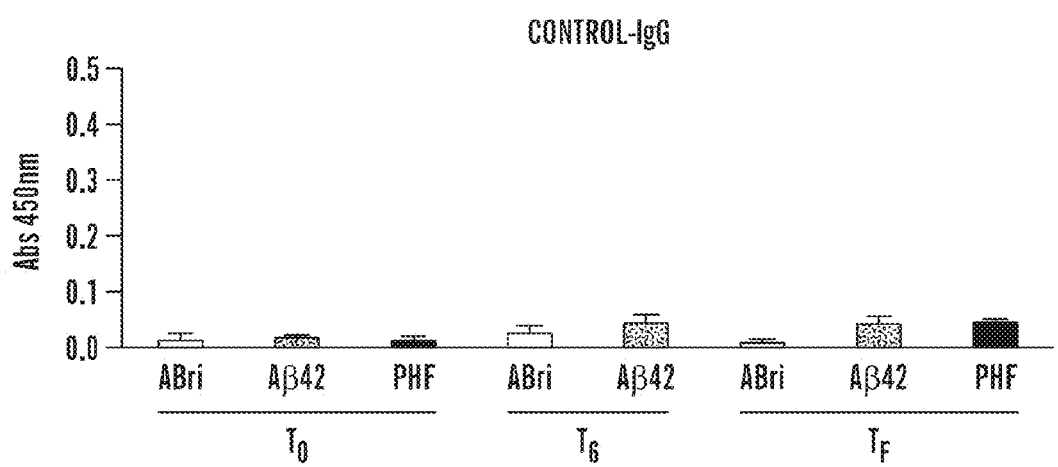
Figure 11C:
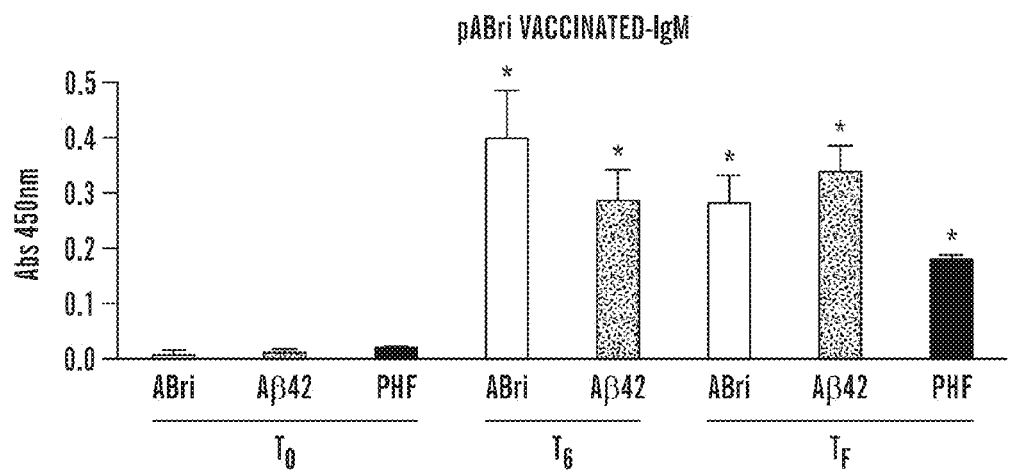
Figure 11D:
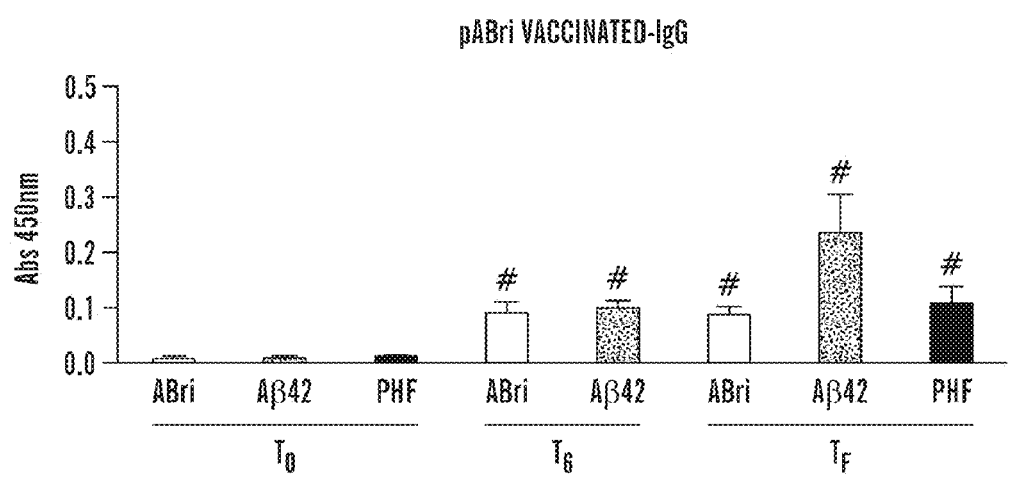

In vehicle control mice there were no significant titers to pABri, Aβ1-42, or purified PHF (FIGS. 11A and 11B). In the pABri vaccinated mice, significant IgG and IgM titers were noted against Aβ42, polymerized ABri, and purified PHF (p-value by unpaired t-test was p<0.0001 and p<0.01 for IgM and IgG respectively for both the bleedings at T6 and TF) (see FIGS. 11C and 11D).

Example 13

Sensorimotor and Cognitive Testing

Figure 13:
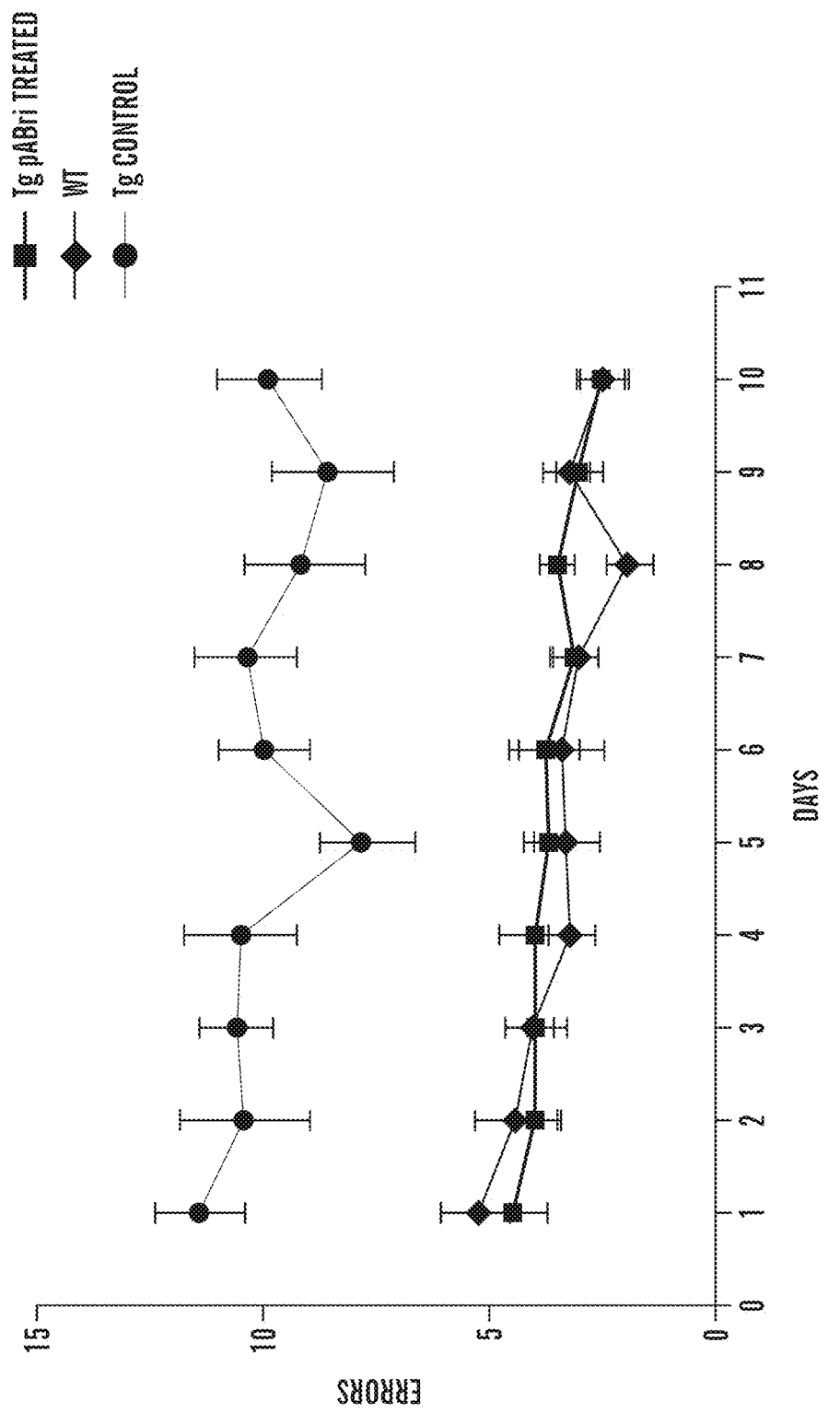
FIG. 13 is a graph depicting the results of the radial arm maze cognitive testing. The number of errors versus the day of testing are plotted for vaccinated AD transgenic mice (Tg pABri Treated), wildtype mice (WT), and AD transgenic control mice (Tg Control). There are statistically significant differences between the untreated control Tg mice versus the pABri treated Tg mice and wild-type controls. By two-way ANOVA the treatment effect was $p<0.0001$. Post-hoc Neuman-Keuls testing indicated that both the wild-type controls and pABri vaccinated Tg mice had significantly fewer errors than the control Tg mice ($p<0.001$). There are no differences between the wild-type controls and the pABri treated Tg mice.

In order to verify that cognitive testing was not confounded by differences in sensorimotor abilities in the ABri vaccinated versus control mice, sensorimotor testing was conducted first. There were no significant difference between the groups in locomotor activity (see FIGS. 12A-12D), traverse beam testing and rotarod testing. Radial arm maze cognitive testing showed there were statistically significant differences between the untreated control Tg mice versus the treated Tg mice and wild-type controls (FIG. 13). By two-way ANOVA the treatment effect was p<0.0001. Post-hoc Neuman-Keuls testing indicated that both the wild-type controls and treated Tg mice were significant different from the control Tg mice (p<0.001). There was no difference between the wild-type controls and the treated Tg mice.

Example 14

Amyloid Quantitation by Stereology and Biochemical Analysis

Figure 14B:
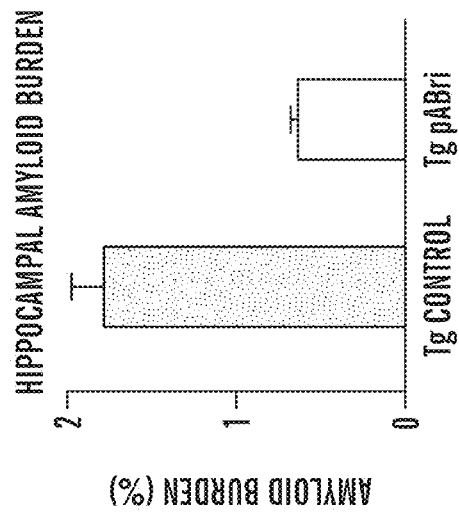
FIGS. 14A-14F depict the amyloid burden in AD transgenic control (Tg Control) and pABri vaccinated AD transgenic animals (Tg pABri).
Figure 14A:
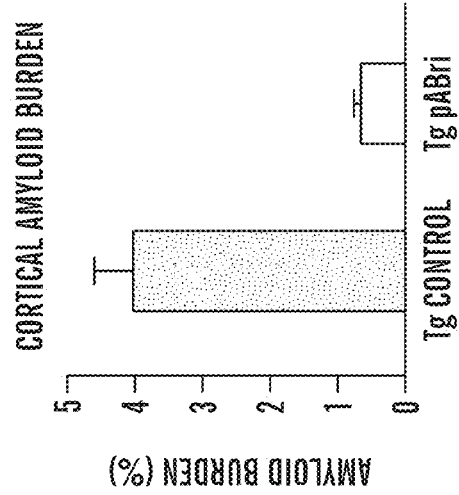
Figure 14D:
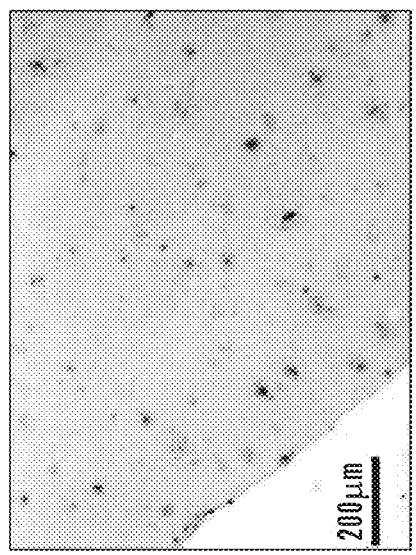
Figure 14F:
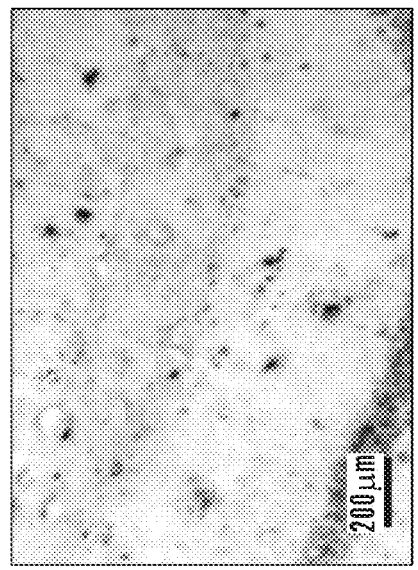
Figure 14C:
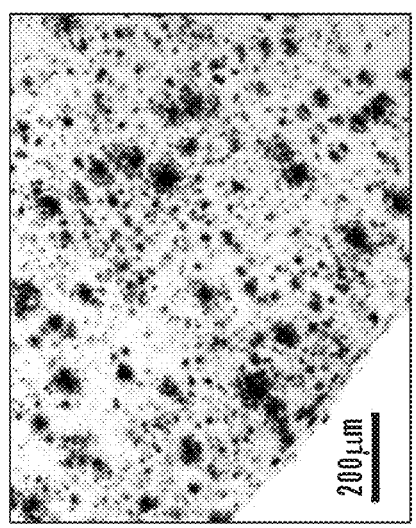
Figure 14E:
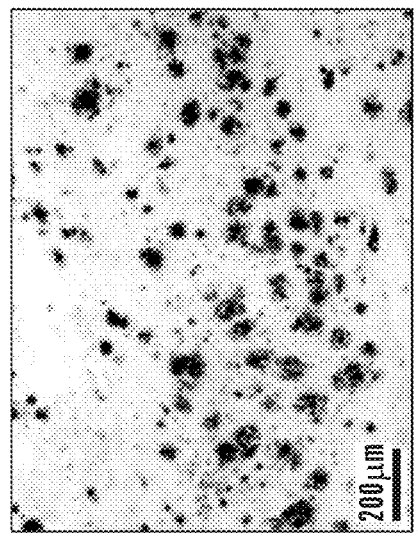
Figure 15A:
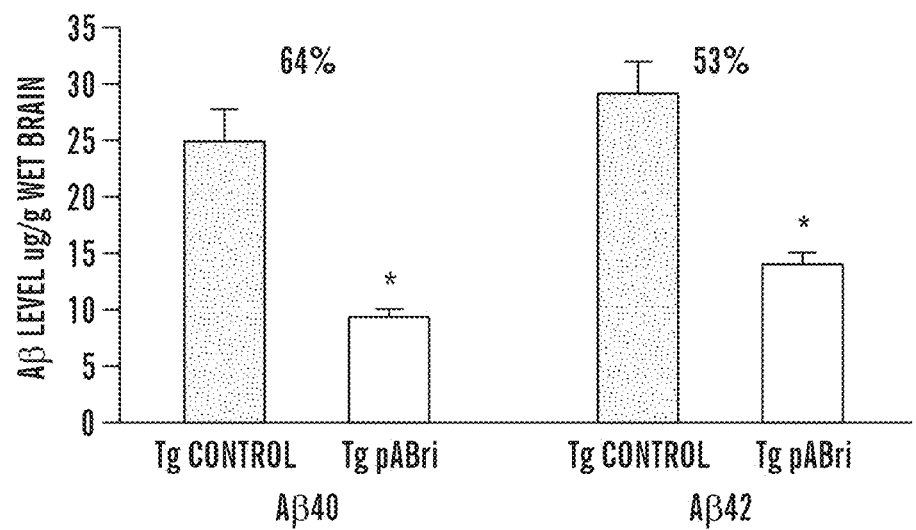
FIGS. 15A-15B are bar graphs showing the levels of Aβ40 and Aβ42 in formic acid and DEA extracted material from brains of control Tg and pABri vaccinated Tg mice. In the formic acid extract fraction (FIG. 15A), Aβ40 and Aβ42 were reduced 64% and 53%, respectively (p<0.001), in the vaccinated mice. In the DEA extracted fraction (FIG. 15B), Aβ40 (p<0.001) and Aβ42 (p=0.002) were reduced by 71% and 57%, respectively, in the vaccinated mice.
Figure 15B:
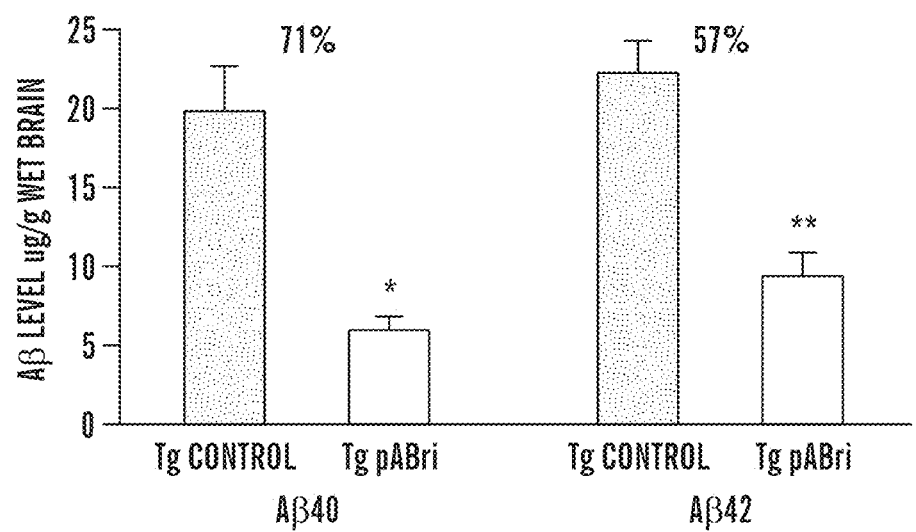

There were significant reductions in the amyloid burden (% area occupied by 4G8/6E10 immunoreactivity) in both the cortex (85% reduction) and hippocampus (65% reduction); p=0.0001 and p=0.0002, respectively (see FIGS. 14A and 14B). Representative immunostained sections are shown in FIG. 14C-14F (scale bar=200 µm). Significant reductions in the biochemically extracted Aβ40 and Aβ42 levels were also noted (FIGS. 15A and 15B). In the formic acid extract fraction Aβ40 and Aβ42 were reduced 64% and 53%, respectively (p<0.001) (FIG. 15A). In the DEA extracted fraction Aβ40 (p<0.001) and Aβ42 (p=0.002) were reduced by 71% and 57%, respectively (FIG. 15B). p-values are by unpaired, two-tailed t-tests.

Example 15

Immunostaining of AD Tissue by Plasma From Immunized Mice

Figure 16B:
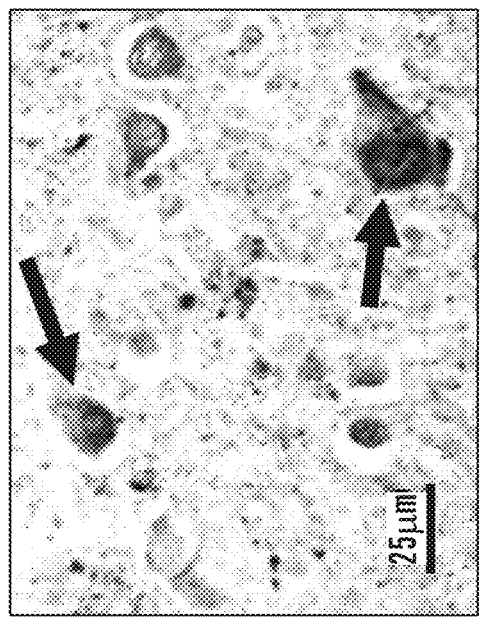
FIGS. 16A-16C are photomicrographs showing immunostaining of human AD and age matched control brain tissue sections using plasma from pABri immunized mice. Plasma from pABri vaccinated Tg mice (obtained after the 6$^{th}$ inoculation (T6)) immunolabeled some plaques (see red arrows) as well as neurofibrillary tangles (NFT) as shown in FIG. 16A. Double immunolabeling with PHF1 (anti-phosphorylated tau mAb) in red and plasma from immunized Tg mice in black showed co-localization of NFT labeling (see red arrows) in FIG. 16B. No immunolabeling in normal control human tissue was detected with plasma from pABri immunized Tg mice (FIG. 16C).
Figure 16A:
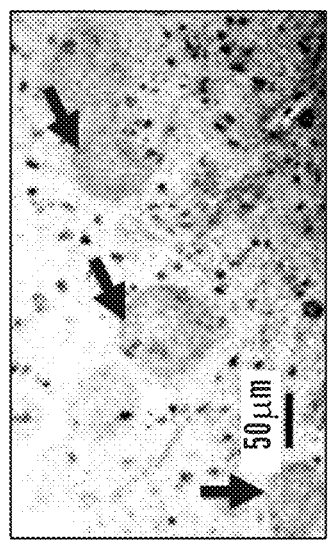
Figure 16C:
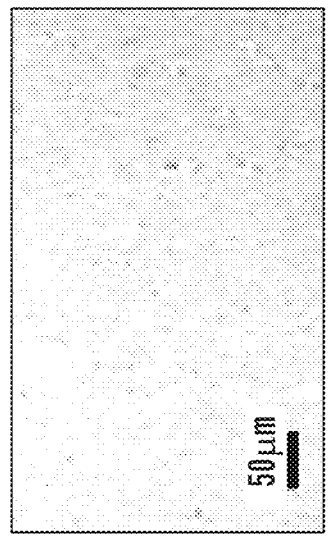

Plasma (T6) from pABri vaccinated Tg mice specifically immunolabeled some plaques as well as some neurofibrillary tangles in brain sections from a patient with confirmed AD (FIG. 16A). Double immunolabeling with PHF1 (anti-phosphorylated tau mAb) and plasma from immunized Tg mice showed co-localization of neurofibrillary tangle labeling (FIG. 16B). The control (i.e., normal human tissue with no AD pathology) failed to show any immunolabeling when exposed to plasma from pABri immunized Tg mice (FIG. 16C).

Example 16

Quantitation of Aβ Oligomers

Figure 17:
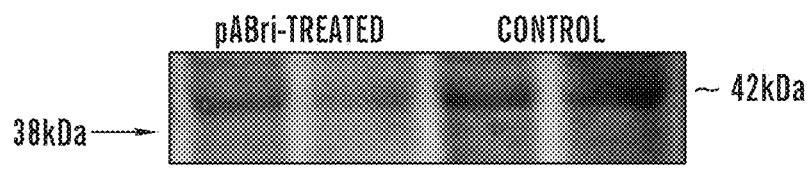
FIG. 17 shows the densitometric quantitation of soluble oligomeric Aβ in brain homogenates of pABri vaccinated Tg and control Tg animals. The levels of pathogenic Aβ oligomers in brain homogenates from two pABri vaccinated and two control Tg mice were assessed by western-blot using the A11 oligomer-specific antibody as illustrated in the immunoblot shown at the top of the Figure. A bar graph of the densitometric analysis of the A11 immunoreactive bands is shown at the bottom of the figure (two-tailed t-test, p<0.05).
Figure 17:
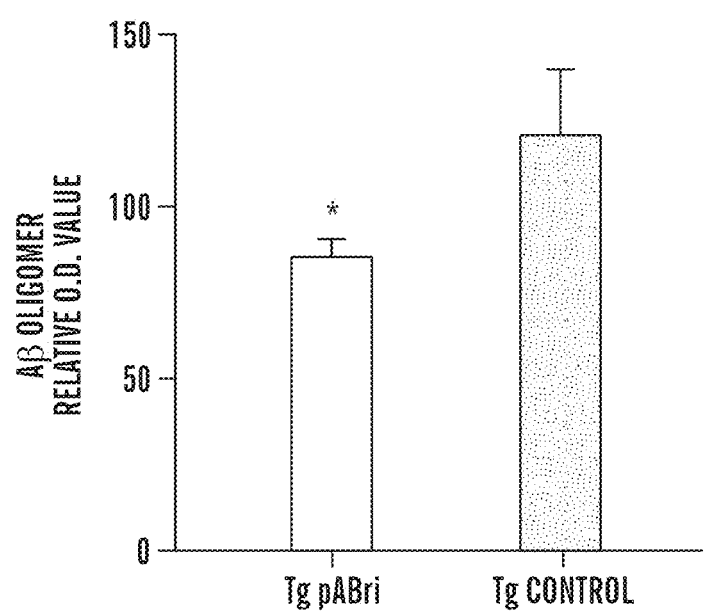

Soluble oligomeric Aβ ligands (also known as ADDLs) may account for memory loss and AD neuropathology, thus presenting a significant therapeutic target (Lublin et al., "Amyloid-Beta Oligomers: Possible Roles As Key Neurotoxins in Alzheimer's Disease," *Mt. Sinai J. Med.* 77:43-49 (2010), which is hereby incorporated by reference in its entirety). The level of pathogenic Aβ oligomers in the brain homogenates were assessed by western-blot using the A11 oligomer-specific antibody (FIG. 17). pABri vaccination led to a significant decrease in the levels of A11 immunoreactive (42 kDa) oligomers (two-tailed t-test, p<0.05).

Example 17

Monoclonal Antibody Production and Characterization

A subset of mice with a high anti-aggregated Aβ1-42 and anti-PrP$^{Sc}$ antibody titer were used for monoclonal antibody production. Cells from the spleens of high responder vaccinated mice (defined as having a titer of >1:2000 against both aggregated Aβ1-42 and PrP$^{Sc}$) were fused with the SP2/0 myeloma cell line to create hybridomas. ELISA was used to screen for potential anti-misfolded protein monoclonal antibodies (mAbs), using a pABri, aggregated Aβ42, aggregated A1340, and PrP$^{Sc}$, with the addition of purified paired helical filament (PHF). In addition, clones that reacted with any of these immunogens with high titer on ELISA were tested on AD sections for immunoreactivity with neuritic plaques and neurofibrillary tangles (NFT).

Figures 18A, 18B:
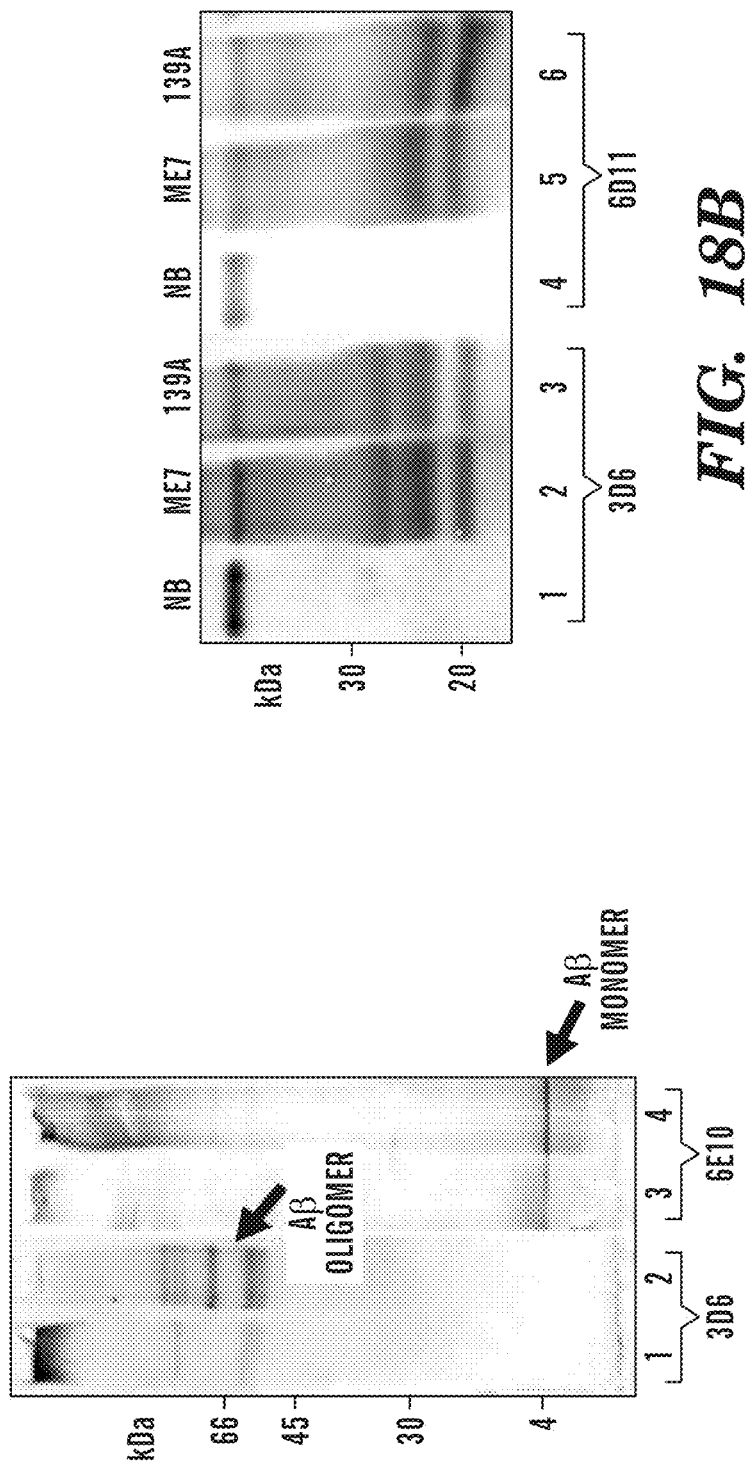
FIGS. 18A-18B are immunoblots showing cross-reactivity of the isolated monoclonal 3D6 antibody for Aβ and PrP$^{Sc}$ oligomers.

The immunoreactivity of one monoclonal antibody, 3D6, against Aβ oligomers and PrP$^{Sc}$ is shown in FIG. 18. Samples containing Aβ1-40 and Aβ1-42 monomers/oligomers were run on SDS-PAGE under non-reducing conditions without boiling to maintain native structures. FIG. 18A shows immunolabeling of Aβ1-40 monomer/oligomers (lanes 1 and 3) and Aβ1-42 monomer/oligomers (lanes 2 and 4) with monoclonal anti-3D6 antibody (lanes 1 and 2; 1:1000) and monoclonal anti-Aβ 6E10 antibody (lanes 3 and 4; 1:20,000). The 3D6 antibody detected both Aβ1-40 and Aβ1-42 oligomers at ~56 kDa and higher molecular weights (lanes 1 and 2 of FIG. 18A), but did not recognize Aβ monomers. The anti-Aβ mAb 6E10 preferentially detects monomeric Aβ with a faint reactivity of oligomers seen in lane 4, as has previously been reported (Kayed et al., "Fibril Specific, Conformation Dependent Antibodies Recognize a Generic Epitope Common To Amyloid Fibrils and Fibrillar Oligomers That Is Absent in Prefibrillar Oligomers," *Mol. Neurodegeneration* 2:18 (2007), which is hereby incorporated by reference in its entirety). When samples were denatured prior to electrophoresis under reducing conditions, no immunolabeling was noted with the 3D6 antibody on western blots.

In FIG. 18B the immunoreactivity of 3D6 against PrP$^{Sc}$ is shown. Protease-K digested normal brain homogenate (lanes 1, 4), ME7/CV murine scrapie mouse brain homogenate (lanes 2, 5) and 139A scrapie infected brain homogenate (lanes 3, 6) were immunodetected with anti-3D6 antibody (lanes 1-3) or anti-PrPc/PrP$^{Sc}$ 6D11 antibody (lanes 4-6). The 3D6 antibody, developed from mice immunized with polymerized ABri (SEQ ID NO:2), detects both PrP$^{Sc}$ and Aβ oligomers (lanes 1-3).

Figure 19A:
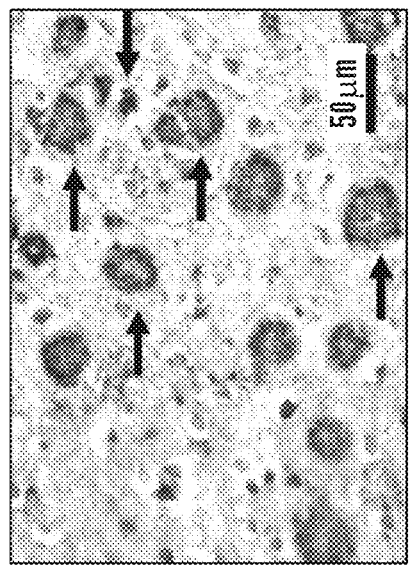
FIGS. 19A-19D show immunohistochemical staining of plaques and neurofibrillary tangles (NFT) on formic acid treated AD cortical (FIGS. 19A and 19C) and hippocampal (FIG. 19B) tissue sections using the 3D6 antibody. The grey and black arrows indicate the detection of plaques and NFTs, respectively.
Figure 19B:
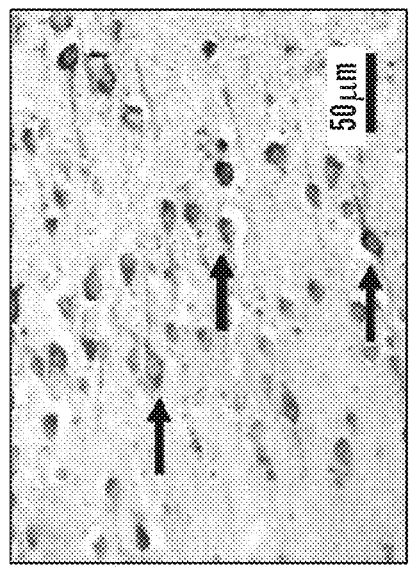
Figure 19C:
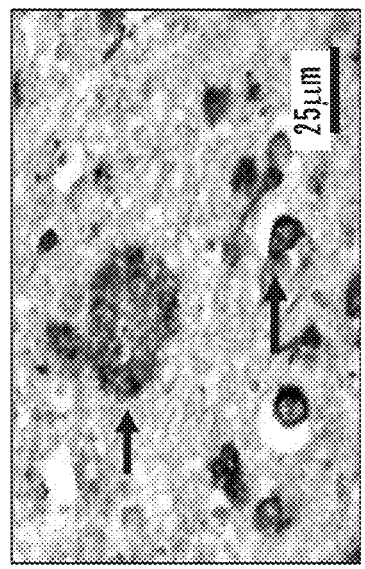
Figure 19D:
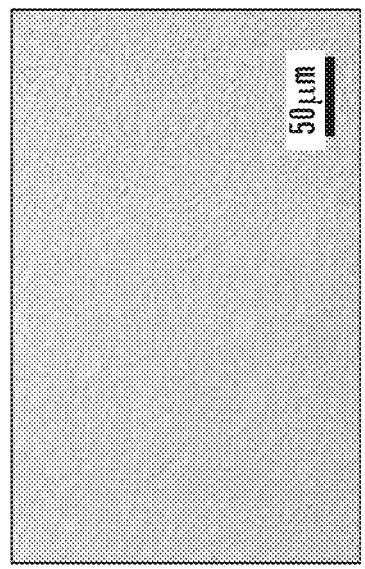

FIGS. 19A-D are photomicrographs showing immunohistochemical staining of plaques and NFTs on formic acid treated AD sections using the 3D6 antibody. FIGS. 19A and 19C are images of frontal cortex tissue sections showing labeled plaques (grey arrows) and NFTs (black arrows). FIG. 19B is an image showing NFT labeling in the hippocampus. In FIG. 19D, 3D6 antibody was absorbed with aggregated Aβ as a control, and no plaque or NFT labeling was detected. Similarly, 3D6 absorbed with PHF and PrP$^{Sc}$ preparations also precluded plaque and NFT labeling. This data demonstrates that in vivo immunization using a polymerized first peptide of the present invention (SEQ ID NO:2) induces an immune response consisting of antibodies that recognize a shared conformational epitope that is common across oligomer/aggregated Aβ, NFT and PrP$^{Sc}$.

Discussion of Examples 1-17

The present study has demonstrated, for the first time, that immunization of an AD Tg mouse model with a foreign peptide in a polymerized, β-sheet rich form induces an immune response to both Aβ42 and PHF through conformational mimicry. The immunogen used corresponds to the 13 amino acids of the carboxyl end of the amyloid that is deposited in British amyloidosis, where a missense mutation in a stop codon results in the transcription of a novel intronic sequence (Vidal et al., "A Stop-Codon Mutation in the BRI Gene Associated With Familial British Dementia," *Nature* 399:776-781 (1999); Ghiso et al., "Amyloidogenesis in Familial British Dementia is Associated With a Genetic Defect on Chromosome 13," *Molecular Basis of Dementia* 920:84-92 (2000); Rostagno et al., "Chromosome 13 Dementias," *Cell Mol. Life Sci.* 62:1814-1825 (2005), which are hereby incorporated by reference in their entirety). This peptide has no homology to known mammalian proteins, but is highly amyloidogenic (Rostagno et al., "Chromosome 13 Dementias," *Cell Mol. Life Sci.* 62:1814-1825 (2005); Srinivasan et al., "pH-Dependent Amyloid and Protofibril Formation by the ABri Peptide of Familial British Dementia," *J. Mol. Biol.* 333:1003-1023 (2003), which are hereby incorporated by reference in their entirety). As expected, the pABri that was used also induced an immune response to its primary sequence. Although antibodies to primary amino acid sequences tend to produce strong reactions with their ligands, this immune response is very unlikely to be associated with autoimmune toxicity since normal mice (and other mammals) do not express this peptide as part of any protein. In fact, this 13 amino acid sequence would only be found in the very rare individuals who are affected with British amyloidosis. This immune response is associated with a strong behavioral rescue in the treated Tg mice as they performed similar to wild type mice in the radial arm maze. The testing of this memory task was not confounded by any differences in the sensorimotor activity between the control and vaccinated mice as shown by the locomotor activity, rotarod and traverse beam testing. Moreover, the behavioral rescue was associated with a marked reduction in the amyloid burden as determined histologically and biochemically. The anti-Aβ42 titers the vaccinated mice developed were relatively modest; however, as has been suggested, behavioral rescue is most closely linked to Aβ oligomer reductions and not with either the degree of amyloid plaque deposition reduction or overall anti-Aβ titer (Janus et al., "Aβ Peptide Immunization Reduces Behavioural Impairment and Plaques in A Model of Alzheimer's Disease," *Nature* 408:979-982 (2000); Morgan et al., "Aβ Peptide Vaccination Prevents Memory Loss in an Animal Model of Alzheimer's Disease," *Nature* 408:982-985 (2000); Asuni et al., "Aβ Derivative Vaccination in Alum Adjuvant Prevents Amyloid Deposition and Does Not Cause Brain Microhemorrhages in Alzheimer's Model Mice," *Eur. J. Neurosci.* 24:2530-2542 (2006), which are hereby incorporated by reference in their entirety). Hence, it is not the absolute degree of the humoral response generated, but its quality in terms of effective targeting of toxic species that is most important. The most toxic forms of Aβ are thought to be oligomeric (Lublin et al., "Amyloid-Beta Oligomers: Possible Roles As Key Neurotoxins in Alzheimer's Disease," *Mt. Sinai J. Med.* 77:43-49 (2010), which is hereby incorporated by reference in its entirety), and, importantly, this study has shown that the approach used is associated with a reduction of these toxic species of Aβ. In addition, the antibody response against the fibrillar forms of Aβ, as seen in histological samples of AD brain sections stained with pABri vaccinated plasma, might also contribute to the overall rescue of behavior seen in the vaccinated cohort.

On the other hand, the majority of active and passive immunization studies in mouse models, and all trials in humans to date have used an approach where both the normal conformer (sAβ) and the pathological conformer (Aβ) are targeted. This is an important short coming, as interfering with normal sAβ will inhibit its physiological functions such as neuroprotection, modulation of long term potentiation and innate immunity (Puzzo et al., "Picomolar Amyloid-Beta Positively Modulates Synaptic Plasticity and Memory in Hippocampus," *J. Neurosci.* 28:14537-14545 (2008); Giuffrida et al., "Beta-Amyloid Monomers Are Neuroprotective," *J. Neurosci.* 29:10582-10587 (2009); Soscia et al., "The Alzheimer's Disease-Associated Amyloid Beta-Protein is an Antimicrobial Peptide," *PLoS ONE* 5:e9505 (2010), which are hereby incorporated by reference in their entirety). In the initial human trial of active vaccination the use of a self-antigen as an immunogen (Aβ42) was associated with encephalitis in some 6% of patients (Gilman et al., "Clinical Effects of Aβ Immunization (AN1792) in Patients with AD in an Interrupted Trial," *Neurol.* 64:1553-1562 (2005), which is hereby incorporated by reference in its entirety). This remains an issue with on-going human trials of passive immunization where a proportion of participants have developed what has been called vasogenic edema (Rinne et al., "$^{11}$C-Pib PET Assessment of Change in Fibrillar Amyloid-Beta Load in Patients with Alzheimer's Disease Treated With Bapineuzumab: A Phase 2, Double-Blind, Placebo-Controlled, Ascending-Dose Study," *Lancet Neurol.* 9(4):363-72 (2010), which is hereby incorporated by reference in its entirety). The active immunomodulatory approach of the present study uses an immunogen that does not correspond to a self-antigen, but through conformational mimicry is able to induce a response that recognizes pathological conformers and is much less likely to be associated with autoimmune toxicity.

Another significant drawback of current immunization approaches tested in humans is that targeting only Aβ related pathology significantly reduces Aβ plaques without evidence of a corresponding significant behavioral rescue in results presented so far (Holmes et al., "Long Term Effects of Aβ42 Immunization in Alzheimer's Disease. Immune Response, Plaque Removal and Clinical Function," *Lancet* 372:216-223 (2008); Rinne et al., "11C-Pib PET Assessment of Change in Fibrillar Amyloid-Beta Load in Patients with Alzheimer's Disease Treated With Bapineuzumab: A Phase 2, Double-Blind, Placebo-Controlled, Ascending-Dose Study," *Lancet Neurol.* 9(4):363-72 (2010), which are hereby incorporated by reference in their entirety). The limited autopsy data from the initial human active vaccination trial targeting Aβ42 showed that patients had partial or near complete plaque removal and a reduction of Aβ load compared to age matched non-immunized controls. However, there were no differences between placebo and active immunization groups in the long-term survival outcome, time to severe dementia, and in cognitive outcome measurements such as ADAS-Cog, MMSE or DAD (Holmes et al., "Long Term Effects of Aβ42 Immunization in Alzheimer's Disease: Immune Response, Plaque Removal and Clinical Function," *Lancet* 372:216-223 (2008), which is hereby incorporated by reference in its entirety). In living patients, as part of a passive immunization trial targeting Aβ, a 25% amyloid reduction versus controls was documented using PET imaging studies, in the absence of measurable cognitive benefits (Rinne et al., "$^{11}$C-Pib PET Assessment of Change in Fibrillar Amyloid-Beta Load in Patients with Alzheimer's Disease Treated With Bapineuzumab: A Phase 2, Double-Blind, Placebo-Controlled, Ascending-Dose Study," *Lancet Neural.* 9(4):363-72 (2010), which is hereby incorporated by reference in its entirety). This suggests that to attain an effective immunotherapeutic approach the targets should include all forms of Aβ toxic conformers and the tau related pathology. The conformational mimicry immunomodulatory approach of the present invention demonstrated that an immune response was evident both against Aβ and PHF pathological forms, as shown by ELISA measurements and tissue staining of human AD sections. Normal human brain sections did not show any immunolabeling with the plasma from pABri vaccinated mice indicating a specificity for pathology associated protein conformers. The fact that the produced antibodies also reacted against mouse prion protein aggregated, indicates the potential use across multiple neurodegenerative diseases and any amyloid diseases other than AD.

In summary, the present invention provides a novel active immunization approach using pABri in a β-sheet rich conformation that targets an abnormal conformation that is shared by aggregated/oligomeric Aβ and PHFs. It is expected that this type of immunomodulatory approach may produce interference or disruption of β-sheet structures in multiple neurodegenerative diseases associated with pathologic protein conformers.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. An isolated antibody or binding portion thereof that binds to a conformational epitope, wherein the conformational epitope is shared by at least two different amyloidogenic proteins or peptides, wherein each of the at least two different amyloidogenic proteins or peptides is a non-fibrillar oligomeric form and contains a β-sheet comprising the conformational epitope; and wherein said antibody or binding portion thereof was raised against a polymerized peptide, wherein the polymerized peptide is selected from the group consisting of:

a polymer of a first peptide comprising the amino acid sequence $X_{1a}X_{2a}X_{3a}X_{4a}X_{5a}X_{6a}X_{7a}X_{8a}X_{9a}X_{10a}X_{11a}X_{12a}X_{13a}$ (SEQ ID NO: 19), wherein $X_{1a}$ is C, M, S, or G; $X_{2a}$ is T, S, or C; $X_{3a}$ is K, R, or H; $X_{4a}$ is S, T, or C; $X_{5a}$ is V, I, or L; $X_{6a}$ is R, K, or H; $X_{7a}$ is R, K, or H; $X_{8a}$ is Q or N; $X_{9a}$ is L, I, or V; $X_{10a}$ is L, I, or V; $X_{11a}$ is D or E; $X_{12a}$ is D or E; $X_{13a}$ is Q or N;

a polymer of a second peptide comprising the amino acid sequence $X_{1b}X_{2b}X_{3b}X_{4b}X_{5b}X_{6b}X_{7b}X_{8b}X_{9b}X_{10b}X_{11b}X_{12b}X_{13b}$ (SEQ ID NO: 20), wherein $X_{1b}$ is C, M, S, or G; $X_{2b}$ is F, Y, or W; $X_{3b}$ is Q or N; $X_{4b}$ is I, L, or V; $X_{5b}$ is F, Y, or W; $X_{6b}$ is I, L, or V; $X_{7b}$ is Q or N; $X_{8b}$ is T, S, or C; $X_{9b}$ is N or Q; $X_{10b}$ is D or E; $X_{11b}$ is R, K, or H; $X_{12b}$ is H, R, or K; $X_{13b}$ is Y, W, or F; and a polymer of a fusion peptide comprising the first and/or second peptides.

2. A pharmaceutical composition comprising:
the antibody or binding portion thereof of claim 1 and
a pharmaceutically acceptable carrier.

3. A diagnostic kit comprising:
the isolated antibody or binding fragment thereof of claim 1 and
a detectable label.

4. The isolated antibody or binding portion thereof of claim 1, consisting of an antibody binding portion that comprises a single variable $V_H$ domain.

5. The isolated antibody binding portion of claim 4, wherein the antibody binding portion consists of a single variable $V_H$ domain.

6. The isolated antibody binding portion of claim 5, wherein the antibody binding portion is humanized.

7. The isolated antibody or binding portion thereof of claim 1, consisting of an antibody binding portion that comprises a single variable $V_L$ domain.

8. The isolated antibody binding portion of claim 7, wherein the antibody binding portion consists of a single variable $V_L$ domain.

9. The isolated antibody binding portion of claim 8, wherein the antibody binding portion is humanized.

10. The isolated antibody or binding portion thereof of claim 1 consisting of a single-chain antibody.

11. The isolated antibody or binding portion thereof of claim 1, consisting of a Fab fragment.

12. The isolated antibody or binding portion thereof of claim 1, wherein the antibody is a monoclonal antibody.

13. The isolated antibody or binding portion thereof of claim 1, wherein the antibody is a humanized antibody.

14. The isolated antibody or binding portion thereof of claim 1, wherein said antibody binds to a conformational epitope of a polymer of the first peptide.

15. The isolated antibody or binding portion thereof of claim 14, wherein the first peptide comprises an amino acid sequence selected from the group consisting of SEQ ID NO: 2, SEQ ID NO: 3, and SEQ ID NO: 5.

16. The isolated antibody or binding portion thereof of claim 1, wherein said binds to a conformational epitope of a polymer of the second peptide.

17. The isolated antibody or binding portion thereof of claim 16, wherein the second peptide comprises an amino acid sequence selected from the group consisting of SEQ ID NO: 8, SEQ ID NO: 9, and SEQ ID NO: 11.

18. The isolated antibody or binding portion thereof of claim 1, wherein said antibody binds to a conformational epitope of a polymer of the fusion peptide.

19. The isolated antibody or binding portion thereof of claim 18, wherein the fusion peptide comprises an amino acid sequence selected from the group consisting of SEQ ID NO: 13, SEQ ID NO: 15, and SEQ ID NO: 17.

20. A method of treating a condition mediated by an amyloidogenic protein or peptide in a subject, said method comprising:
administering to the subject the antibody or binding portion thereof of claim 1 in an amount effective to treat the condition mediated by the amyloidogenic protein or peptide in the subject.

21. A method according to claim 20 further comprising:
selecting a subject having a condition mediated by an amyloidogenic protein or peptide prior to said administering the antibody to the subject.

22. The method according to claim 20, wherein the condition is selected from the group consisting of Alzheimer's disease, Down syndrome, fronto-temporal dementia, Parkinson's disease, hereditary cerebral hemorrhage with amyloidosis, kuru, Creutzfeldt-Jakob disease, Gerstmann-Straussler-Scheinker disease, fatal familial insomnia, British familial dementia, Danish familial dementia, familial corneal amyloidosis, Familial corneal dystrophies, medullary thyroid carcinoma, insulinoma, type 2 diabetes, isolated atrial amyloidosis, pituitary amyloidosis, aortic amyloidosis, plasma cell disorders, familial amyloidosis, senile cardiac amyloidosis, inflammation-associated amyloidosis, familial Mediterranean fever, dialysis-associated amyloidosis, systemic amyloidosis, and familial systemic amyloidosis.

23. A method of diagnosing an amyloid disease in a subject, said method comprising:
   detecting, in the subject, the presence of an amyloidogenic protein or peptide using a diagnostic reagent, wherein the diagnostic reagent comprises the antibody or binding fragment thereof of claim 1, and
   diagnosing an amyloid disease in the subject based on said detecting.

24. The method according to claim 23, wherein said detecting comprising:
   obtaining a biological sample from the subject;
   contacting the biological sample from the subject with the diagnostic reagent under conditions effective for the diagnostic reagent to bind to an amyloidogienic protein or peptide in the sample; and
   detecting binding of the diagnostic reagent to an amyloidogenic protein or peptide in the sample.

25. The method according to claim 23, wherein the diagnostic reagent contains a detectable label and said detecting is carried out using an in vivo imaging device to detect the labeled diagnostic reagent in the subject.

\* \* \* \* \*

```
                         SEQUENCE LISTING

<160> NUMBER OF SEQ ID NOS: 20

<210> SEQ ID NO 1
<211> LENGTH: 34
<212> TYPE: PRT
<213> ORGANISM: Artificial
<220> FEATURE:
<223> OTHER INFORMATION: ABri peptide

<400> SEQUENCE: 1

Glu Ala Ser Asn Cys Phe Ala Ile Arg His Phe Glu Asn Lys Phe Ala
1               5                   10                  15

Val Glu Thr Leu Ile Cys Ser Arg Thr Val Lys Lys Asn Ile Ile Glu
            20                  25                  30

Glu Asn

<210> SEQ ID NO 2
<211> LENGTH: 13
<212> TYPE: PRT
<213> ORGANISM: Artificial
<220> FEATURE:
<223> OTHER INFORMATION: ABri peptide

<400> SEQUENCE: 2

Cys Ser Arg Thr Val Lys Lys Asn Ile Ile Glu Glu Asn
1               5                   10

<210> SEQ ID NO 3
<211> LENGTH: 13
<212> TYPE: PRT
<213> ORGANISM: Artificial
<220> FEATURE:
<223> OTHER INFORMATION: ABri variant peptide

<400> SEQUENCE: 3

Cys Ser Arg Ser Val Lys Lys Gln Ile Ile Glu Glu Asn
1               5                   10

<210> SEQ ID NO 4
<211> LENGTH: 39
<212> TYPE: DNA
<213> ORGANISM: Artificial
<220> FEATURE:
<223> OTHER INFORMATION: ABri variant oligonucleotide

<400> SEQUENCE: 4
tgttctagat cagtcaagaa acaaattatt gaggaaaat                            39
```

<210> SEQ ID NO 5
<211> LENGTH: 13
<212> TYPE: PRT
<213> ORGANISM: Artificial
<220> FEATURE:
<223> OTHER INFORMATION: ABri variant peptide

<400> SEQUENCE: 5

Cys Thr Lys Thr Leu Arg Arg Gln Leu Leu Asp Asp Gln
1               5                   10

<210> SEQ ID NO 6
<211> LENGTH: 39
<212> TYPE: DNA
<213> ORGANISM: Artificial
<220> FEATURE:
<223> OTHER INFORMATION: Abri variant oligonucleotide

<400> SEQUENCE: 6
tgtactaaaa cactcaggag acaacttctt gatgaccaa                              39

<210> SEQ ID NO 7
<211> LENGTH: 34
<212> TYPE: PRT
<213> ORGANISM: Artificial
<220> FEATURE:
<223> OTHER INFORMATION: ADan peptide

<400> SEQUENCE: 7

Glu Ala Ser Asn Cys Phe Ala Ile Arg His Phe Glu Asn Lys Phe Ala
1               5                   10                  15

Val Glu Thr Leu Ile Cys Phe Asn Leu Phe Leu Asn Ser Gln Glu Lys
            20                  25                  30

His Tyr

<210> SEQ ID NO 8
<211> LENGTH: 13
<212> TYPE: PRT
<213> ORGANISM: Artificial
<220> FEATURE:
<223> OTHER INFORMATION: ADan peptide

<400> SEQUENCE: 8

Cys Phe Asn Leu Phe Leu Asn Ser Gln Glu Lys His Tyr
1               5                   10

<210> SEQ ID NO 9
<211> LENGTH: 13
<212> TYPE: PRT
<213> ORGANISM: Artificial
<220> FEATURE:
<223> OTHER INFORMATION: ADan variant peptide

<400> SEQUENCE: 9

Cys Phe Gln Leu Phe Leu Asn Thr Gln Glu Lys His Tyr
1               5                   10

<210> SEQ ID NO 10
<211> LENGTH: 39
<212> TYPE: DNA
<213> ORGANISM: Artificial
<220> FEATURE:
<223> OTHER INFORMATION: ADan variant oligonucleotide

<400> SEQUENCE: 10

-continued

```
tgttttcaat tgttcttgaa cactcaagaa aaacattat                                    39
```

<210> SEQ ID NO 11
<211> LENGTH: 13
<212> TYPE: PRT
<213> ORGANISM: Artificial
<220> FEATURE:
<223> OTHER INFORMATION: ADan variant peptide

<400> SEQUENCE: 11

Cys Trp Gln Leu Trp Ile Gln Ser Asn Asp His Lys Phe
1               5                   10

<210> SEQ ID NO 12
<211> LENGTH: 39
<212> TYPE: DNA
<213> ORGANISM: Artificial
<220> FEATURE:
<223> OTHER INFORMATION: ADan variant oligonucleotide

<400> SEQUENCE: 12

```
tgttggcaat tgtggattca gagtaacgat cataaattt                                    39
```

<210> SEQ ID NO 13
<211> LENGTH: 31
<212> TYPE: PRT
<213> ORGANISM: Artificial
<220> FEATURE:
<223> OTHER INFORMATION: ABri-ADan fusion peptide

<400> SEQUENCE: 13

Cys Ser Arg Thr Val Lys Lys Asn Ile Ile Glu Glu Asn Gly Ser Gly
1               5                   10                  15

Ser Gly Cys Phe Asn Leu Phe Leu Asn Ser Gln Glu Lys His Tyr
            20                  25                  30

<210> SEQ ID NO 14
<211> LENGTH: 93
<212> TYPE: DNA
<213> ORGANISM: Artificial
<220> FEATURE:
<223> OTHER INFORMATION: ABri-ADan fusion oligonucleotide

<400> SEQUENCE: 14

```
tgttctagaa cagtcaagaa aaacattatt gaggaaaatg gtctgggtc tgggtgtttt            60 aatttgttct gaacagtca agaaaaacat tat                                          93
```

<210> SEQ ID NO 15
<211> LENGTH: 31
<212> TYPE: PRT
<213> ORGANISM: Artificial
<220> FEATURE:
<223> OTHER INFORMATION: ABri-ADan fusion peptide

<400> SEQUENCE: 15

Cys Ser Arg Ser Val Lys Lys Gln Ile Ile Glu Glu Asn Gly Ser Gly
1               5                   10                  15

Ser Gly Cys Phe Gln Leu Phe Leu Asn Thr Gln Glu Lys His Tyr
            20                  25                  30

<210> SEQ ID NO 16
<211> LENGTH: 93
<212> TYPE: DNA
<213> ORGANISM: Artificial

```
<220> FEATURE:
<223> OTHER INFORMATION: ABri-ADan fusion oligonucleotide

<400> SEQUENCE: 16
tgttctagat cagtcaagaa acaaattatt gaggaaaatg ggtctgggtc tgggtgtttt      60
caattgttct gaacactca agaaaaacat tat                                    93

<210> SEQ ID NO 17
<211> LENGTH: 31
<212> TYPE: PRT
<213> ORGANISM: Artificial
<220> FEATURE:
<223> OTHER INFORMATION: ABri-ADan fusion peptide

<400> SEQUENCE: 17

Cys Thr Lys Thr Leu Arg Arg Gln Leu Leu Asp Asp Gln Gly Ser Gly
1               5                   10                  15

Ser Gly Cys Trp Gln Leu Trp Ile Gln Ser Asn Asp His Lys Phe
            20                  25                  30

<210> SEQ ID NO 18
<211> LENGTH: 93
<212> TYPE: DNA
<213> ORGANISM: Artificial
<220> FEATURE:
<223> OTHER INFORMATION: ABri-ADan fusion oligonucleotide

<400> SEQUENCE: 18
tgtactaaaa cactcaggag acaacttctt gatgaccaag ggtctgggtc tgggtgttgg      60
caattgtgga ttcagagtaa cgatcataaa ttt                                   93

<210> SEQ ID NO 19
<211> LENGTH: 13
<212> TYPE: PRT
<213> ORGANISM: Artificial
<220> FEATURE:
<223> OTHER INFORMATION: first peptide derived from human Familial
      British Dementia amyloid peptide
<220> FEATURE:
<221> NAME/KEY: VARIANT
<222> LOCATION: (1)..(1)
<223> OTHER INFORMATION: Xaa at position 1 is Cys, Met, Ser, or Gly
<220> FEATURE:
<221> NAME/KEY: VARIANT
<222> LOCATION: (2)..(2)
<223> OTHER INFORMATION: Xaa at position 2 is Thr, Ser, or Cys
<220> FEATURE:
<221> NAME/KEY: VARIANT
<222> LOCATION: (3)..(3)
<223> OTHER INFORMATION: Xaa at position 3 is Lys, Arg, or His
<220> FEATURE:
<221> NAME/KEY: VARIANT
<222> LOCATION: (4)..(4)
<223> OTHER INFORMATION: Xaa at position 4 is Ser, Thr, or Cys
<220> FEATURE:
<221> NAME/KEY: VARIANT
<222> LOCATION: (5)..(5)
<223> OTHER INFORMATION: Xaa at position 5 is Val, Ile, or Leu
<220> FEATURE:
<221> NAME/KEY: VARIANT
<222> LOCATION: (6)..(6)
<223> OTHER INFORMATION: Xaa at position 6 is Arg, Lys, or His
<220> FEATURE:
<221> NAME/KEY: VARIANT
<222> LOCATION: (7)..(7)
<223> OTHER INFORMATION: Xaa at position 7 is Arg, Lys, or His
<220> FEATURE:
<221> NAME/KEY: VARIANT
<222> LOCATION: (8)..(8)
<223> OTHER INFORMATION: Xaa at position 8 is Gln or Asn
```

```
<220> FEATURE:
<221> NAME/KEY: VARIANT
<222> LOCATION: (9)..(9)
<223> OTHER INFORMATION: Xaa at position 9 is Leu, Ile, or Val
<220> FEATURE:
<221> NAME/KEY: VARIANT
<222> LOCATION: (10)..(10)
<223> OTHER INFORMATION: Xaa at position 10 is Leu, Ile, or Val
<220> FEATURE:
<221> NAME/KEY: VARIANT
<222> LOCATION: (11)..(11)
<223> OTHER INFORMATION: Xaa at position 11 is Asp or Glu
<220> FEATURE:
<221> NAME/KEY: VARIANT
<222> LOCATION: (12)..(12)
<223> OTHER INFORMATION: Xaa at position 12 is Asp or Glu
<220> FEATURE:
<221> NAME/KEY: VARIANT
<222> LOCATION: (13)..(13)
<223> OTHER INFORMATION: Xaa at position 13 is Gln or Asn

<400> SEQUENCE: 19

Xaa Xaa Xaa Xaa Xaa Xaa Xaa Xaa Xaa Xaa Xaa Xaa Xaa
1               5                   10

<210> SEQ ID NO 20
<211> LENGTH: 13
<212> TYPE: PRT
<213> ORGANISM: Artificial
<220> FEATURE:
<223> OTHER INFORMATION: second peptide derived from human Familial
      Danish Dementia amyloid peptide
<220> FEATURE:
<221> NAME/KEY: VARIANT
<222> LOCATION: (1)..(1)
<223> OTHER INFORMATION: Xaa at position 1 is Cys, Met, Ser, or Gly
<220> FEATURE:
<221> NAME/KEY: VARIANT
<222> LOCATION: (2)..(2)
<223> OTHER INFORMATION: Xaa at position 2 is Phe, Tyr, or Trp
<220> FEATURE:
<221> NAME/KEY: VARIANT
<222> LOCATION: (3)..(3)
<223> OTHER INFORMATION: Xaa at position 3 is Gln or Asn
<220> FEATURE:
<221> NAME/KEY: VARIANT
<222> LOCATION: (4)..(4)
<223> OTHER INFORMATION: Xaa at position 4 is Ile, Leu, or Val
<220> FEATURE:
<221> NAME/KEY: VARIANT
<222> LOCATION: (5)..(5)
<223> OTHER INFORMATION: Xaa at position 5 is Phe, Tyr, or Trp
<220> FEATURE:
<221> NAME/KEY: VARIANT
<222> LOCATION: (6)..(6)
<223> OTHER INFORMATION: Xaa at position 6 is Ile, Leu, or Val
<220> FEATURE:
<221> NAME/KEY: VARIANT
<222> LOCATION: (7)..(7)
<223> OTHER INFORMATION: Xaa at position 7 is Gln or Asn
<220> FEATURE:
<221> NAME/KEY: VARIANT
<222> LOCATION: (8)..(8)
<223> OTHER INFORMATION: Xaa at position 8 is Thr, Ser, or Cys
<220> FEATURE:
<221> NAME/KEY: VARIANT
<222> LOCATION: (9)..(9)
<223> OTHER INFORMATION: Xaa at position 9 is Asn or Gln
<220> FEATURE:
<221> NAME/KEY: VARIANT
<222> LOCATION: (10)..(10)
<223> OTHER INFORMATION: Xaa at position 10 is Asp or Glu
<220> FEATURE:
<221> NAME/KEY: VARIANT
<222> LOCATION: (11)..(11)
<223> OTHER INFORMATION: Xaa at position 11 is Arg, Lys, or His
<220> FEATURE:
```

-continued

```
<221> NAME/KEY: VARIANT
<222> LOCATION: (12)..(12)
<223> OTHER INFORMATION: Xaa at position 12 is His, Arg, or Lys
<220> FEATURE:
<221> NAME/KEY: VARIANT
<222> LOCATION: (13)..(13)
<223> OTHER INFORMATION: Xaa at position 13 is Tyr, Trp, or Phe

<400> SEQUENCE: 20

Xaa Xaa Xaa Xaa Xaa Xaa Xaa Xaa Xaa Xaa Xaa Xaa Xaa
1               5                   10
```